(12) United States Patent
Spiegel et al.

(10) Patent No.: US 9,556,167 B2
(45) Date of Patent: Jan. 31, 2017

(54) TLR-AGONIST-CONJUGATED ANTIBODY RECRUITING MOLECULES (TLR-ARMS)

(71) Applicant: YALE UNIVERSITY, New Haven, CT (US)

(72) Inventors: David Spiegel, New Haven, CT (US); Kelly Fitzgerald, New Haven, CT (US)

(73) Assignee: YALE UNIVERSITY, New Haven, CT (US)

( * ) Notice: Subject to any disclaimer, the term of this patent is extended or adjusted under 35 U.S.C. 154(b) by 0 days.

(21) Appl. No.: 14/397,995

(22) PCT Filed: May 1, 2013

(86) PCT No.: PCT/US2013/039007
§ 371 (c)(1),
(2) Date: Oct. 30, 2014

(87) PCT Pub. No.: WO2013/166110
PCT Pub. Date: Nov. 7, 2013

(65) Prior Publication Data
US 2015/0110742 A1     Apr. 23, 2015

Related U.S. Application Data

(60) Provisional application No. 61/641,413, filed on May 2, 2012, provisional application No. 61/793,115, filed on Mar. 15, 2013.

(51) Int. Cl.
| | | |
|---|---|---|
| *A61K 31/53* | (2006.01) | |
| *C07D 471/04* | (2006.01) | |
| *A61K 47/48* | (2006.01) | |
| *B82Y 5/00* | (2011.01) | |
| *A61K 45/06* | (2006.01) | |
| *C07K 16/44* | (2006.01) | |

(52) U.S. Cl.
CPC ............ *C07D 471/04* (2013.01); *A61K 31/53* (2013.01); *A61K 45/06* (2013.01); *A61K 47/48638* (2013.01); *A61K 47/48746* (2013.01); *B82Y 5/00* (2013.01); *C07K 16/44* (2013.01); *C07K 2317/732* (2013.01)

(58) Field of Classification Search
USPC .......................................... 544/180; 514/241
See application file for complete search history.

(56) References Cited

U.S. PATENT DOCUMENTS

| | | |
|---|---|---|
| 8,858,509 B2 | 10/2014 | Field |
| 8,859,509 B2 | 10/2014 | Spiegel |
| 9,181,224 B2 | 11/2015 | Spiegel |
| 2012/0269766 A1 | 10/2012 | Spiegel et al. |
| 2013/0245040 A1 | 9/2013 | Spiegel |
| 2014/0308342 A1 | 10/2014 | Spiegel |
| 2015/0018395 A1 | 1/2015 | Spiegel |
| 2015/0087609 A1 | 3/2015 | Spiegel |

FOREIGN PATENT DOCUMENTS

| | | | |
|---|---|---|---|
| WO | WO 2009/157628 | * | 12/2009 |
| WO | 2011/046946 A2 | | 4/2011 |
| WO | 2011046946 | | 4/2011 |
| WO | 2012/068366 A2 | | 5/2012 |
| WO | 2012068366 | | 5/2012 |
| WO | 2013070688 | | 5/2013 |
| WO | 2013070688 A1 | | 5/2013 |
| WO | 2013162757 | | 10/2013 |
| WO | 2014178878 | | 11/2014 |

OTHER PUBLICATIONS

Nishimura et al. CAS: 146: 16458, 2006.*
Baker et al. et al. CAS: 154: 565980, 2011.*
Jung et al. CAS: 152:90702, 2009.*
Onofiok et al. CAS:154: 59448, 2010.*

* cited by examiner

*Primary Examiner* — Rei-Tsang Shiao
(74) *Attorney, Agent, or Firm* — Henry D. Coleman; R. Neil Sudol

(57) ABSTRACT

The present invention relates to chimeric chemical compounds which are used to recruit antibodies to cancer cells, in particular, prostate cancer cells or metastasized prostate cancer cells. The compounds according to the present invention comprise an antibody binding terminus (ABT) moiety covalently bonded to a cell binding terminus (CBT) and Toll-like receptor agonist (TLR) through a linker and a multifunctional connector group or molecule.

46 Claims, 20 Drawing Sheets

TLR-AGONIST-CONJUGATED ANTIBODY RECRUITING MOLECULES (TLR-ARMS)

This application is a United States national phase application of and claims priority from international patent application number PCT/US2013/039007 filed May 1, 20013 which claims the benefit of priority of provisional application Ser. No. U.S. 61/641,413, filed May 2, 2012 and U.S. 61/793,115, filed Mar. 15, 2013, each of identical title to the present application, said applications being incorporated by reference in their entirety herein.

RELATED APPLICATIONS AND GRANT SUPPORT

This invention was made with government support under RR024139 awarded by National Institute of Health. The government has certain rights in the invention.

FIELD OF THE INVENTION

The present invention relates to chemical compounds which are used to recruit antibodies to cancer cells, including prostate cancer cells or metastasized prostate cancer cells and provide a heightened response. The compounds according to the present invention comprise an antibody binding terminus [ABT] moiety covalently bonded to a cell binding terminus [CBT] and an adjuvant moiety based upon Toll-like Receptor agonists [TLR] comprising a TLR agonist (preferably a TLR7/8 agonist) through a linker and a multifunctional connector molecule. In addition, given that the protein target is found on the neovasculature of most non-prostatic cancer cells, the compounds in the present invention also serves as cancer therapy (through an antiangiongenic mechanism) for other cancer types.

BACKGROUND AND OVERALL DISCUSSION OF THE INVENTION

A growing wealth of data indicates that targeted therapies can mobilize a patient's own immune system to destroy malignancies with fewer side effects than traditional chemotherapy. Since it is estimated that 41% of Americans—almost 1 in 2 people—born in 2011 will develop cancer in their lifetime,[8] the generation of more effective cancer immunotherapies is a high priority. These therapies include monoclonal antibodies (mAbs) that direct innate immune cells to tumor-associated antigens (TAA) as well as cancer "vaccines" that take many forms (including injections of tumor proteins with adjuvants or ex vivo primed dendritic cells) and are designed with the intention of inducing long-lasting anti-tumor T-cells.[1] The objective of the present inventors' research is to develop novel compounds capable of stimulating both innate and adaptive immune responses against tumors, thereby combining the immunologic strengths of both mAbs and cancer vaccines in a small molecule format.

To date, mAbs have demonstrated the greatest clinical efficacy of all cancer immunotherapeutics, with nine unconjugated mAbs against TAA approved by the FDA over the past 15 years.[9] To capitalize on this therapeutic success but reduce the disadvantages of mAbs (expensive to produce, can provoke allergic reactions, lack oral bioavailability), the present inventors have developed small-molecule antibody recruiting molecules (ARMs)[2]. ARMs take advantage of the high prevalence of preexisting antibodies against dinitrophenol (DNP) in human serum, possibly caused by pesticide exposure. These molecules redirect anti-DNP antibodies to prostate cancer and other cancer cells expressing prostate specific membrane antigen (PSMA). PSMA is a membrane protein expressed at high abundance in human prostate carcinoma, but present at low levels in normal prostate and non-prostatic tissues.[10] We have shown that ARMs are able to mediate prostate cancer destruction both in vitro[2] and in vivo[11] through both antibody dependent cellular cytotoxicity (ADCC) and phagocytosis (ADCP) by innate effector cells.

While the traditional view holds that mAbs act primarily through the innate immune system, burgeoning evidence highlights their link to adaptive immunity.[12] Antibody-opsonized tumors or soluble TAA immune complexes induce phagocytosis or endocytosis through Fcγ receptors (FcγRs) on dendritic cells (DCs).[3,4] This mode of internalization leads to increased presentation of TAA peptides on MHC I and II, increased costimulatory molecule expression, and increased generation of antigen-specific CD4+ and CD8+ T-cells as compared to unopsonized antigen.[13-16] In mice, anti-CD20 and anti-Her2/neu mAbs were shown to induce adaptive anti-tumor immunity,[17,18] while in humans, clinical response following anti-Her2/neu therapy correlates with greater increases in endogenous anti-Her2/neu antibodies and anti-tumor CD4+ T-cells.[19,20]

Unfortunately, across all monoclonal antibodies used for tumor therapy, only about 30% of treated patients experience increased progression-free or overall survival.[20,21] The tumor microenvironment can be highly immunosuppressive, characterized by release of anti-inflammatory paracrine factors, consumption of metabolites necessary for Teff proliferation, and recruitment of tolerogenic cells such as regulatory T-cells (Tregs).[5] Many tumors are also poorly immunogenic in that, despite their malignant transformation, they consist of mostly self-proteins to which the immune system is tolerant Immunogenic epitopes arising from mutated gene products, expression of oncofetal proteins, or aberrant posttranslational modifications may represent only a small fraction of a tumor's total protein. Clearly, additional immuno stimulation beyond unmodified anti-tumor mAbs is required to mount a successful adaptive immune response in the majority of patients.

Advances in the cancer vaccine field have underlined the importance of adjuvants in generating immunity. Toll-like receptor (TLR) agonists are particularly powerful adjuvants, since the natural ligands of these receptors are highly conserved pathogen-associated molecular patterns that are recognized as primal danger signals by the immune system.[22] pursuant to the present invention, the inventors propose to attach the synthetic small-molecule TLR7/8 agonist imiquimod and related TLR7/8 agonists to the ARM scaffold. Located in endosomes, TLRs 7/8 mediate production of proinflammatory cytokines and induce maturation of antigen presenting cells (APCs).[6,7] TLR7/8 agonists can heighten innate responses, especially through plasmacytoid dendritic cells, as well as potentiate adaptive Th1 polarization and cytotoxic T-cell (CTL) generation.[23] Imiquimod is already FDA-approved for topical use against skin malignancies and has also been tested systemically as an experimental vaccine adjuvant.[24,25] It is the present inventors' view that the conjugation of imiquimod to an ARM will better stimulate APC activation and generate anti-tumor T-cells while also improving the ARM's ability to mediate tumor lysis by innate immune cells.

The direct conjugation of imiquimod and other TLR7/8 agonists to the ARM offers crucial advantages over co-administration of unlinked molecules. Several mouse studies have shown that antigen-specific CD4+ and CD8+ T-cell generation dramatically improved when injected antigen was directly linked to TLR7/8 agonists.[26-28] Systemically administered TLR7/8 agonists in human trials have provoked significant adverse effects including fever, fatigue, nausea, chills, and myalgia without demonstrating much efficacy.[29, 29, 30] Physical conjugation to the larger ARM should (1) increase the therapeutic index of the TLR7/8 agonist's (e.g. imiquimod's) therapeutic index by preventing its interaction with endosomal TLR7/8 until phagocytosis of an ARM-opsonized target cell has occurred and (2) localize the immunostimulant to the tumor site. Beyond this superior pharmacokinetic profile, there is some evidence that control of antigen presentation is phagosome-autonomous, meaning that TLR agonists must be located in the same endosome as phagocytosed TAA to best enhance TAA peptide presentation on MHC I or II.[27, 31, 32] Extensive preclinical and clinical data thus support the conjugation of TLR7/8 agonists to antibody recruiting molecules for greater induction of anti-tumor immunity.

THE PRESENT INVENTION

The present invention relates to compounds which are designated TLR-ARMs. TLR-ARMs are multifunctional small molecules designed to stimulate both innate and adaptive anti-tumor immune responses. The inventors have previously developed bifunctional antibody recruiting molecules (ARMs) able to redirect endogenous antibodies to prostate cancer cells expressing prostate specific membrane antigen (PSMA). The present invention enhances the immunostimulatory properties of ARMs by attaching TLR agonists (potent pro-inflammatory molecules) to the ARM scaffold. The binding moieties from the parent compound target the immune response to cancer cells, in particular, prostate cancer cells, while the additional TLR agonistic motif activates local antigen presenting cells for induction of immunologic memory against the tumor. The result is an effect which provides synergistic anticancer activity which is substantially greater than the anticancer activity of individual functional molecules which are not linked through a multifunctional connector [MULLTICON] as in the present invention.

When prostate cancer is diagnosed prior to metastasis, the patient has a greater then 99% chance of survival. The most successful means for treating prostate cancer at this stage is a radical prostatectomy. Unfortunately, this surgery carries with it the risk of severing nerves and blood vessels associated with sexual organs and the bladder, and can potentially result in impotency and/or incontinency. Radiation therapy is yet another commonly used procedure that carries the risk of impotency. Half the patients who undergo radiation therapy for prostate cancer become impotent within 2 years of treatment. In addition to the adverse affects associated with these procedures, they are significantly less effective in patients whose cancer has already delocalized or metastasized on diagnosis. In these cases, patients generally undergo even more invasive procedures such as hormonal therapy or chemotherapy. Unfortunately, most patients eventually stop responding to hormonal therapy and the most successful chemotherapeutic, Taxotere, only prolongs the life of advanced prostate cancer patients by 2.5 months on average.

As discussed above, monoclonal antibody (mAb)-based immunotherapy has proven clinically beneficial for cancer patients while allowing them to maintain a good quality of life. These antibodies can either regulate proliferation of cancer cells through the manipulation of signal transduction, or promote cytotoxicity. Two examples of FDA-approved mAb-based anticancer drugs are Herceptin and Rituxan (Rituximab), which are currently being used for the treatment of breast cancer and non-Hodgkin's lymphoma, respectively. While there are no mAb-based therapeutics currently available for prostate cancer patients, advanced clinical studies on mAb-based immunotherapy has shown promise for the treatment of prostate cancer including advanced prostate cancer. Despite the major advantages of mAb-based immunotherapy, there are significant pitfalls which may limit its potential. In general, mAb-based therapeutics are highly costly ($70,000 for full course of treatment of Herceptin), lack oral bioavailability, and can lead to severe and often fatal side-effects. For example, Herceptin is associated with heart problems and cannot be administered to approximately 10% of cancer patients because of heart-related complications. Rituxan can cause several side-effects which include renal failure, infections and immune and pulmonary toxicity.

Now, no longer in its infancy, the concept of using small molecules to template the human immune response has shown realistic potential. Recent reports have surfaced in which small molecules have been used to direct antibodies to cancerous cells such as breast carcinoma cells, melanoma cells, and nasopharyngeal epidermal carcinoma cells. Animal studies have demonstrated that these molecules can promote tumor rejection and antitumor immunity in mice. Because this process allows for the direction of endogenous antibodies selectively to the cell of interest, it has the potential to harness the power of mAb-based therapeutics while limiting the costs and side effects associated with administering exogenous antibodies. By developing similar methods which recruit anti-DNP antibodies to prostate cancer cells, the proposed research will help broaden this field while creating a new therapy for all forms of prostate cancer, as well as numerous other cancers.

ARM-P-IMQ, compound 1.6 results from this facile, stepwise synthesis. This approach may be used as a generic chemical synthesis for a large number of TLR-ARMs of the present invention.

Figure 6:
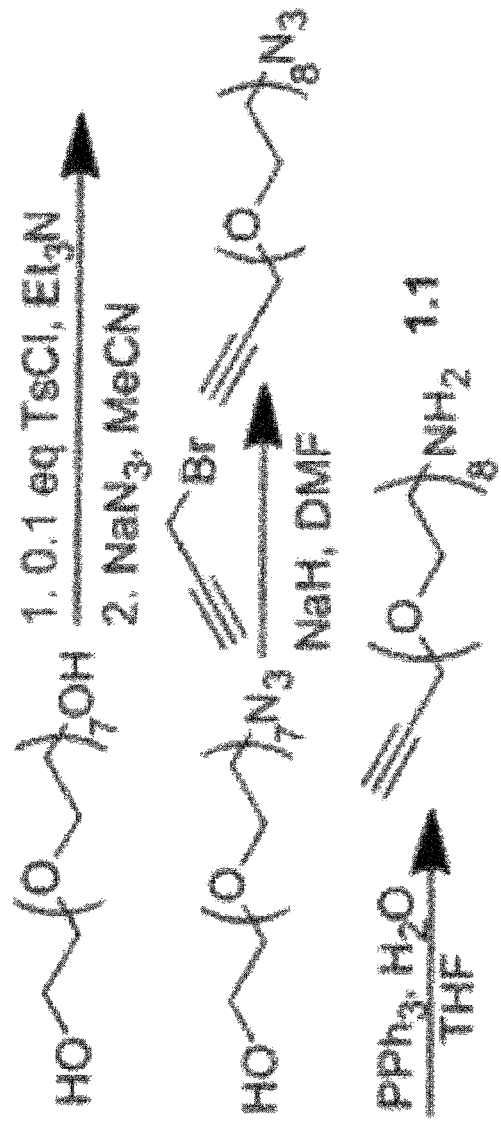

FIG. 6 shows a representative chemical synthesis of a linker for the PSMA binding moiety (CBT), which includes a difunctional connector molecule DiCON based upon triazole. The resulting acetylenic amine compound 1.1 can be used to create the triazole connector moiet (DICON) for providing a linker attached to the CBT moiety. The amine group at the distal end of 1.1 can be used to link the CBT moiety to the multifunctional connector (MULTICON).

Figure 5:
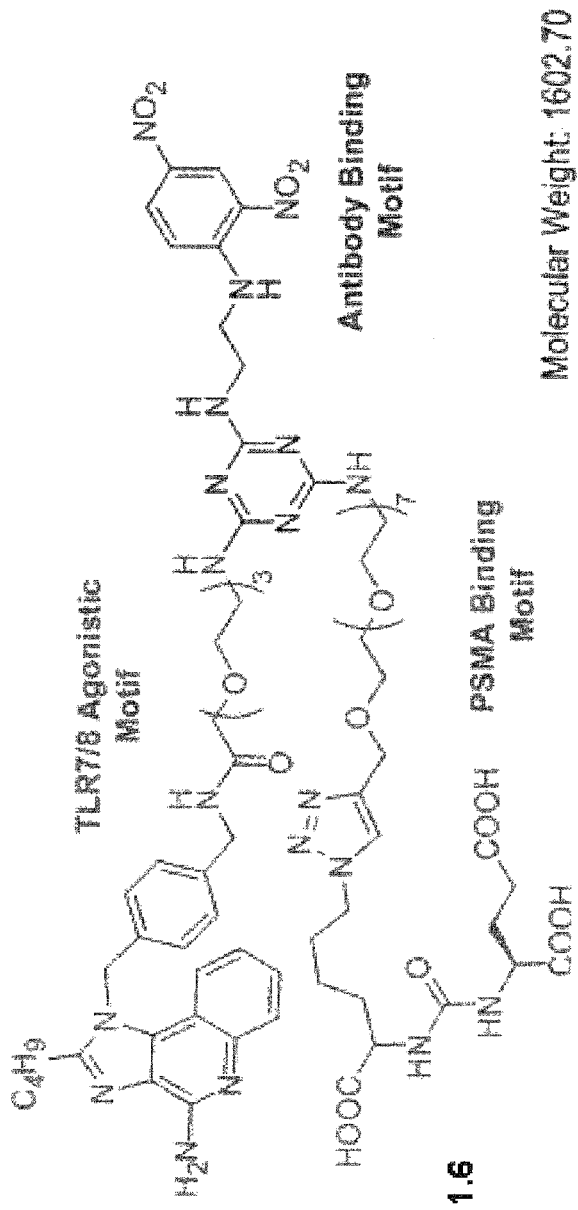
FIG. 5 shows the conjugation of the three moieties (TLR, CBT and ABT) to the connector moiety (CON) precuror, which in the figure is a trihalogenated 1,3,5-triazine group.
Figure 7:
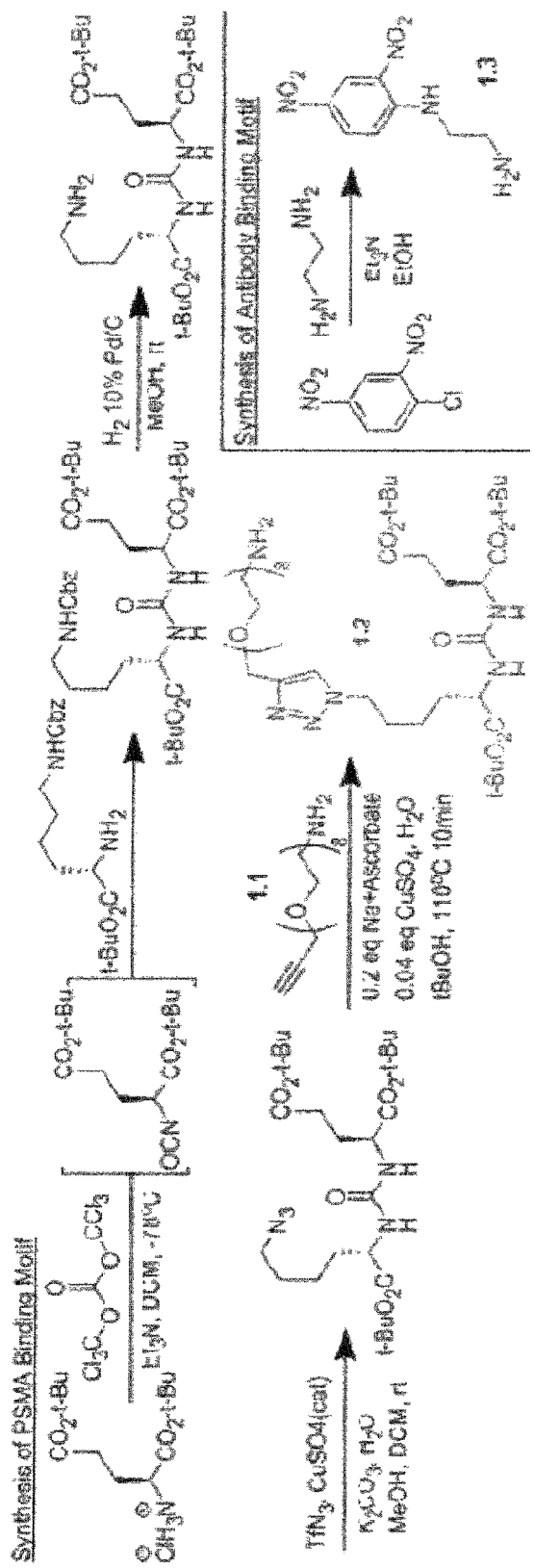

FIG. 7 shows a representative chemical synthesis of the PSMA binding moiety from the ammonium diester. The ammonium diester is first converted to an isocyanate group which is then reacted with the amine protected lysine analog to form the derivatized protected dipeptide, which is deprotected and modified to provide an azido group from the deprotected amine. The azido containing component is reacted with the actylenic amine PSMA linker 1.1 which provides the PSMA binding moiety conjugated to a linker through a difunctional triazine connector moiety. FIG. 5 (insert) shows the synthesis of the Antibody Binding Terminus Moiety (ABT) based upon a dinitrophenyl group by displacing a halogen on the halogenated dinitrophenyl starting material to provide the free amine substituted DNP analog 1.3.

Figure 8:
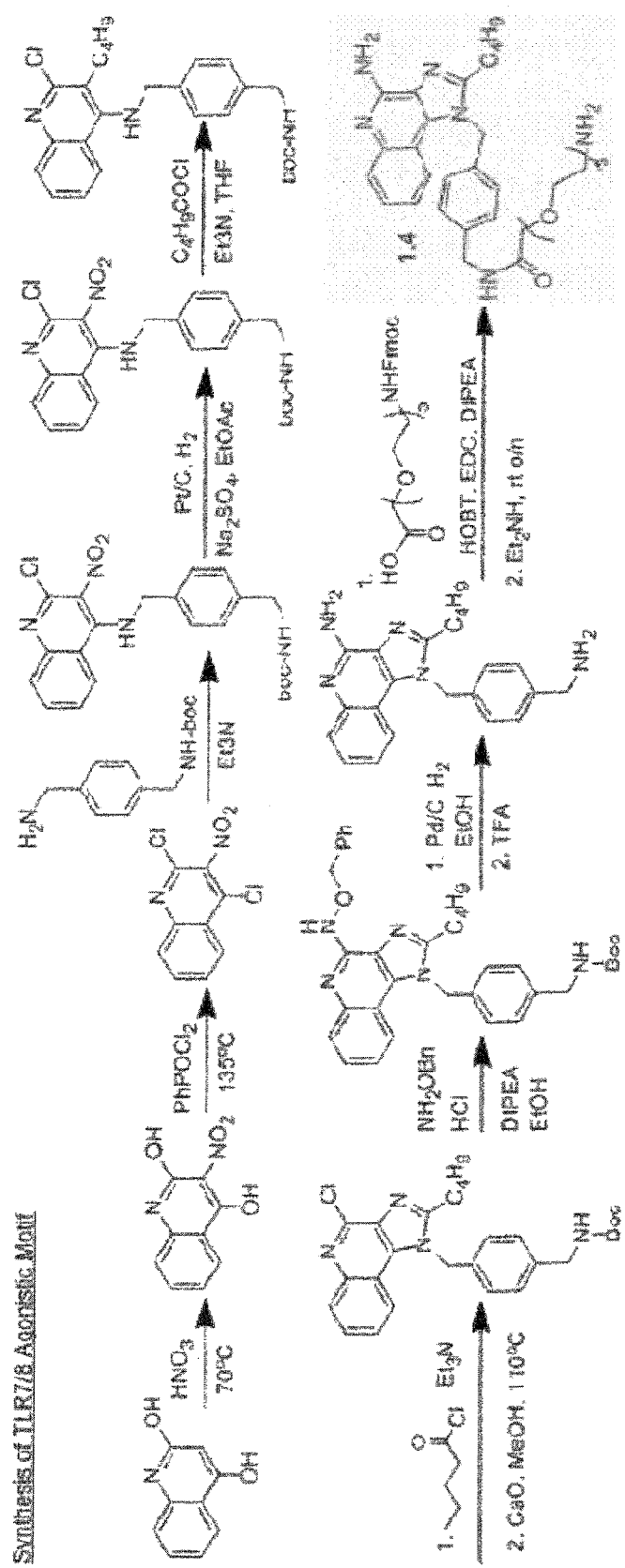

FIG. 8 shows a representative synthesis of a TLR agonist moiety from dihydroxyquinoline as indicated. The free amine substituted TLR agonist moiety of Imiquimod is synthesized step-wise pursuant to the scheme set forth in FIG. 6. Other TLR7/8 agonists may be functionalize readily on an available electrophilic or nucleophilic functional group on the TLR7/8 agonist compound. The available functional group of the TLR7/8 agonist may be condensed to provide a linker group which can subsequently be linked to a multifunctional connector moiety (MULTICON) and in turn, to an antibody binding terminus (ABT) and a PSMA binding terminus/cell binding terminus (CBT).

Figure 9:
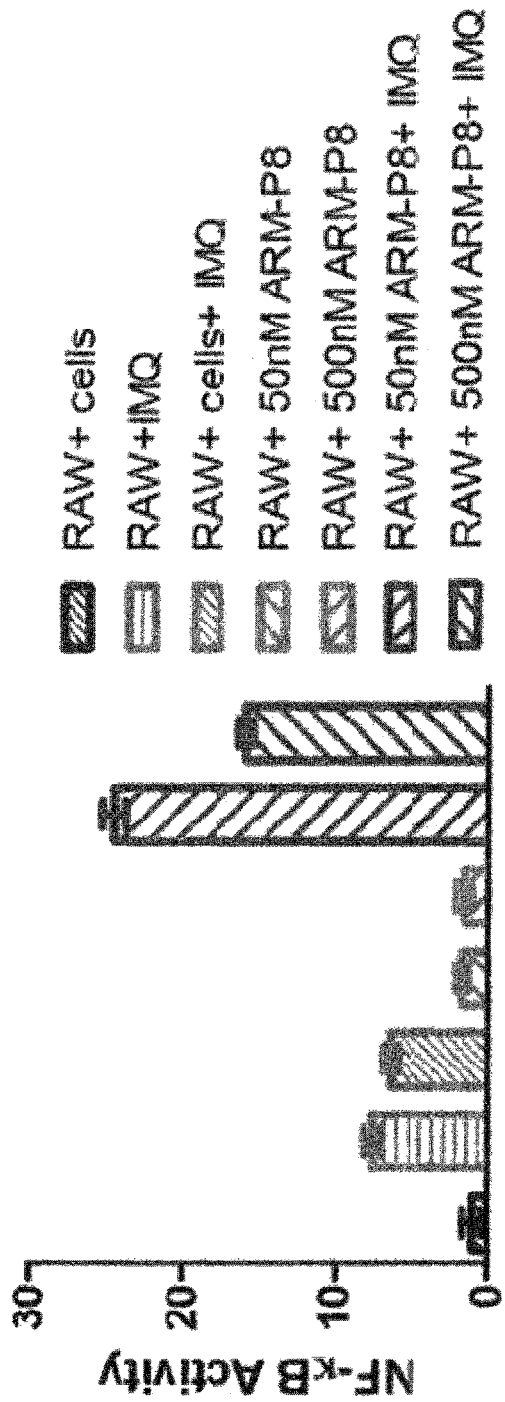

FIG. 9 shows phagocytosis of ARM-P8 opsonized tumor cells synergizes with soluble imiquimod (IMQ, 1 uM) for activation of NF-κB. Phagocytosis alone induces minimal NF-κB activation. PSMA expressing target cells were incubated with RAW macrophages transfected with an NF-κB luciferase reporter construct. NF-κB transcriptional activity was measured by luminescence read-out after 22 hrs by addition of the luciferase substrate coelanterazine. Values were normalized to luminescence produced by unstimulated RAW cells. Phagocytosis of targets via ARM-P8 and TLR7/8 agonism causes a synergistic (3-4× increase) in NF-κB activity.

Figure 10:
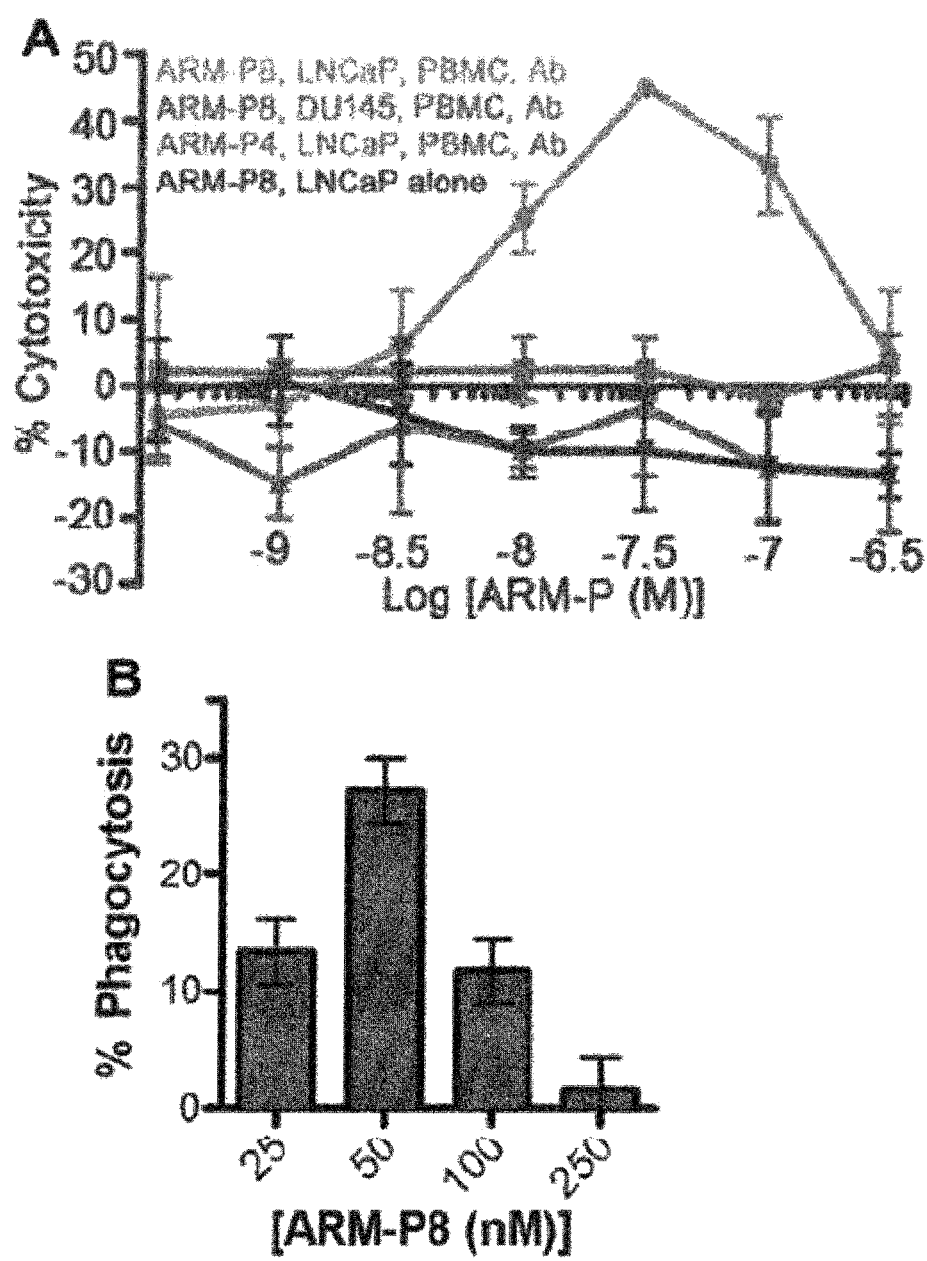
Figure 10:
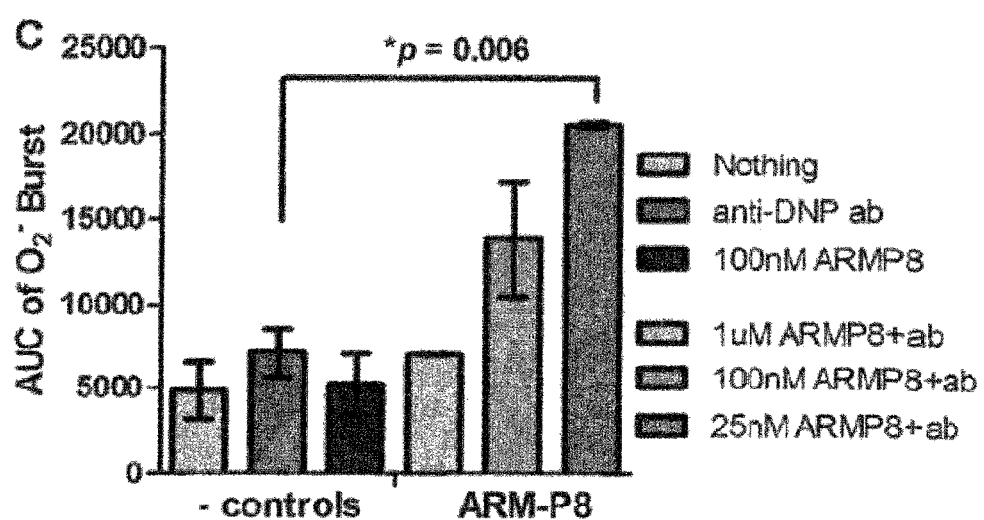

FIG. 10 A. shows the results of an antibody dependent cellular cytotoxicity assay which demonstrates targeted prostate cancer cell lysis in the presence of ARM-P8 and anti-DNP antibodies. Lncap (PSMA+) and DU145 (PSMA-) were incubated with human PBMCs and the indicated concentration of ARM-P8 with or without anti-DNP antibodies (Ab, 24 ug/ml). The bell-shaped curve is typical of a 3-component ternary complex system. B. Antibody dependent cellular phagocytosis assay also shows targeted action of ARM-P8 on PSMA expressing RMI.PGLS cells. 48 hr IFN-γ primed U937 L cells were used as effector cells. C. Superoxide production in IFN-γ primed U937 cells is dependent upon ARM-P8 and anti-DNP antibody opsonization of PSMA expressing PC3-PSMA cells. O2- amount is monitored over 90 min by reaction of luminol to generate luminescence.

Figure 11:
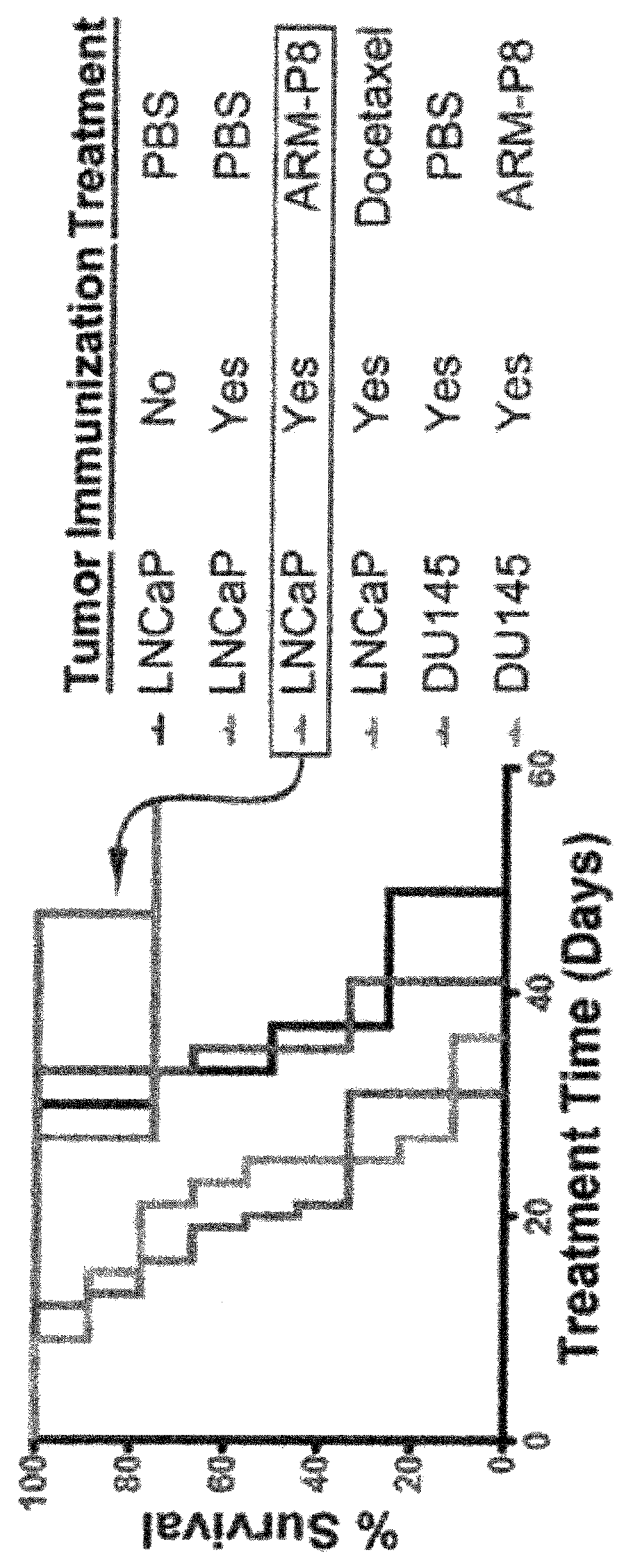

FIG. 11 shows data from prostate cancer xenograft studies demonstrating in vivo efficacy of ARM-P8 on athymic NCr-nu/nu mice. Mice were grafted PSMA+LNCaP or PSMA-DU145 tumors and immunized with DNP-ficoll to generate anti-DNP antibodies. Mice were then treated with ARM-P8, performed to determine serum docetaxel, or PBS. Mice in the LNCaP group responded to treatment with ARM-P8, and efficacy was comparable to docetaxel. Treatment of DU145 tumors with ARM-P8 showed no increase in lifespan compared with PBS.

Figure 12:
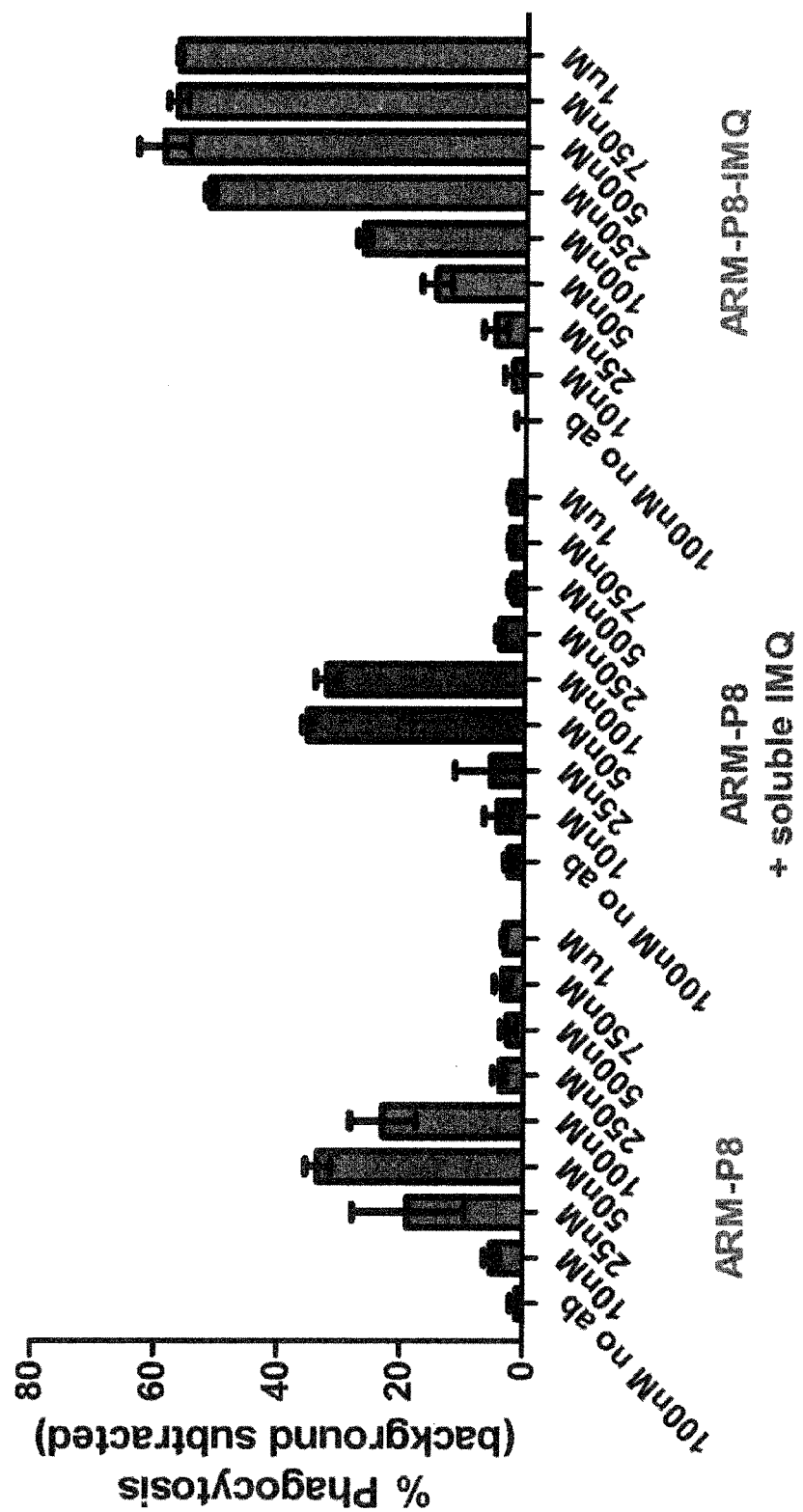

FIG. 12 shows that ARM-P8-IMQ enhances phagocytosis. A preferred molecule of the present invention, ARM-P8-IMQ, shows decreased potency (peak of the ternary complex ~500 nM instead of 50 nM for ARM-P8), but substantially increases increases the maximum phagocytosis of PSMA+ target cells from 35% to 60%.

Figure 13:
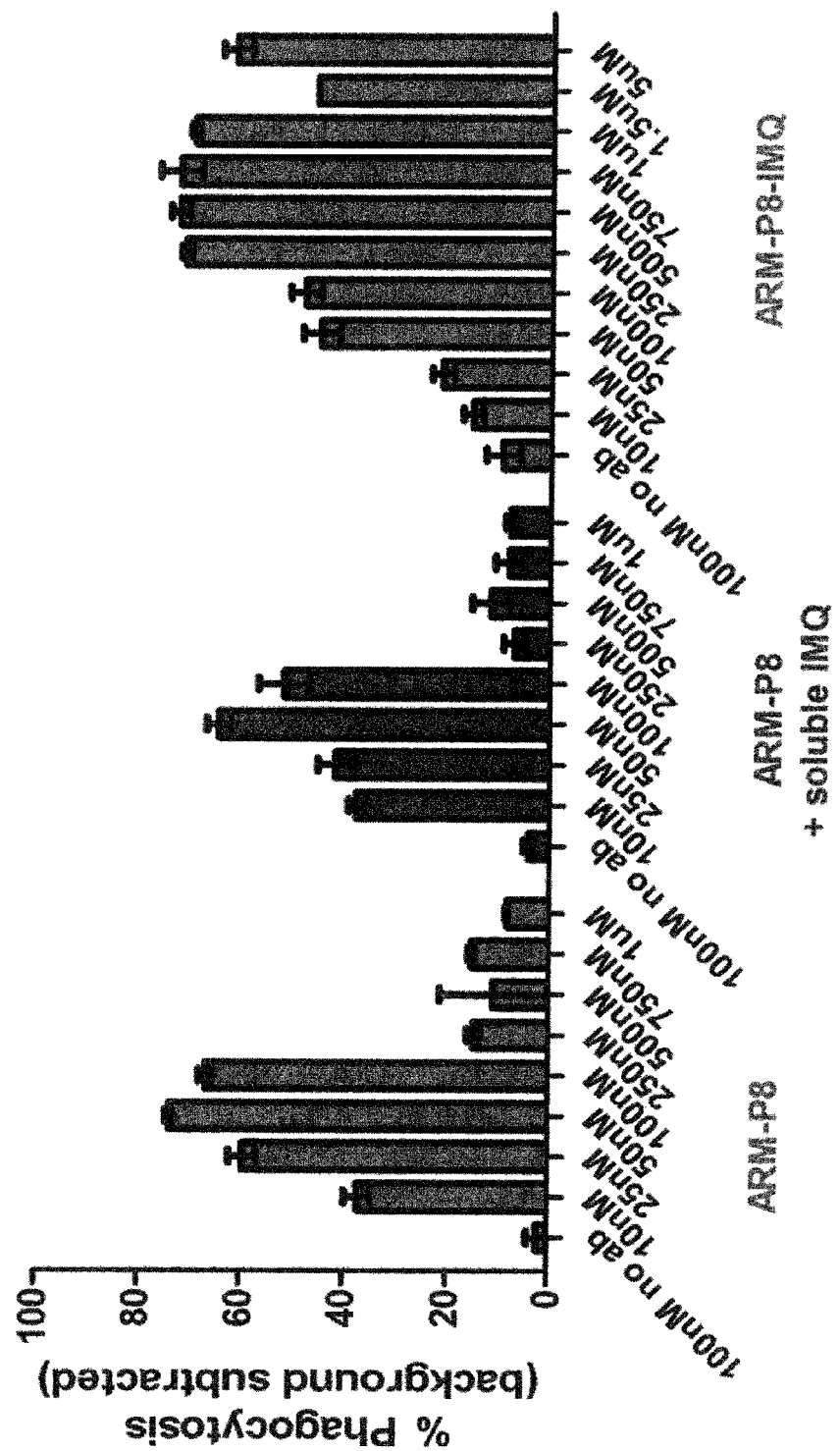
Figure 13:
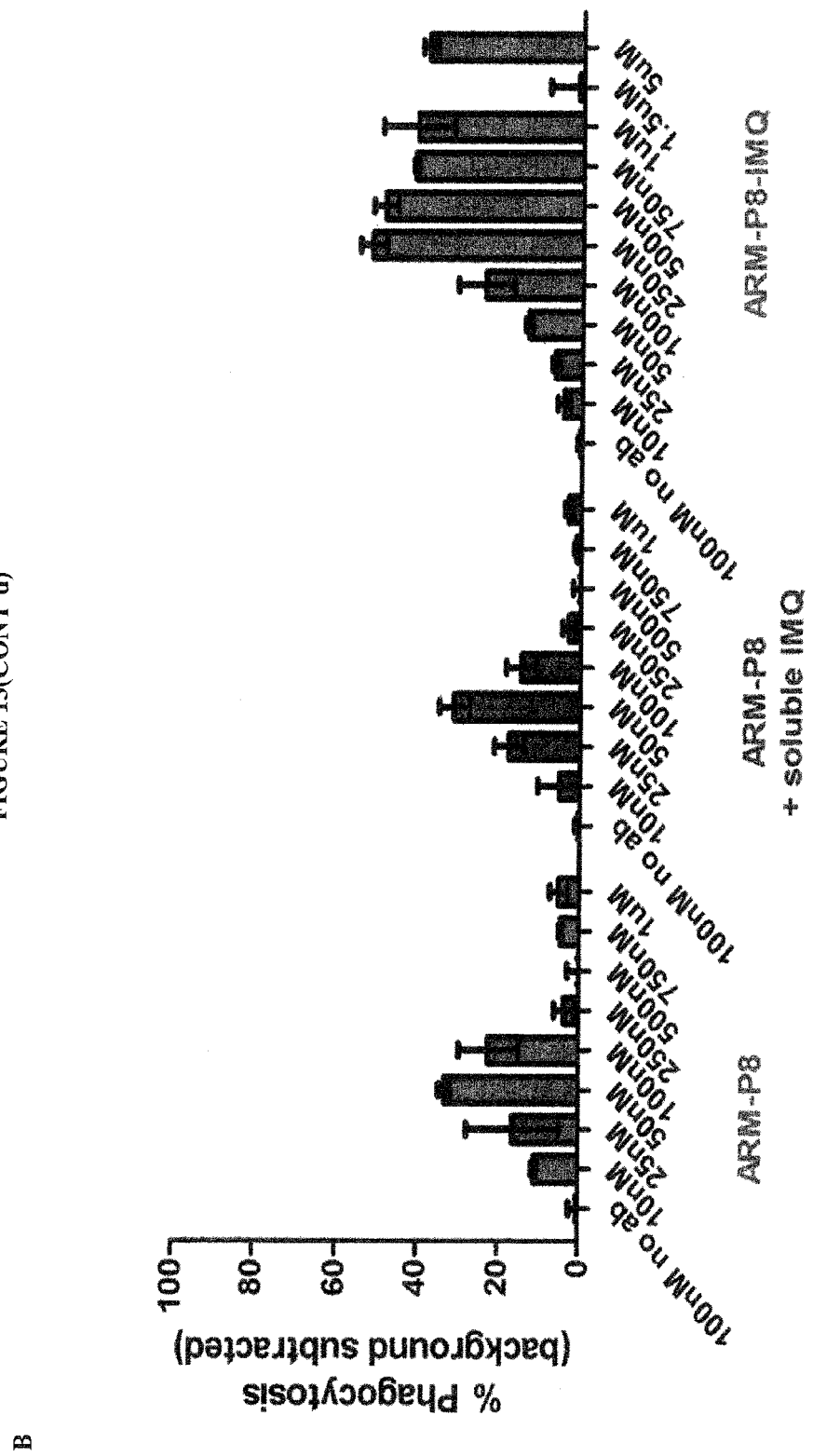

FIGS. 13A and B. This figure shows the effects of ARM-P8, ARM-P8 with soluble imiquimod and ARM-P8-IMQ on phagocytosis as a function of time. A shows no difference at 15 minutes, and B shows the same enhancement of phagocytosis with ARM-P8-IMQ at 1 hour. ARM-P8 is shows considerably lower phagocytosis at 1 hour as does ARM-P8 with soluble imiquimod.

Figure 14:
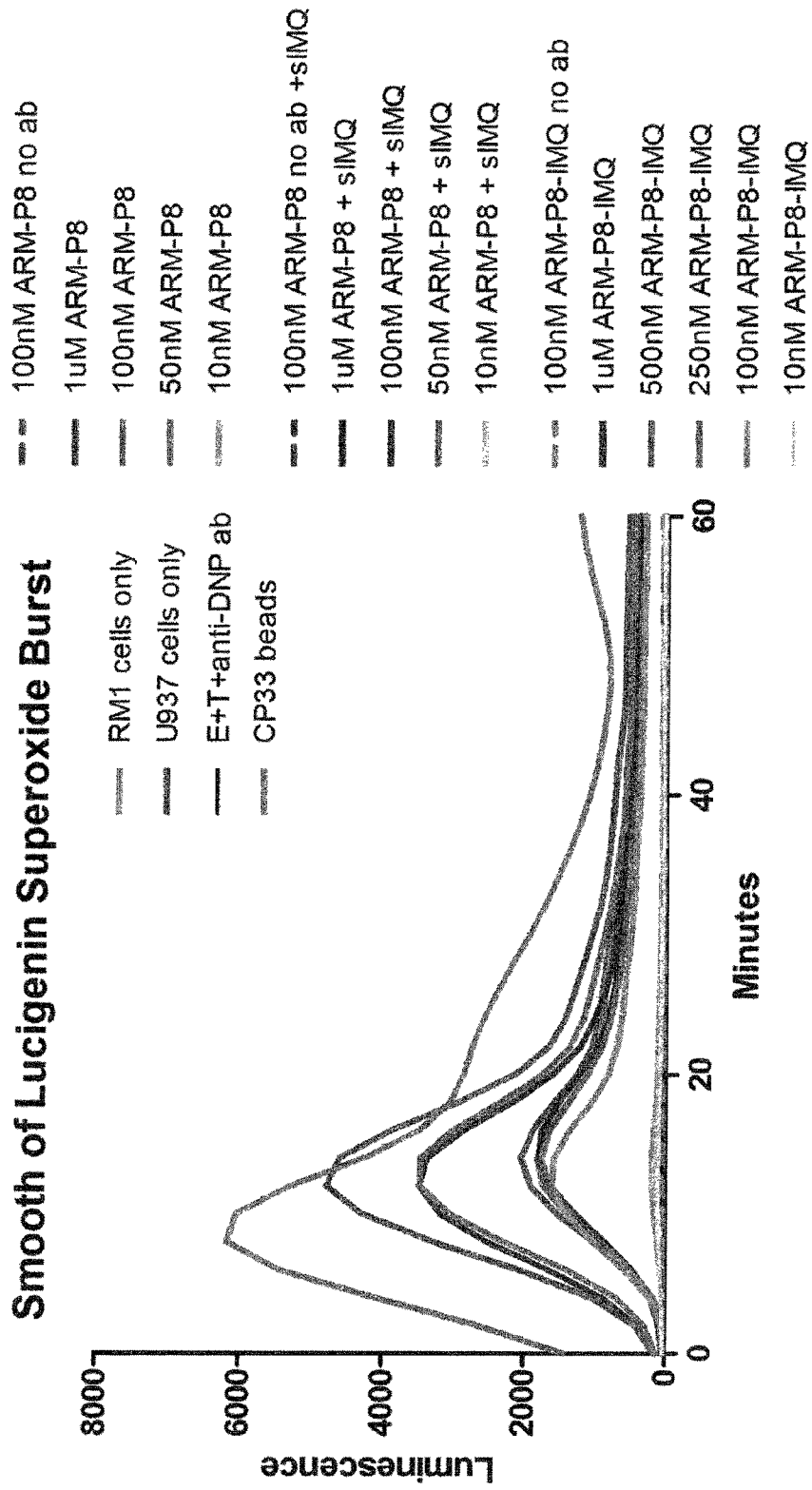

FIG. 14 shows that ARM-P8-IMQ increases $O_2$— production in cells.

Figure 15:
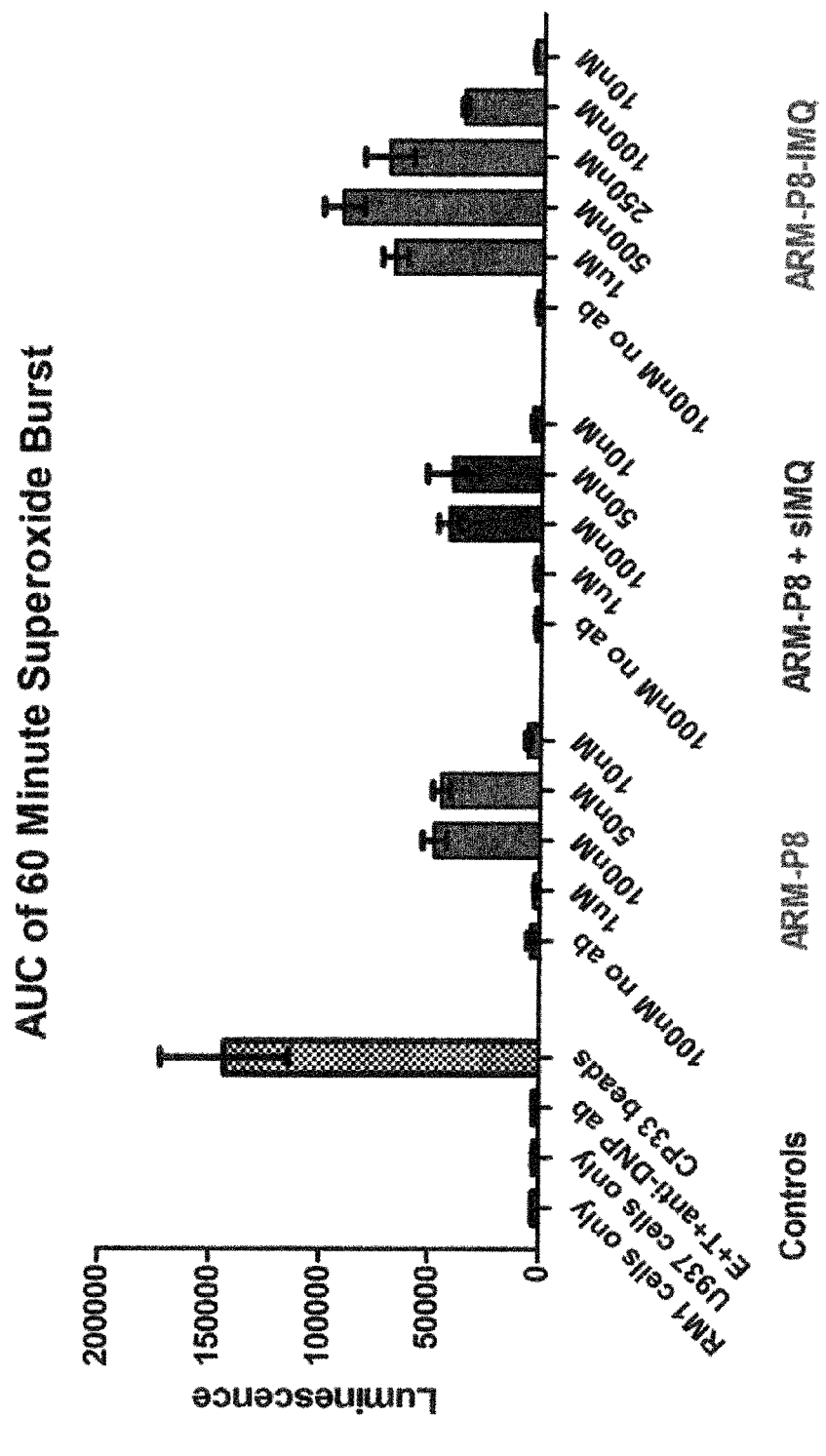
Figure 15:
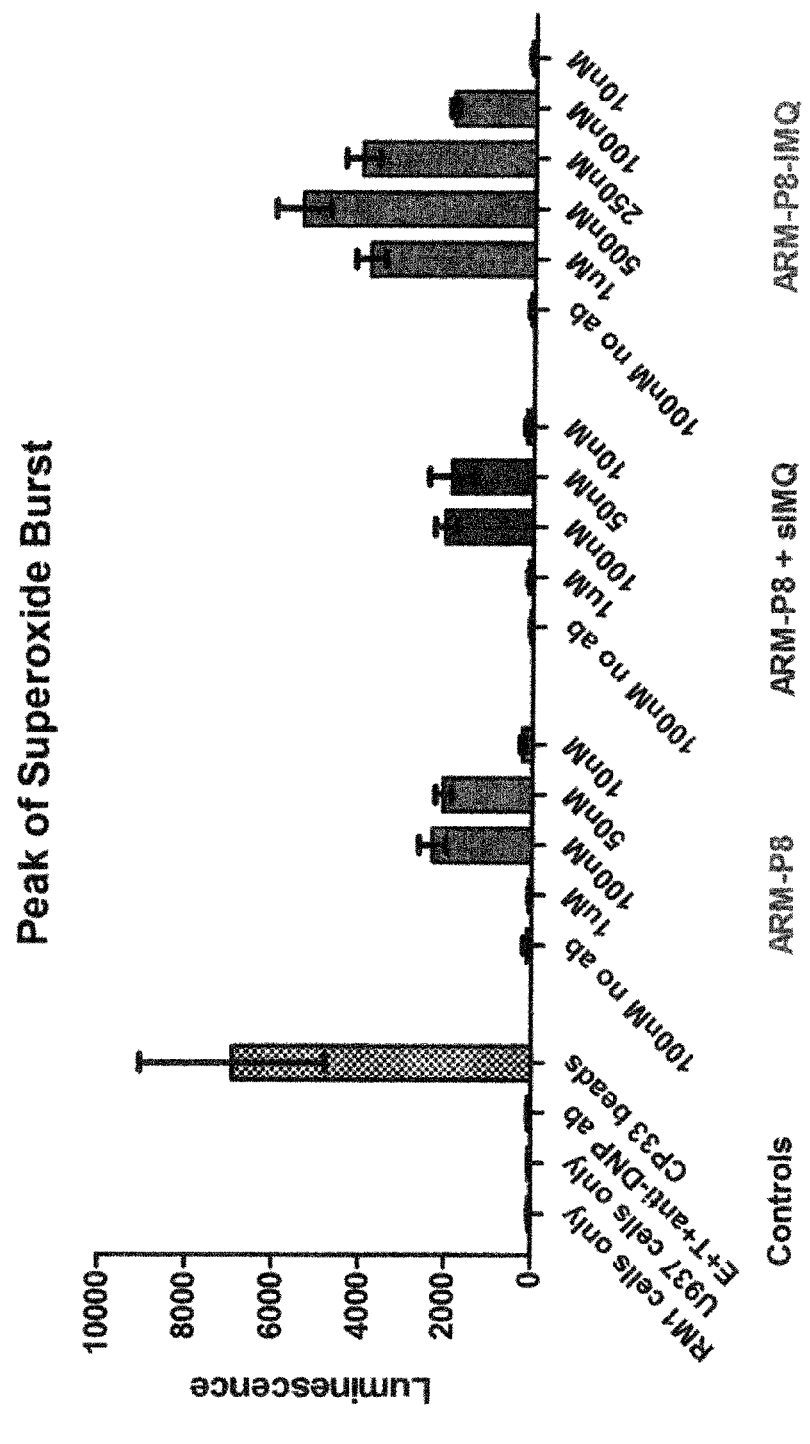

FIG. 15 shows the AUC of superoxide burst for ARM-P8, ARM-P8 with liquid imiquimod and with ARM-P*-IMQ. Similar to phagocytosis assay, ARM-P8-IMQ induces a more robust response than ARM-P8 at very short time points. A. Shows AUC of 60 minute superoxide burst. B shows the peak of superoxide burst.

Figure 16:
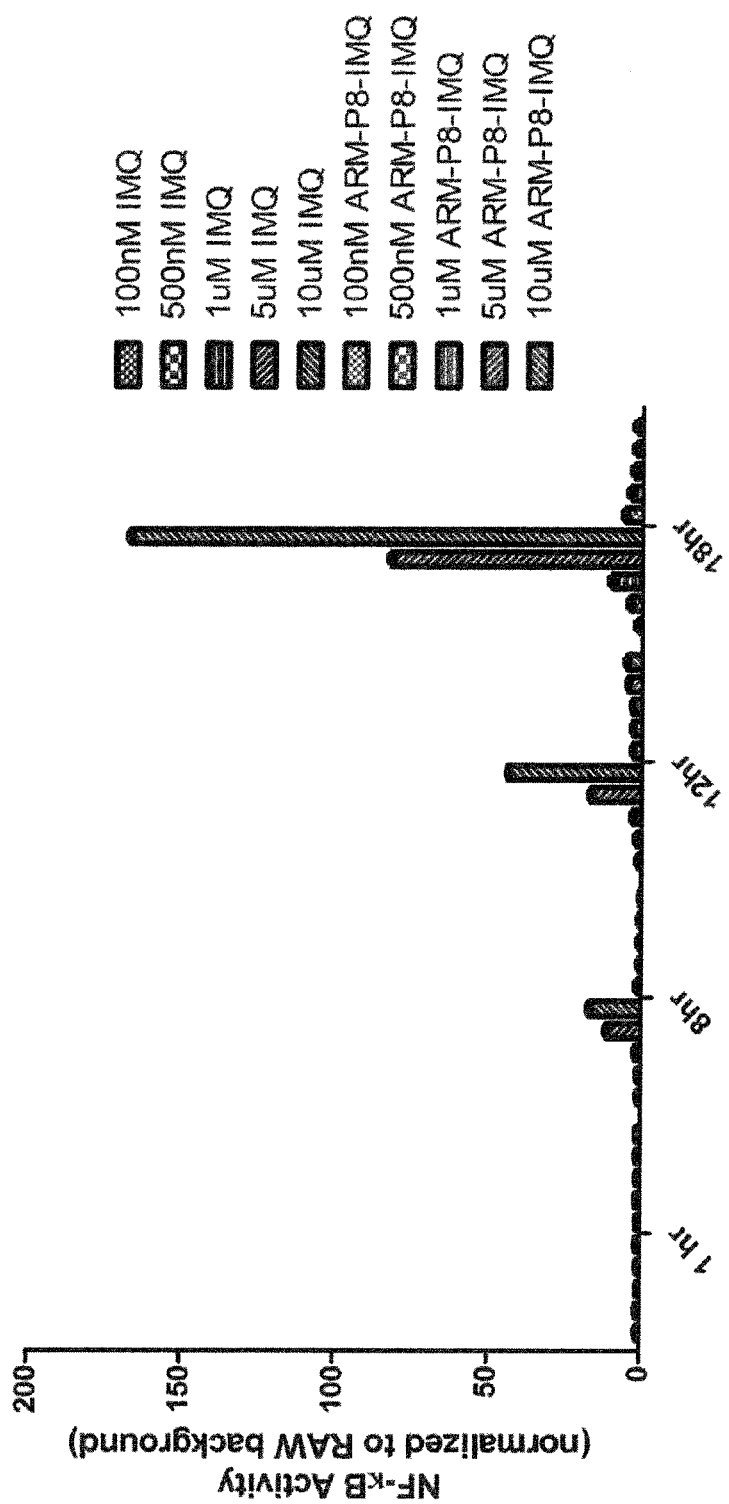

FIG. 16 shows that the activity of ARM-P8-IMQ is targeted. Compared to soluble imiquimod, ARM-P8-IMQ does not stimulate NF-κB activity when target cells and anti-DNP antibodies are absent.

Figure 17:
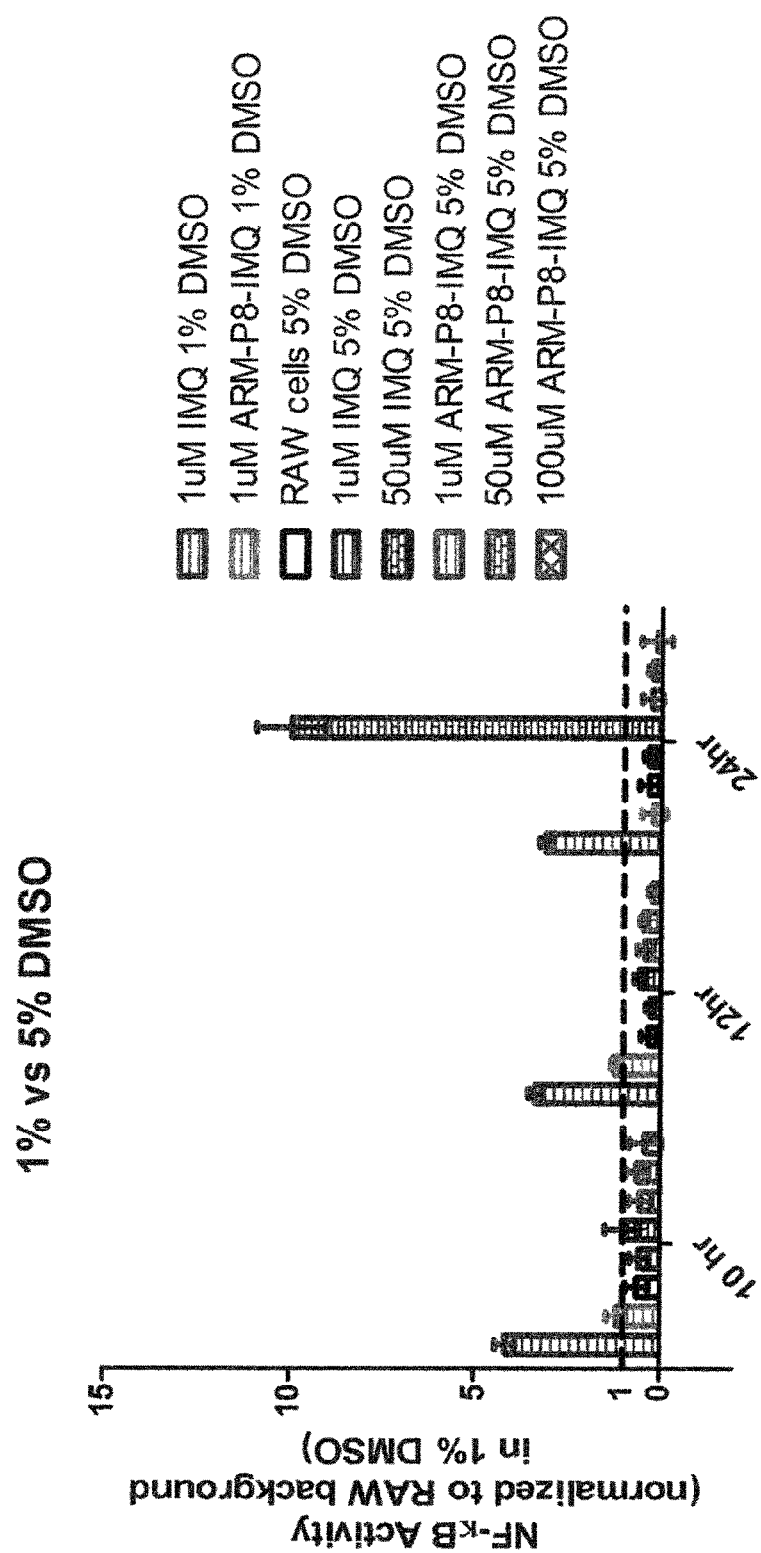

FIG. 17 shows the results of related NFκB assays. Two possibilities emerge for the results obtained: 1.) That ARM-P8-IMQ is not able to enter cell as well as imiquimod or 2.) ARM-P8-IMQ binds TLR7/8 with much reduced potency compared to imiquimod.

OBJECTS OF THE INVENTION

It is an object of the invention to provide trifunctional chimeric compounds which can be used to treat virtually any cancer, especially including prostate cancer and metastatic prostate cancer.

It is an additional object of the invention to provide trifunctional chimeric compounds which can be used to provide pharmaceutical compositions, including pharmaceutical compositions which include additional bioactive agents or agents which assist in the treatment of cancer, especially prostate cancer, including metastatic prostate cancer.

It is still another object of the invention to provide methods for treating cancer, including prostate cancer, including metastatic prostate cancer using trifunctional chimeric compounds exhibiting unexpected and synergistic anticancer activity.

Yet a further object of the invention is to provide methods for inhibiting metastatis of cancer, especially including metastatic prostate cancer.

It an additional object of the invention to provide trifunctional chimeric compounds which contain functional moieties which bind to PSMA, attract endogenous antibodies and provide immunological benefits of TLR agonists which act in a synergistic manner to enhance therapies against cancer, including prostate cancer and metastatic prostate cancer.

These and/or other objects of the invention may be readily gleaned from a review of the invention as described herein.

BRIEF DESCRIPTION OF THE INVENTION

It is an aspect of the invention to provide trifunctional chimeric antibody recruiting molecules which bind to prostate specific membrane antigen (PMSA), attract endogenous antibodies and contain TLR (e.g. TLR 7/8) agonists such that theses three functional groups will act in a synergistic manner to assist in immunotherapy of a patient with virtually any cancer, especially including prostate cancer, and further including metastatic prostate cancer.

In this first aspect of the invention, trifunctional chimeric antibody recruiting molecules are represented by the formula:

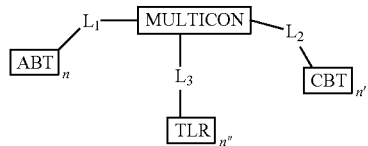

Wherein [ABT] is an antibody binding moiety (antibody binding terminus) comprising a hapten which is capable of binding to an antibody in a patient;

[CBT] is a cell binding moiety (cell binding terminus) capable of binding to prostate specific membrane antigen (PSMA) on the cell surface of cells, especially cancer cells such as prostate cancer cells in said patient;

[TLR] is a Toll-like Receptor (preferably, a TLR 7/8) agonist moiety;

$L_1$ is a linker group which links [MULTICON] to [ABT] in a molecule;

$L_2$ is a linker group which links [MULTICON] to [CBT] in a molecule;

$L_3$ is a linker group which binds [MULTICON] to [TLR] in a molecule;

Wherein any one or more of $L_1$, $L_2$ and $L_3$ optionally is or comprises a labile linker, preferably in proximity to [TLR];

[MULTICON] is a multifunctional connector molecule or group containing at least three functional groups which bind to said $L_1$, $L_2$ and $L_3$ linker groups, and Each n, n' and n" in a molecule is independently an integer from 1 to 15, 1 to 10, 1 to 5, 1 to 3, 2 to 3, 2 to 5, (preferably 1 or 2, preferably 1), or a pharmaceutically acceptable salt, stereoisomer, enantiomer, diastereomer, solvate or polymorph thereof.

In certain aspects of the invention, one or more of $L_1$, $L_2$ or $L_3$ in a molecule may be more than 1 (e.g. each of $L_1$, $L_2$ and $L_3$ may be up to 10 linkers, preferably up to 6 linkers, more preferably no more than 2 linkers, with each linker being bound to the multifunctional group and to one or more ABT, CBT or TLR moieties/groups). Most often, $L_1$, $L_2$ and $L_3$ are each 1 and n, n' and n" are each 1. In such instances, compounds according to the present invention may also be represented by the structure:

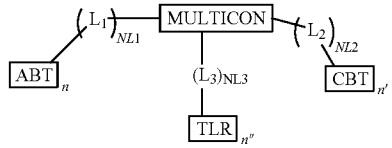

Where [ABT], [CBT], [TLR], $L_1$, $L_2$, $L_3$, n, n', n" and [MULTICON] are the same as above and each of NL1, NL2 and NL3 is an integer from 1 to 10, often 1 to 5, often 1 or 2, most often 1, with the proviso that n≥NL1, n' is ≥NL2 and n" is ≥NL3, or a pharmaceutically acceptable salt, stereoisomer, enantiomer, diastereomer, solvate or polymorph thereof.

In an additional aspect of the invention, a pharmaceutical composition comprises an effective amount of a trifunctional chimeric compound as described above, optionally and preferably in combination with a pharmaceutically acceptable carrier, additive or excipient. In alternative aspects, pharmaceutical combination compositions comprise an effective amount of at least one trifunctional chimeric compound as described herein, in combination with at least one additional agent which is used to treat cancer, including prostate cancer, especially including metastatic prostate cancer or a secondary condition or effect of cancer, especially prostate cancer (e.g., bone pain, hyperplasia, osteoporosis, etc. as otherwise described herein).

In a further aspect of the invention, compounds according to the present invention are used to treat and/or reduce the likelihood cancer in a patient, especially prostate cancer in male patients in need thereof and to treat or reduce the likelihood that a cancer, especially prostate cancer, will metastasize or that a cancer in remission will reoccur. The method of treating cancer comprises administering to a patient in need an effective amount of a trifunctional chimeric compound as otherwise described herein in combination with a pharmaceutically acceptable carrier, additive or excipient, optionally in further combination with at least one additional agent which is effective in treating cancer, especially including prostate cancer, metastatic cancer or one or more of its secondary conditions or effects.

The present invention also relates to a method for inhibiting prostate cancer to reduce or inhibit the spread or metastasis of the cancer into other tissues of the patients' body, especially including bones, the lymph (lymph nodes) system, bladder, vas deferens, kidneys, liver, lungs and brain, among others.

The present invention also relates to instances in which destruction of non-cancerous cells which possess PSMA can be of therapeutic use, especially in cancer therapy. For example, given that PSMA is found on the neovasculare of many non-prostatic cancer cells, but not on normal vasculature, the invention could be used for antiangiogenic therapy for other forms of cancer by targeting the neovasculature of those cancers and inhibiting the growth and spread of the cancer.

DETAILED DESCRIPTION OF THE INVENTION

The following terms are used to describe the present invention. In instances where a term is not specifically defined herein, that term is given an art-recognized meaning by those of ordinary skill applying that term in context to its use in describing the present invention.

The term "compound", as used herein, unless otherwise indicated, refers to any specific chemical compound, preferably TLR-ARMs disclosed herein and includes tautomers, regioisomers, geometric isomers, and where applicable, optical isomers (enantiomers) thereof, as well as pharmaceutically acceptable salts and derivatives (including prodrug forms) thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents, linkers and connector molecules and variables associated with same, among others, are described. It is understood by those of ordinary skill that molecules which are described herein are stable compounds as generally described hereunder.

The term "patient" or "subject" is used throughout the specification within context to describe an animal, generally a mammal and preferably a human, to whom treatment, including prophylactic treatment (prophylaxis), with the compositions according to the present invention is provided. For treatment of those infections, conditions or disease states which are specific for a specific animal such as a human patient or a patient of a particular gender, such as a human male patient, the term patient refers to that specific animal. Compounds according to the present invention are useful for the treatment of cancer, especially including prostate cancer and in particular, metastatic prostate cancer.

The term "effective" is used herein, unless otherwise indicated, to describe an amount of a compound or composition (most often, TLR-ARMs) which, in context, is used to produce or effect an intended result, whether that result relates to the inhibition of cancer, including metastatic cancer, especially prostate cancer or the treatment of a subject for secondary conditions, disease states or manifestations of cancer as otherwise described herein. This term subsumes all other effective amount or effective concentration terms (including the term "therapeutically effective") which are otherwise described in the present application.

The terms "treat", "treating", and "treatment", etc., as used herein, refer to any action providing a benefit to a patient at risk for cancer, especially prostate cancer or metastasis of prostate cancer, including improvement in the condition through lessening or suppression of at least one symptom, inhibition of cancer growth, reduction in cancer cells or tissue, prevention or delay in progression of metastasis of the cancer, prevention or delay in the onset of disease states or conditions which occur secondary to cancer or remission or cure of the cancer, among others. Treatment, as used herein, encompasses both prophylactic and therapeutic treatment. The term "prophylactic" when used, means to reduce the likelihood of an occurrence or the severity of an occurrence within the context of the treatment of cancer, including cancer metastasis as otherwise described hereinabove.

The term "neoplasia" refers to the uncontrolled and progressive multiplication of tumor cells, under conditions that would not elicit, or would cause cessation of, multiplication of normal cells. Neoplasia results in a "neoplasm", which is defined herein to mean any new and abnormal growth, particularly a new growth of tissue, in which the growth of cells is uncontrolled and progressive. Thus, neoplasia includes "cancer", which herein refers to a proliferation of tumor cells having the unique trait of loss of normal controls, resulting in unregulated growth, lack of differentiation, local tissue invasion, and/or metastasis.

As used herein, neoplasms include, without limitation, morphological irregularities in cells in tissue of a subject or host, as well as pathologic proliferation of cells in tissue of a subject, as compared with normal proliferation in the same type of tissue. Additionally, neoplasms include benign tumors and malignant tumors (e.g., colon tumors) that are either invasive or noninvasive. Malignant neoplasms are distinguished from benign neoplasms in that the former show a greater degree of anaplasia, or loss of differentiation and orientation of cells, and have the properties of invasion and metastasis. Examples of neoplasms or neoplasias from which the target cell of the present invention may be derived include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas, which may be treated by one or more compounds according to the present invention. See, (Beers and Berkow (eds.), The Merck Manual of Diagnosis and Therapy, 17.sup.th ed. (Whitehouse Station, N.J.: Merck Research Laboratories, 1999) 973-74, 976, 986, 988, 991.

Because of the activity of the present compounds as anti-angiogenic compounds, the present invention has general applicability treating virtually any cancer in any tissue, thus the compounds, compositions and methods of the present invention are generally applicable to the treatment of cancer. Given that the protein target is found on the neovasculature of most non-prostatic cancer cells, the compounds in the present invention may also serve as an antiangiogenic therapy for other cancer types.

In certain particular aspects of the present invention, the cancer which is treated is prostate cancer or metastatic prostate cancer. Separately, metastatic prostate cancer may be found in virtually all tissues of a cancer patient in late stages of the disease, typically metastatic prostate cancer is found in seminal vesicles, lymph system/nodes (lymphoma), in bones, in bladder tissue, in kidney tissue, liver tissue and in virtually any tissue, including brain (brain cancer/tumor). Thus, the present invention is generally applicable and may be used to treat any cancer in any tissue, regardless of etiology.

The term "prostate cancer" is used to describe a disease in which cancer develops in the prostate, a gland in the male reproductive system. It occurs when cells of the prostate mutate and begin to multiply uncontrollably. These cells may metastasize (metastatic prostate cancer) from the prostate to virtually any other part of the body, particularly the bones and lymph nodes, but the kidney, bladder and even the brain, among other tissues. Prostate cancer may cause pain, difficulty in urinating, problems during sexual intercourse, erectile dysfunction. Other symptoms can potentially develop during later stages of the disease.

Rates of detection of prostate cancers vary widely across the world, with South and East Asia detecting less frequently than in Europe, and especially the United States. Prostate cancer develops most frequently in men over the age of fifty and is one of the most prevalent types of cancer in men. However, many men who develop prostate cancer never have symptoms, undergo no therapy, and eventually die of other causes. This is because cancer of the prostate is, in most cases, slow-growing, and because most of those affected are over the age of 60. Hence, they often die of causes unrelated to the prostate cancer. Many factors, including genetics and diet, have been implicated in the development of prostate cancer. The presence of prostate cancer may be indicated by symptoms, physical examination, prostate specific antigen (PSA), or biopsy. There is concern about the accuracy of the PSA test and its usefulness in screening. Suspected prostate cancer is typically confirmed by taking a biopsy of the prostate and examining it under a microscope. Further tests, such as CT scans and bone scans, may be performed to determine whether prostate cancer has spread.

Treatment options for prostate cancer with intent to cure are primarily surgery and radiation therapy. Other treatments such as hormonal therapy, chemotherapy, proton therapy, cryosurgery, high intensity focused ultrasound (HIFU) also exist depending on the clinical scenario and desired outcome. The present invention may be used to enhance any one or more of these therapies or to supplant them.

The age and underlying health of the man, the extent of metastasis, appearance under the microscope, and response of the cancer to initial treatment are important in determining the outcome of the disease. The decision whether or not to treat localized prostate cancer (a tumor that is contained within the prostate) with curative intent is a patient trade-off between the expected beneficial and harmful effects in terms of patient survival and quality of life.

An important part of evaluating prostate cancer is determining the stage, or how far the cancer has spread. Knowing the stage helps define prognosis and is useful when selecting therapies. The most common system is the four-stage TNM system (abbreviated from Tumor/Nodes/Metastases). Its components include the size of the tumor, the number of involved lymph nodes, and the presence of any other metastases.

The most important distinction made by any staging system is whether or not the cancer is still confined to the prostate or is metastatic. In the TNM system, clinical T1 and T2 cancers are found only in the prostate, while T3 and T4 cancers have spread elsewhere and metastasized into other tissue. Several tests can be used to look for evidence of spread. These include computed tomography to evaluate spread within the pelvis, bone scans to look for spread to the bones, and endorectal coil magnetic resonance imaging to closely evaluate the prostatic capsule and the seminal vesicles. Bone scans often reveal osteoblastic appearance due to increased bone density in the areas of bone metastasis—opposite to what is found in many other cancers that metastasize. Computed tomography (CT) and magnetic resonance imaging (MRI) currently do not add any significant information in the assessment of possible lymph node metastases in patients with prostate cancer according to a meta-analysis.

Prostate cancer is relatively easy to treat if found early. After a prostate biopsy, a pathologist looks at the samples under a microscope. If cancer is present, the pathologist reports the grade of the tumor. The grade tells how much the tumor tissue differs from normal prostate tissue and suggests how fast the tumor is likely to grow. The Gleason system is used to grade prostate tumors from 2 to 10, where a Gleason score of 10 indicates the most abnormalities. The pathologist assigns a number from 1 to 5 for the most common pattern observed under the microscope, then does the same for the second most common pattern. The sum of these two numbers is the Gleason score. The Whitmore-Jewett stage is another method sometimes used. Proper grading of the tumor is critical, since the grade of the tumor is one of the major factors used to determine the treatment recommendation.

Early prostate cancer usually causes no symptoms. Often it is diagnosed during the workup for an elevated PSA noticed during a routine checkup. Sometimes, however, prostate cancer does cause symptoms, often similar to those of diseases such as benign prostatic hypertrophy. These include frequent urination, increased urination at night, difficulty starting and maintaining a steady stream of urine, blood in the urine, and painful urination. Prostate cancer is associated with urinary dysfunction as the prostate gland surrounds the prostatic urethra. Changes within the gland therefore directly affect urinary function. Because the vas deferens deposits seminal fluid into the prostatic urethra, and secretions from the prostate gland itself are included in semen content, prostate cancer may also cause problems with sexual function and performance, such as difficulty achieving erection or painful ejaculation.

Advanced prostate cancer can spread to other parts of the body and this may cause additional symptoms. The most common symptom is bone pain, often in the vertebrae (bones of the spine), pelvis or ribs. Spread of cancer into other bones such as the femur is usually to the proximal part of the bone. Prostate cancer in the spine can also compress the spinal cord, causing leg weakness and urinary and fecal incontinence.

The specific causes of prostate cancer remain unknown. A man's risk of developing prostate cancer is related to his age, genetics, race, diet, lifestyle, medications, and other factors. The primary risk factor is age. Prostate cancer is uncommon in men less than 45, but becomes more common with advancing age. The average age at the time of diagnosis is 70. However, many men never know they have prostate cancer.

A man's genetic background contributes to his risk of developing prostate cancer. This is suggested by an increased incidence of prostate cancer found in certain racial groups, in identical twins of men with prostate cancer, and in men with certain genes. Men who have a brother or father with prostate cancer have twice the usual risk of developing prostate cancer. Studies of twins in Scandinavia suggest that forty percent of prostate cancer risk can be explained by inherited factors. However, no single gene is responsible for prostate cancer; many different genes have been implicated. Two genes (BRCA1 and BRCA2) that are important risk factors for ovarian cancer and breast cancer in women have also been implicated in prostate cancer.

Dietary amounts of certain foods, vitamins, and minerals can contribute to prostate cancer risk. Dietary factors that may increase prostate cancer risk include low intake of vitamin E, the mineral selenium, green tea and vitamin D. A large study has implicated dairy, specifically low-fat milk and other dairy products to which vitamin A palmitate has been added. This form of synthetic vitamin A has been linked to prostate cancer because it reacts with zinc and protein to form an unabsorbable complex. Prostate cancer has also been linked to the inclusion of bovine somatotropin hormone in certain dairy products.

There are also some links between prostate cancer and medications, medical procedures, and medical conditions. Daily use of anti-inflammatory medicines such as aspirin, ibuprofen, or naproxen may decrease prostate cancer risk. Use of the cholesterol-lowering drugs known as the statins may also decrease prostate cancer risk. Infection or inflammation of the prostate (prostatitis) may increase the chance for prostate cancer, and infection with the sexually transmitted infections chlamydia, gonorrhea, or syphilis seems to increase risk. Obesity and elevated blood levels of testosterone may increase the risk for prostate cancer.

Prostate cancer is classified as an adenocarcinoma, or glandular cancer, that begins when normal semen-secreting prostate gland cells mutate into cancer cells. The region of prostate gland where the adenocarcinoma is most common is the peripheral zone. Initially, small clumps of cancer cells remain confined to otherwise normal prostate glands, a condition known as carcinoma in situ or prostatic intraepithelial neoplasia (PIN). Although there is no proof that PIN is a cancer precursor, it is closely associated with cancer. Over time these cancer cells begin to multiply and spread to the surrounding prostate tissue (the stroma) forming a tumor. Eventually, the tumor may grow large enough to invade nearby organs such as the seminal vesicles or the rectum, or the tumor cells may develop the ability to travel in the bloodstream and lymphatic system. Prostate cancer is considered a malignant tumor because it is a mass of cells which can invade other parts of the body. This invasion of other organs is called metastasis. Prostate cancer most commonly metastasizes to the bones, lymph nodes, rectum, and bladder.

In prostate cancer, the regular glands of the normal prostate are replaced by irregular glands and clumps of cells. When a man has symptoms of prostate cancer, or a screening test indicates an increased risk for cancer, more invasive evaluation is offered. The only test which can fully confirm the diagnosis of prostate cancer is a biopsy, the removal of small pieces of the prostate for microscopic examination. However, prior to a biopsy, several other tools may be used to gather more information about the prostate and the urinary tract. Cystoscopy shows the urinary tract from inside the bladder, using a thin, flexible camera tube inserted down the urethra. Transrectal ultrasonography creates a picture of the prostate using sound waves from a probe in the rectum.

After biopsy, the tissue samples are then examined under a microscope to determine whether cancer cells are present, and to evaluate the microscopic features (or Gleason score) of any cancer found. In addition, tissue samples may be stained for the presence of PSA and other tumor markers in order to determine the origin of malignant cells that have metastasized. A number of other potential approaches for diagnosis of prostate cancer are ongoing such as early prostate cancer antigen-2 (EPCA-2), and prostasome analysis.

In addition to therapy using the compounds according to the present invention, therapy (including prophylactic therapy) for prostate cancer supports roles in reducing prostate cancer for dietary selenium, vitamin E, lycopene, soy foods, vitamin D, green tea, omega-3 fatty acids and phytoestrogens. The selective estrogen receptor modulator drug toremifene has shown promise in early trials. Two medications which block the conversion of testosterone to dihydrotestosterone (and reduce the tendency toward cell growth), finasteride and dutasteride, are shown to be useful. The phytochemicals indole-3-carbinol and diindolylmethane, found in cruciferous vegetables (cauliflower and broccoli), have favorable antiandrogenic and immune modulating properties. Prostate cancer risk is decreased in a vegetarian diet.

Treatment for prostate cancer may involve active surveillance, surgery (prostatecomy or orchiectomy), radiation therapy including brachytherapy (prostate brachytherapy) and external beam radiation as well as hormonal therapy. There are several forms of hormonal therapy which include the following, each of which may be combined with compounds according to the present invention.

Antiandrogens such as flutamide, bicalutamide, nilutamide, and cyproterone acetate which directly block the actions of testosterone and DHT within prostate cancer cells.

Medications such as ketoconazole and aminoglutethimide which block the production of adrenal androgens such as DHEA. These medications are generally used only in combination with other methods that can block the 95% of androgens made by the testicles. These combined methods are called total androgen blockade (TAB), which can also be achieved using antiandrogens.

GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin.

The use of abiraterone acetate can be used to reduce PSA levels and tumor sizes in aggressive end-stage prostate cancer for as high as 70% of patients. Sorafenib may also be used to treat metastatic prostate cancer.

Each treatment described above has disadvantages which limit its use in certain circumstances. GnRH agonists eventually cause the same side effects as orchiectomy but may cause worse symptoms at the beginning of treatment. When GnRH agonists are first used, testosterone surges can lead to increased bone pain from metastatic cancer, so antiandrogens or abarelix are often added to blunt these side effects. Estrogens are not commonly used because they increase the risk for cardiovascular disease and blood clots. The antiandrogens do not generally cause impotence and usually cause less loss of bone and muscle mass. Ketoconazole can cause liver damage with prolonged use, and aminoglutethimide can cause skin rashes.

Palliative care for advanced stage prostate cancer focuses on extending life and relieving the symptoms of metastatic disease. As noted above, abiraterone acetate shows some promise in treating advance stage prostate cancer as does sorafenib. Chemotherapy may be offered to slow disease progression and postpone symptoms. The most commonly used regimen combines the chemotherapeutic drug docetaxel with a corticosteroid such as prednisone. Bisphosphonates such as zoledronic acid have been shown to delay skeletal complications such as fractures or the need for radiation therapy in patients with hormone refractory metastatic prostate cancer. Alpharadin may be used to target bone metastasis. The phase II testing shows prolonged patient survival times, reduced pain and improved quality of life.

Bone pain due to metastatic disease is treated with opioid pain relievers such as morphine and oxycodone. External beam radiation therapy directed at bone metastases may provide pain relief. Injections of certain radioisotopes, such as strontium-89, phosphorus-32, or samarium-153, also target bone metastases and may help relieve pain.

As an alternative to active surveillance or definitive treatments, alternative therapies may also be used for the management of prostate cancer. PSA has been shown to be lowered in men with apparent localized prostate cancer using a vegan diet (fish allowed), regular exercise, and stress reduction. Many other single agents have been shown to reduce PSA, slow PSA doubling times, or have similar effects on secondary markers in men with localized cancer in short term trials, such as pomegranate juice or genistein, an isoflavone found in various legumes.

Manifestations or secondary conditions or effects of metastatic and advanced prostate cancer may include anemia, bone marrow suppression, weight loss, pathologic fractures, spinal cord compression, pain, hematuria, ureteral and/or bladder outlet obstruction, urinary retention, chronic renal failure, urinary incontinence, and symptoms related to bony or soft-tissue metastases, among others.

Additional prostate drugs which can be used in combination with the chimeric antibody recruiting compounds according to the present invention include, for example, the enlarged prostate drugs/agents, as well as eulexin, flutamide, goserelin, leuprolide, lupron, nilandron, nilutamide, zoladex and mixtures thereof. Enlarged prostate drugs/agents as above, include for example, ambenyl, ambophen, amgenal, atrosept, bromanyl, bromodiphenhydramine-codeine, bromotuss-codeine, cardura, chlorpheniramine-hydrocodone, ciclopirox, clotrimazole-betamethasone, dolsed, dutasteride, finasteride, flomax, gecil, hexalol, lamisil, lanased, loprox, lotrisone, methenamine, methen-bella-meth Bl-phen sal, meth-hyos-atrp-M blue-BA-phsal, MHP-A, mybanil, prosed/DS, Ro-Sed, S-T Forte, tamsulosin, terbinafine, trac, tussionex, ty-methate, uramine, uratin, uretron, uridon, uroves, urstat, usept and mixtures thereof.

The term "tumor" is used to describe a malignant or benign growth or tumefacent.

The term "antibody binding terminal moiety", "antibody binding terminus", "antibody binding moiety" or [ABT] is use to described that portion of a chimeric compound according to the present invention which comprises at least one small molecule or hapten. The term "hapten" is used to describe a small-molecular-weight inorganic or organic molecule that alone is not antigenic but which when linked to another molecule, such as a carrier protein (albumin, etc.) or in the case of the present invention, a cell binding terminal moiety of the present compounds is antigenic; and an antibody raised against the hapten (generally, the hapten bonded or complexed to the carrier) will react with the hapten alone.

It is preferred that the antibody binding terminal comprise a hapten which is reactive (binds to) an endogenous antibody that pre-exists in the patient prior to initiating therapy with the compounds of the present invention and does not have to be separately raised as part of a treatment regimen. Thus, haptens which comprise a di- or trinitro phenyl group as depicted below, or a digalactose hapten (Gal-Gal-Z, preferably Gal-Gal-sugar, preferably Gal-Gal-Glu), are preferred. Additionally, a compound according to the general structure:

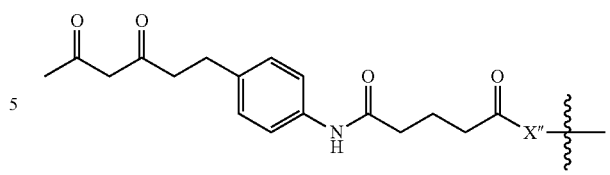

Where X" is O, $CH_2$, $NR^1$, S; and
$R^1$ is H, a $C_1$-$C_3$ alkyl group or a —C(O)($C_1$-$C_3$) group;
May be used as haptens in the present invention.
Further, a moiety according to the chemical structure:

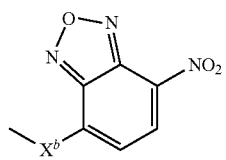

Where $X^b$ is a bond, O, $CH_2$, $NR^1$ or S may also be used as a hapten (ABT) in the present invention.
Other ABT moieties include the following/structures:

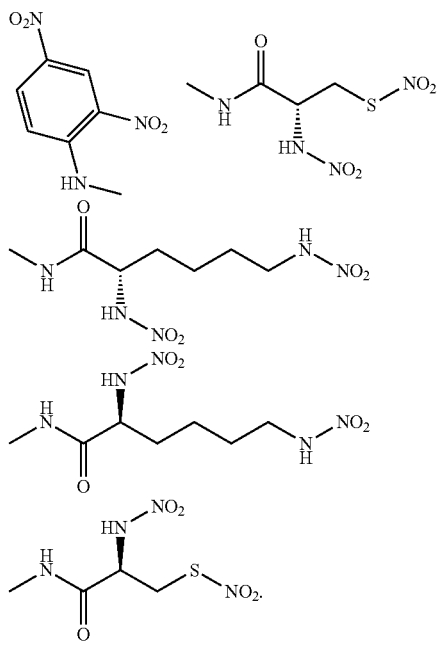

Each of the above amino acid ABT moieties may be further substituted with a dinitrophenyl group through an X group, e.g., $CH_2$—, sulfoxide, sulfone, etc. group as otherwise described herein to provide the following ABT moieties:

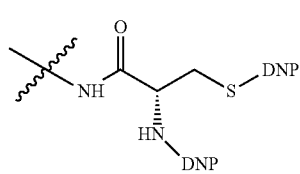

-continued

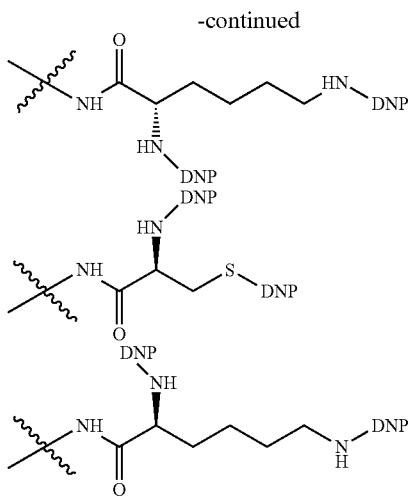

In the above structures in each of the molecules (with the exception of the first, which is DNP amine), DNP may be linked to the structure where the $NO_2$ is linked (i.e., DNP replaces the $NO_2$ group in the structure).

The di- or trinitro phenyl hapten (ABT) moiety for use in the present invention may be represented by the following formula:

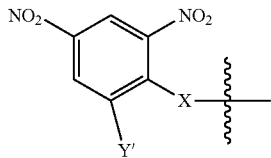

Where Y' is H or $NO_2$;
X is O, $CH_2$, $NR^1$, S(O), $S(O)_2$, —$S(O)_2O$, —$OS(O)_2$, or $OS(O)_2O$;
$R^1$ is H, a $C_1$-$C_3$ alkyl group, or a —$C(O)(C_1$-$C_3)$ group;

The (Gal-Gal-Z) hapten is represented by the chemical formula:

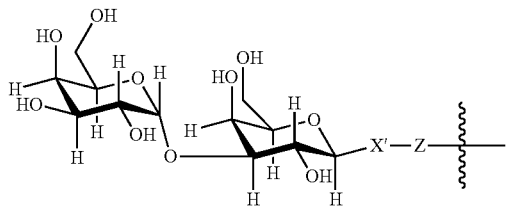

Where X' is $CH_2$, O, N—R'', or S, preferably O;
$R^{1'}$ is H or $C_1$-$C_3$ alkyl;
Where Z is a bond, a monosaccharide, disaccharide, oligosaccharide, glycoprotein or glycolipid, preferably a sugar group, more preferably a sugar group selected from the monosaccharides, including aldoses and ketoses, and disaccharides, including those disaccharides described herein. Monosaccharide aldoses include monosaccharides such as aldotriose (D-glyceraldehdye, among others), aldotetroses (D-erythrose and D-Threose, among others), aldopentoses (D-ribose, D-arabinose, D-xylose, D-lyxose, among others), aldohexoses (D-allose, D-altrose, D-Glucose, D-Mannose, D-gulose, D-idose, D-galactose, D-rhamnose and D-Talose, among others), and the monosaccharide ketoses include monosaccharides such as ketotriose (dihydroxyacetone, among others), ketotetrose (D-erythrulose, among others), ketopentose (D-ribulose and D-xylulose, among others), ketohexoses (D-Psicone, D-Fructose, D-Sorbose, D-Tagatose, among others), the 6-deoxyhexose sugar L-rhamnose (also set forth below), aminosugars, including galactoseamine, sialic acid, N-acetylglucosamine, among others and sulfosugars, including sulfoquinovose, among others. Exemplary disaccharides which find use in the present invention include sucrose (which may have the glucose optionally N-acetylated), lactose (which may have the galactose and/or the glucose optionally N-acetylated), maltose (which may have one or both of the glucose residues optionally N-acetylated), trehalose (which may have one or both of the glucose residues optionally N-acetylated), cellobiose (which may have one or both of the glucose residues optionally N-acetylated), kojibiose (which may have one or both of the glucose residues optionally N-acetylated), nigerose (which may have one or both of the glucose residues optionally N-acetylated), isomaltose (which may have one or both of the glucose residues optionally N-acetylated), β,β-trehalose (which may have one or both of the glucose residues optionally N-acetylated), sophorose (which may have one or both of the glucose residues optionally N-acetylated), laminaribiose (which may have one or both of the glucose residues optionally N-acetylated), gentiobiose (which may have one or both of the glucose residues optionally N-acetylated), turanose (which may have the glucose residue optionally N-acetylated), maltulose (which may have the glucose residue optionally N-acetylated), palatinose (which may have the glucose residue optionally N-acetylated), gentiobiluose (which may have the glucose residue optionally N-acetylated), mannobiose, melibiose (which may have the glucose residue and/or the galactose residue optionally N-acetylated), melibiulose (which may have the galactose residue optionally N-acetylated), rutinose, (which may have the glucose residue optionally N-acetylated), rutinulose and xylobiose, among others. Oligosaccharides for use in the present invention as Z can include any sugar of three or more (up to about 100) individual sugar (saccharide) units as described above (i.e., any one or more saccharide units described above, in any order, especially including glucose and/or galactose units as set forth above), or for example, fructo-oligosaccharides, galactooligosaccharides and mannan-oligosaccharides ranging from three to about ten-fifteen sugar units in size. Glycoproteins for use in the present invention include, for example, N-glycosylated and O-glycosylated glycoproteins, including the mucins, collagens, transferring, ceruloplasmin, major histocompatability complex proteins (MHC), enzymes, lectins and selectins, calnexin, calreticulin, and integrin glycoprotein IIb/IIa, among others. Glycolipids for use in the present invention include, for example, glyceroglycolipids (galactolipids, sulfolipids), glycosphingolipids, such as cerebrosides, galactocerebrosides, glucocerebrosides (including glucobicaranateoets), gangliosides, globosides, sulfatides, glycophosphphingolipids and glycocalyx, among others.

Preferably, Z is a bond (linking a Gal-Gal disaccharide to a linker or difunctional connector molecule) or a glucose or glucosamine (especially N-acetylglucosamine). It is noted that Z is linked to a galactose residue through a hydroxyl group or an amine group on the galactose of Gal-Gal, preferably a hydroxyl group. A preferred hapten is Gal-Gal-Glu which is represented by the structure:

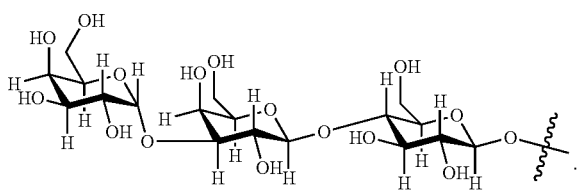

Other ABT groups include, for example, the following groups:

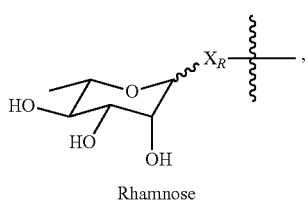

Rhamnose

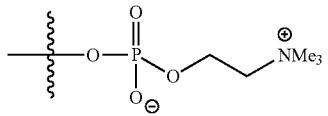

Phosphoryl Choline

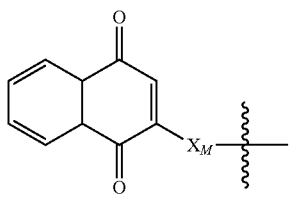

Menadione

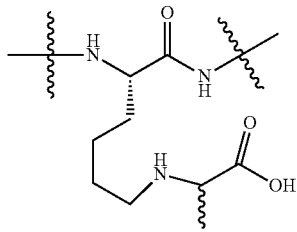

Carboxyethyl Lysine (CEL)

Where $X_R$ is O or S; and
$X_M$ is O or S.

It is noted in the carboxyethyl lysine ABT moiety either one, two or three of the nitrogen groups may be linked to the remaining portion of the molecule through the linker or one or both of the remaining nitrogen groups may be substituted with a dinitrophenyl through an X group as otherwise described herein.

The term "cell binding terminal moiety", "cell binding terminus" or "cell binding moiety" is use to described that portion of a chimeric compound according to the present invention which comprises at least one small molecule or moiety which can bind specifically to prostate specific membrane antigen (PSMA).

Preferred CBT groups for use in the present invention are set forth below:

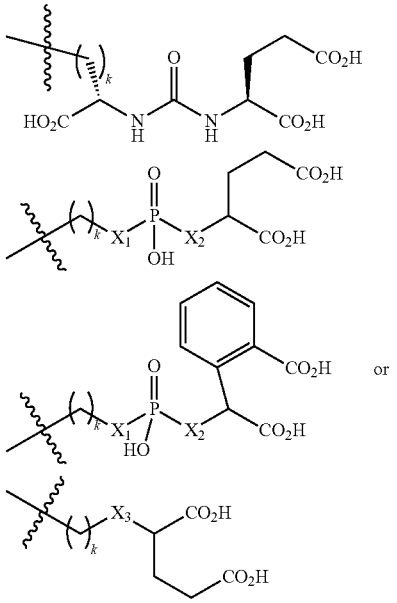

Where $X_1$ and $X_2$ are each independently $CH_2$, O, NH or S; $X_3$ is O, $CH_2$, NW, S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;
k is an integer from 0 to 20, 8 to 12, 1 to 15, 1 to 10, 1 to 8, 1 to 6, 1, 2, 3, 4, 5 or 6; or a salt or enantiomer thereof.

The term "Toll-like Receptor moiety" or TLR ([TLR]) is used to describe a functional group on compounds according to the present invention which comprise a TLR agonist (often, a TLR 7/8 agonist), which is functionalized to link to a linker group as otherwise described herein. Preferred [TLR] groups or moieties for use in the present invention are readily functionalized from a TLR agonist (often a TLR7/8 agonist) to covalently link to a linker group, which can then be linked through a multifunctional connector group [MULTICON] to the [ABT] groups and [CBT] groups of compounds according to the present invention. Preferred TLR agonists which find use in the present invention include those which are selected from the group consisting of Rintatolimod, SMP-105, IPH-3102, CBLB502, MGN-1706, IMO-2055, ANA773, OM-174, ISS1018, Agatolimod, 852A, Imiquimod and Cadi-05. Imiquimod is a preferred TLR7/8 agonist for use in the present invention. The conjugation of a TLR group in compounds according to the present invention serves several important functions contributing to the unexpected anticancer activity of the present compounds including improving the ARM's (ABT group linked to a CBT group) ability to mediate tumor lysis, stimulating APC activation and generating anti-tumor T-cells which provide for enhanced anticancer activity, including prolonged activity and/or immunologic memory. In certain preferred embodiments, conjugation of the TLR group to the ABT and CBT group also limits the entry of the molecule into non-target cells, enhancing selectivity, and favorably prevents nontargeted stimulation of endosomal TLR7/8, while enhancing phagocytosis of PSMA+targeted cells, the result being compositions which exhibit unexpected (synergistic) anticancer activity.

[TLR] groups which can be conjugated to ABT and CBT groups pursuant to the present invention include compounds according to the chemical structure:

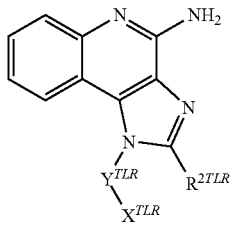

Where $R^{2TLR}$ is moiety which is 3-4 atoms in length wherein said atoms are carbon, oxygen sulfur or nitrogen (nitrogen being substitutable by H and or a $C_1$-$C_3$ alkyl group and are preferably n-butyl, ethoxymethyl, methoxyethyl, or n-propylamine. $Y^{TLR}$ is

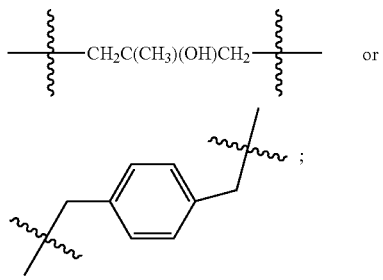

and
$X^{TLR}$ is O, S or N—$R^{NTLR}$ where $R^{NTLR}$ is H or a $C_1$-$C_3$ alkyl group, often H;

Most often $R^{2TLR}$ is a n-butyl group, $Y^{TLR}$ is a

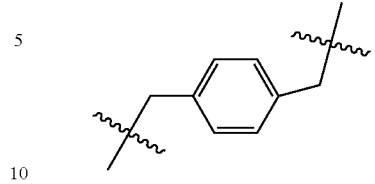

group and $X^{TLR}$ is N—$R^{NTLR}$ where $R^{NTLR}$ is H. Each of these compounds may be further linked with a linker group (both non-labile and labile) for use in compounds according to the present invention. Specific preferred TLR groups for inclusion in the present invention include the following groups PPX, PDX and PTX, below which are based upon the preferred TLR moiety

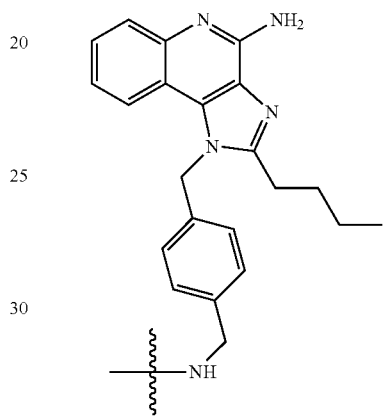

which has been linked to a linker group (e.g., non-labile or labile) and often end-capped with an acetylenic group to form a difunctional 1,2,3-triazole connector group [CON] with an azide as exemplified by the following compounds:

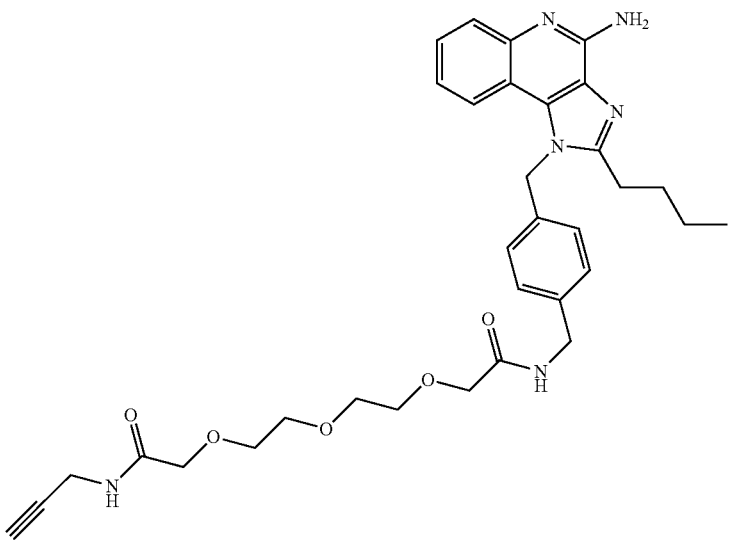

PPX

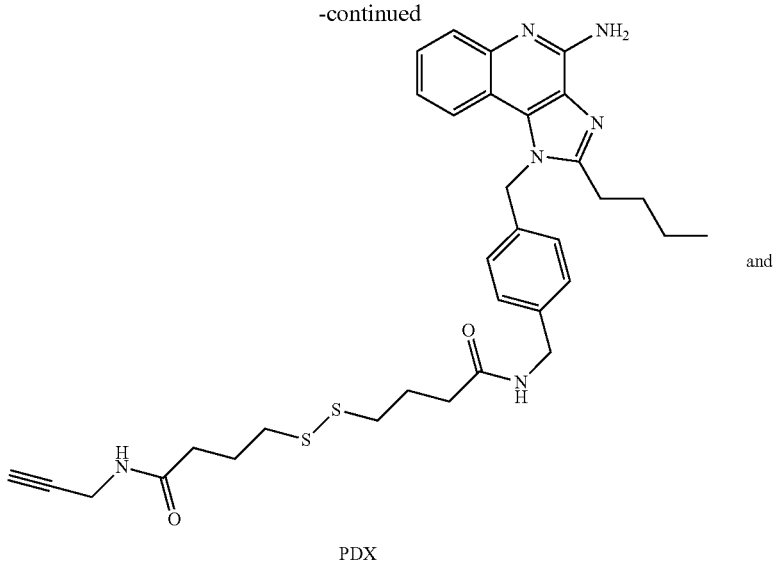
PDX
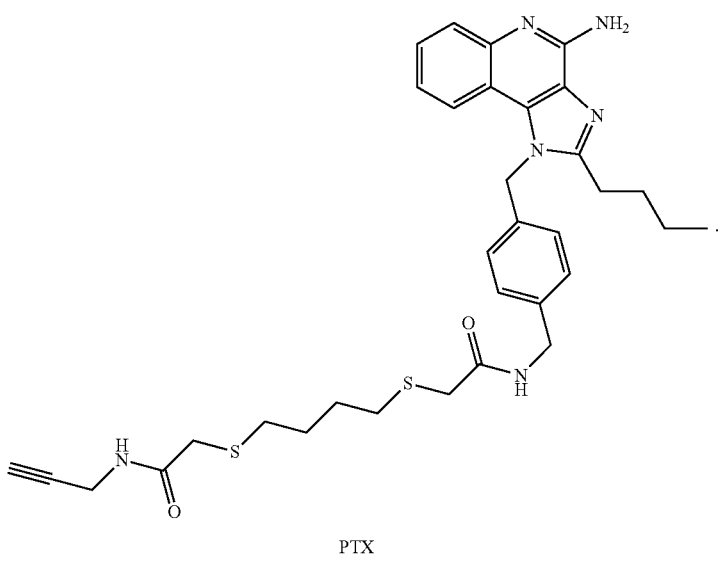
PTX
Additional TLR moieties which can be used in the present invention include:
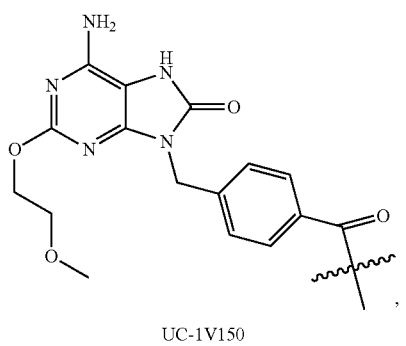
UC-1V150
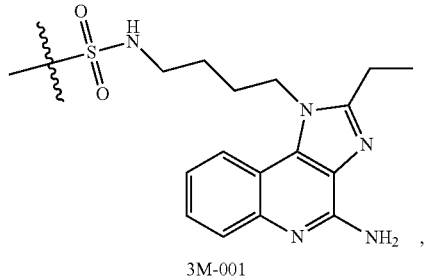
3M-001
N-[4-(4-amino-2-ethyl-1H-imidazo[4,5-c]quinolin-1-yl)butyl]methanesulfonamide -continued

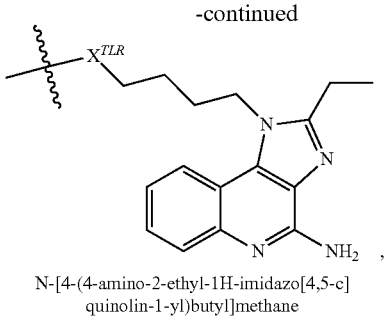

N-[4-(4-amino-2-ethyl-1H-imidazo[4,5-c]
quinolin-1-yl)butyl]methane

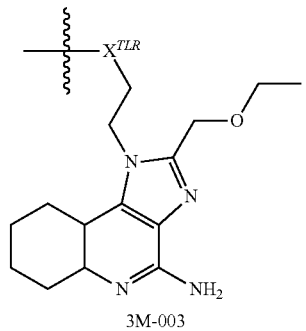

3M-003
4-amino-2-(ethoxymethyl)-alpha, alpha- dimethyl-6,7,8,9-
tetrahydro-1H-imidazo[4,5-c]quinoline-1-ethanol

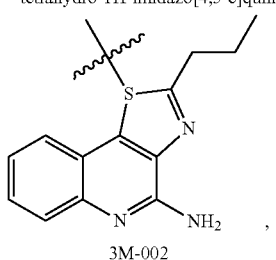

3M-002
2-propylthiazolo[4,5-c]quinolin-4-amine where $X^{TLR}$ is O, S or N—$R^{NTLR}$ where $R^{NTLR}$ is H or a $C_1$-$C_3$ alkyl group, often H, or a salt form thereof. See, for example, Bioorg. Med. Chem. Lett. (2010) 6384; Wu, et al. Proc Natl Acad Sci USA, 2007; 104(10):3990-5; Gorden, et al., The Journal of Immunology, 2005; 174(3):1259-68; and Reece, et al., Proc Natl Acad Sci USA, 2005; 102(42):15190-4.

Preferred TLR group for use in the present invention include groups according to the chemical structure:

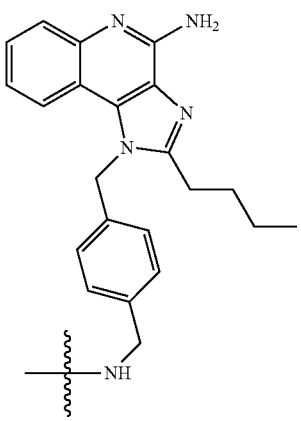 [SMILES: *NCc1ccc(Cn2c(CCCC)nc3c(N)nc4ccccc4c32)cc1]

The term "linker" refers to a chemical entity which connects an antibody binding terminus [ABT] moiety, the cell binding terminus moiety [CBT] or the Toll-like Receptor7/8 moiety [TLR] to the multifunctional connector moiety/molecule [MULTICON]. It is noted that each linker may be connected to [MULTICON} through an optional difunctional connector molecule [CON} as otherwise disclosed here. The linker may be a non-labile linker [NLL] or a labile linker [LL], or optionally may comprise one or more non-labile linkers which are linked to each other or further linked with one or more non-labile linkers. Most often, the linker is a non-labile linker, especially between the [ABT] moiety and the multifunctional connector molecule [MULTICON} and the [CBT] moiety and the multifunctional connector molecule [MULTICON]. In certain instances, especially in the case of the TLR linker to [MULTICON], in proximity to the TLR moiety, the linker may be a labile linker. The linker between the three active functional portions of the molecule, that is the antibody binding terminus [ABT], the cell binding terminus [CBT] and the Toll-like Receptor moiety [TLR] ranges from about 5 Å to about 50 Å or more in length, about 6 Å to about 45 ↑ in length, about 7 Å to about 40 Å in length, about 8 Å to about 35 Å in length, about 9 Å to about 30 Å in length, about 10 Å to about 25 Å in length, about 7 Å to about 20 Å in length, about 5 Å to about 16 Å in length, about 5 Å to about 15 Å in length, about 6 Å to about 14 Å in length, about 10 Å to about 20 Å in length, about 11 Å to about 25 Å in length, etc. Linkers which are based upon ethylene glycol units and are between 2 and 20, 4 and 16 or 8 and 12 glycol units in length may be preferred. By having a linker with a length as otherwise disclosed herein, the ABT moiety, CBT moiety an the TLR moiety may be situated to take advantage of the biological activity of compounds according to the present invention which bind to prostate specific membrane antigen (PSMA) through the [CBT] and attract endogenous antibodies to the cell [ABT] with the TLR moiety also attached functioning synergistically with the other functional units as a pro-inflammatory ligand to improve the compound's ability to mediate tumor lysis by innate immune cells and better stimulate APC activation and generate anti-tumor T-cells to promote immunologic memory to which the compounds are bound, resulting in the selective and targeted cell death of those cells, in whatever tissues they may reside, which express or have PSMA in a synergistic manner. The selection of a linker component is based on its documented properties of biocompatibility, solubility in aqueous and organic media, and low immunogenicity/antigenicity.

Linkers which are based upon or include ethylene glycol units are preferred for use in the present invention. These preferred linkers are between 2 and 100 glycol units in length, but those which are between 2 and 14 glycol units or 4 and 8 glycol units in length may be preferred. Each linker may be linked with the multifuncitional connector molecule [MULTICON] through one or more difunctional connector molecules [CON], Although numerous linkers may be used as otherwise described herein, a linker (non-labile) based upon polyethyleneglycol (PEG) linkages, polypropylene glycol linkages, or polyethyleneglycol-co-polypropylene polymers (up to about 100 units, about 1 to 100, about 1 to 75, about 1 to 60, about 1 to 50, about 1 to 35, about 1 to 25, about 1 to 20, about 1 to 15, 1 to 10, about 8 to 12, about 1 to 8, etc.) may be favored as a linker because of the chemical and biological characteristics of these molecules. The use of polyethylene (PEG) linkages is preferred.

Alternative preferred linkers may include, for example, polyproline linkers and/or collagen linkers as depicted below (n is about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

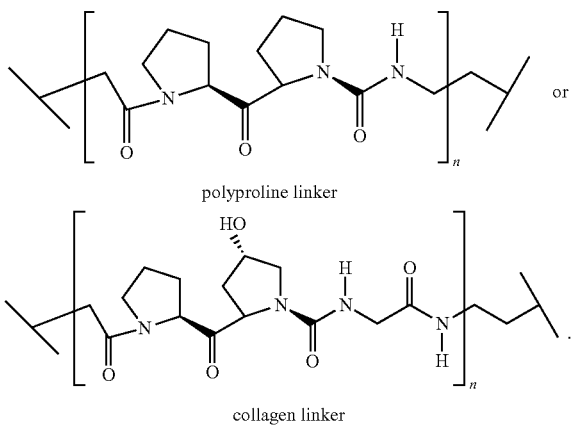

polyproline linker collagen linker

Additional linkers include those according to the chemical structures:

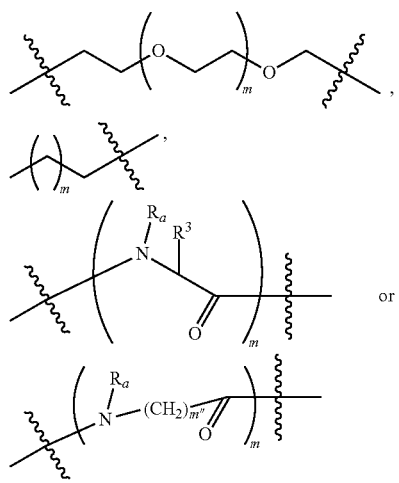

Where $R_a$ is H, $C_1$-$C_3$ alkyl or alkanol or forms a cyclic ring with $R^3$ (proline) and $R^3$ is a side chain derived from an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m" is an integer between 0 to 25, preferably 1 to 25, 1 to 10, 1 to 8, 1, 2, 3, 4, 5, or 6;

m (within this context) is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n (within this context) is an integer from about 1 to 100, about 1 to 75, about 1 to 60, about 1 to 50, about 1 to 45, about 1 to 35, about 1 to 25, about 1 to 20, about 1 to 15, 2 to 10, about 4 to 12, about 5 to 10, about 4 to 6, about 1 to 8, about 1 to 6, about 1 to 5, about 1 to 4, about 1 to 3, etc.).

Another linker according to the present invention comprises a polyethylene glycol linker containing from 1 to 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5 ethylene glycol units which may be further linked through amide groups (which include alkylene groups on either or both sides of the amide group containing one to five methylene units), keto groups (which include alkylene keto groups containing one to five methylene units), amine groups (which include alkylene amine groups containing one to five methylene units), alkylene groups (containing from 1 to 5 methylene units), amino acids or other moieties compatible with polyethylene glycol groups (including difunctional connecting groups [CON]) to other linkers and/or other components of the compound according to the present invention. Still other linkers comprise polypeptides of amino acid residues (D or L). In another embodiment, as otherwise described herein, polypeptides may comprise non-naturally occurring amino acids (non-naturally occurring except for glycine) of the non-labile linker each of which has anywhere from 1-15 methylene groups separating the amino group from the acid group (and from 1 to 100 peptide groups) in providing a linker to the moiety. It is noted that each of the polypeptide linkers and other linkers (including labile linkers) identified in the present application may be further linked with connector molecules/moieties [CON], [MULTICON] molecules/moieties, [ABT] groups, [CBT] groups and/or [TLR] groups through amide groups (which include alkylene groups on either or both sides of the amide group containing one to five methylene units), keto groups (which include alkylene keto groups containing one to five methylene units on either or both sides of the keto group), amine groups (which include alkylene amine groups containing one to five methylene units on either or both sides of the amine group), urethane groups (which include alkylene groups containing one to five methylene units on either or both sides of the urethane moiety) alkylene groups (containing from 1 to 5 methylene units), amino acids or other moieties compatible with the linker chemistry in order to link components of the molecules. It is noted that in the case of polyethylene glycol and polypeptide linkers, the use of an additional group (eg, alkylene amine or other group as described above) or a second linker group may be useful for joining the linker to another component of the molecule, including a [CON] group or a [MULTICON] group. Additionally, more than one linker group identified herein may be linked together to form a linker group as otherwise used in the present compounds, consistent with the stability of the linker chemistries. These extended linkers are often, though not exclusively linked through [CON] connecting groups as otherwise described herein.

Another non-labile linker according to the present invention includes a linker based upon succinimide according to the chemical formula:

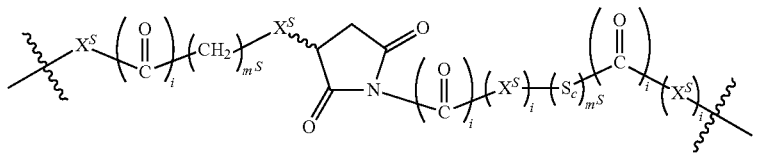

where each $X^S$ is independently S, O or N—$R^S$, preferably S;

$R^S$ is H or $C_{1-3}$ alkyl, preferably H;

$S_c$ is $CH_2$; $CH_2O$; or $CH_2CH_2O$;

i is 0 or 1; and $m^S$ is 0, 1, 2, 3, 4, 5, or 6.

Other linkers which may be used in the present invention include linkers according to the chemical formula:

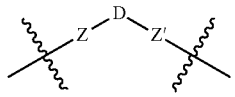

Where Z and Z' are each independently a bond, —$(CH_2)_i$—O, —$(CH_2)_i$—S, —$(CH_2)_i$—N—R,

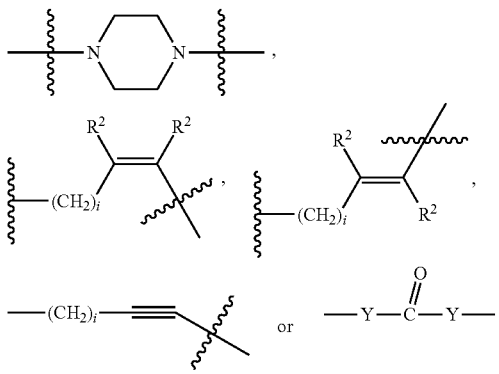

wherein said —$(CH_2)_i$ group, if present in Z or Z', is bonded to a connector, ABT or CBT;

Each R is H, or a $C_1$-$C_3$ alkyl or alkanol group;

Each $R^2$ is independently H or a $C_1$-$C_3$ alkyl group;

Each Y is independently a bond, O, S or N—R;

Each i is independently 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

D is

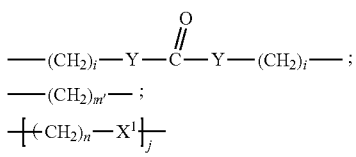

or a bond, or D is

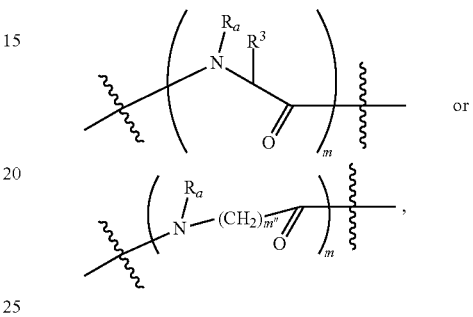

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4, 5, 6, or 7);

with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

n is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;

$X^1$ is O, S or N—R;

R is as described above, and $R_a$, $R_3$, m and m" are the same (as for the same moieties) as above, or a pharmaceutical salt thereof It is noted that for each linker, one or more of the groups as depicted above may be extended through binding with a difunctional connector group [CON], which is described in greater detail hereinbelow. In addition, each linker may be further extended with one or more additional linkers, as otherwise described herein to provide extended linkers. In certain instances, a labile linker may be found in proximity to a [TLR] group.

In certain embodiments, the linker group is a labile group. The labile linker, when used, is used most often to link the [TLR] moiety to the multifunctional connecting molecule [MULTICON], preferably in proximity to the [TLR] moiety. Labile linkers pursuant to the present invention include any linker which may be readily cleaved upon introduction of the TLR-ARMs into the cell through any one of several cellular mechanisms. Although labile linkers may be used anywhere a linker (non-labile linker) group is used in compounds according to the present invention, when labile linkers are used they are often used to link the [TLR] moiety to [MULTICON} in proximity to the [TLR] moiety. The labile linker allows the [TLR] moiety to be cleaved from the trifunctional compounds in order to provide a maximal effect in the cell. These labile linkers include hydrolytically labile (acid labile) linkers, reductively labile linkers (principally disulfide linkers which are reductively cleaved by intracellular glutathione or other disulfide reducing agent) and enzymatically labile linkers (protease substrates). These labile linkers are preferably represented by the chemical structures:

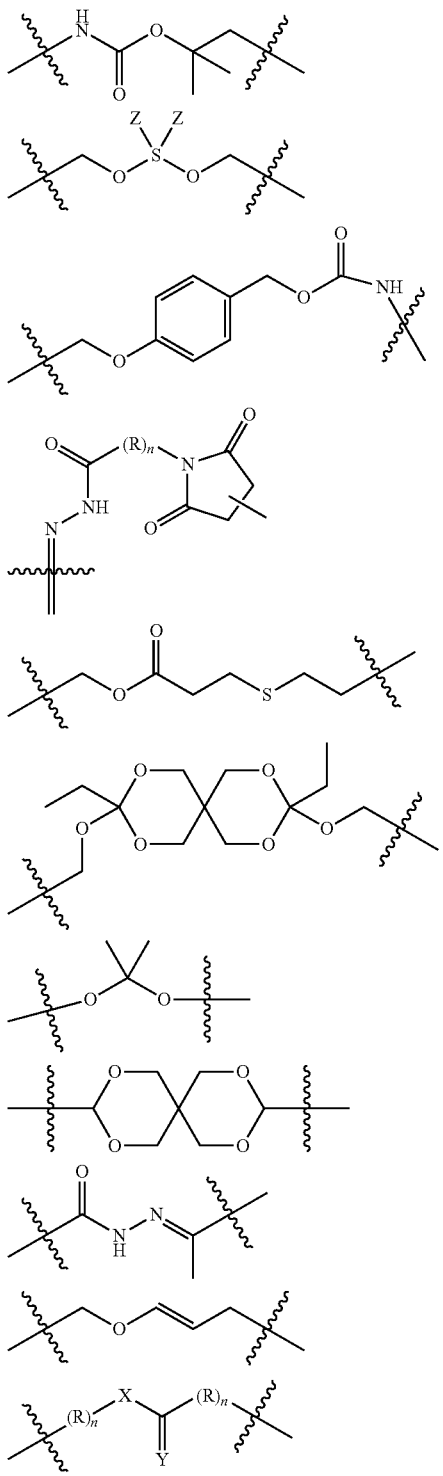

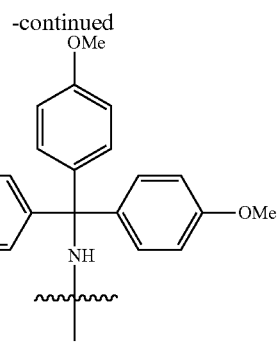

where R is an ethylene glycol group, or a methylene group and n in this labile linker is from 0 to 10, often from 1 to 6, or 1 to 3 and where points of attachment (as indicated) are to other portions of the labile linker, a difunctional connector moiety (CON), a non-labile linker (NLL), or a multifunctional connector molecule [MULTICON], through which an [ABT] functional group and a [CBT] functional group are linked as otherwise described herein;

X is O, N—$R^{AL}$ or S;

$R^{AL}$ is H or a $C_1$-$C_3$ alkyl group (often H or Me, most often H);

Y is O or S and

Z=Me, Et, iPr, tBu, Ph, each of which may be optionally substituted with one or more halogen groups (especially from three up to five Fs, preferably no more than three Fs) and where said Ph group may be further optionally substituted with a $C_1$-$C_3$ alkyl group (which itself may be substituted with up to three halogens, preferably F) or OMe.

Exemplary reductively cleaved moieties (by glutathione, other reductive species within the cell) include moieties according to the chemical formula:

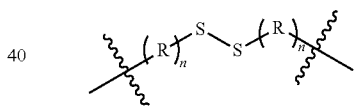

Where R is an ethylene glycol group, or a methylene group and n in this labile linker is from 0 to 10, often from 1 to 6, or 1 to 3 and where points of attachment (as indicated) are to other portions of the labile linker [LL], a difunctional connector molecule or group (CON), a non-labile linker (NLL) or a multifunctional connector group molecule [MULTICON] as otherwise described herein.

Exemplary enzymatically cleaved labile linkers include those according to the chemical structure:

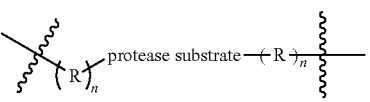

Where the protease (cathepsin) substrate is a a peptide containing from 2 to 50 amino acid units or more, often 2 to 25 amino acid units, 2 to 15 amino acid units, 2 to 10 amino acid units, 2 to 6 amino acids, 2 to 4 amino acids, 2, 3 or 4. Often, the protease substrate, above contains, comprises, consists essentially of or consists of the following peptides the point of attachment being at the distal ends of the peptide:

-Gly-Phe-Leu-Gly-;
-Ala-Leu-Ala-Leu;
-Phe-Arg-;
-Phe-Lys-;
-Val-Cit- (valine-citrulline)
-Val-Lys-
-Val-Ala- and where R (above) is an ethylene glycol group, or a methylene group and n is from 0 to 10, often from 1 to 6, or 1 to 3 and where points of attachment (as indicated) are joined to other portions of the labile linker, a difunctional connector group or molecule (CON), a non-labile linker (NLL), a virus invasion cell binding moiety (VICB) or a cytotoxic moiety (CYT) as otherwise described herein Other enzyme labile linkers are the beta-glucosidase labile linkers according to the chemical structure:

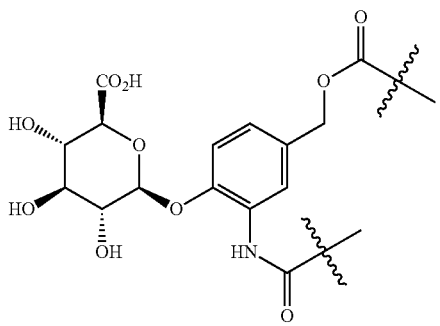 [SMILES: *C(=O)Nc1cc(COC(*)=O)ccc1O[C@@H]1O[C@H](C(=O)O)[C@@H](O)[C@H](O)[C@H]1O]

Where the points of attachment are joined to other portions of the labile linker, a difunctional connector moiety (CON), a non-labile linker (NLL) or a multifunctional connector group or molecule [MULTICON] as otherwise described herein.

In each of the above labile linkers, at the point of attachment in each group, the labile linker may be further linked to a non-labile linker as otherwise described herein, preferably a (poly)ethylene glycol group of from 1 to 12 glycol units (often 2 to 8 glycol units or 4 to 6 units) or an alkylene chain from 1 to 20 methylene units, often 1 to 10 methylene units, often 1 to 8 methylene units, more often 1 to 6 methylene unit, often 2 to 4 methylene units.

The term "multifunctional connector", symbolized by [MULTICON], is used to describe a chemical group or molecule which is optionally included in chimeric compounds according to the present invention which forms from the reaction product of an activated ABT-linker with a CBT moiety (which also is preferably activated) or an ABT moiety with an activated linker-CBT as otherwise described herein. The connector group is the resulting moiety which forms from the facile condensation of at least three separate chemical fragments which contain reactive groups which can provide connector groups as otherwise described to produce chimeric compounds according to the present invention. It is noted that a multifunctional connector moiety or molecule [MULTICON] is readily distinguishable from a linker in that the multifunctional connector is the result of a specific chemistry which is used provide chimeric compounds according to the present invention.

Connecting moieties in the present invention include at least one multifunctional moiety or molecule [MULTICON] which contains three or more functional groups which may be used to covalently bind (preferably, through a linker) to an [ABT] group, a [CBT] group and a [TLR] group, thus linking each of these functional groups into a single compound. Multifunctional connector groups for use in the present invention include moities which have at least three or more functional groups which can bind to linkers to which are bound [ABT], [CBT] and/or [TLR] groups in order to provide compounds which contain at least one [ABT], [CBT] and [TLR] group pursuant to the present invention. These multifunctional connector moieties may also bind to other multifunctional connector molecules in order to create compounds containing a number of [ABT], [CBT] and/or [TLR] groups as defined herein.

Multifunctional connector molecules [MULTICON] comprise any molecule or moiety which contains at least three groups which may be linked to [ABT], [CBT] and/or [TLR] groups, linkers (non-labile linkers or labile linkers) and/or other connector groups (including difunctional and multifunctional connector groups) and preferably comprise five or six-membered aryl or heteroaryl groups (especially six-membered ring groups) exemplified by multifunctional, especially trifunctional or tetrafunctional aryl or heteroaryl groups, including phenyl, pyridyl, pyrimidinyl, 1,3,5-triazinyl, 1,2,3-triazinyl, 1,2,4-triazinyl groups, each of which is substituted with at least 3 and up to 6 functional groups. These functional groups may be derived from nucleophilic or electrophilic groups on the multifunctional connector molecule precursor (the multifunctional connector molecule which forms the [MULTICON] moiety in final compounds according to the present invention) which are condensed onto linker groups (containing, for example an [ABT] group, a [CBT] and/or a [TLR] group) which contain a group which can be linked to the [MULTICON] moiety. [MULTICON] groups which are used in the present invention preferably include substituted phenyl, pyridyl, pyrimidinyl and 1,3,5-triazinyl, 1,2,3-triazinyl, 1,2,4-triazinyl groups, and other groups of multifunctionality especially including groups according to the chemical structure:

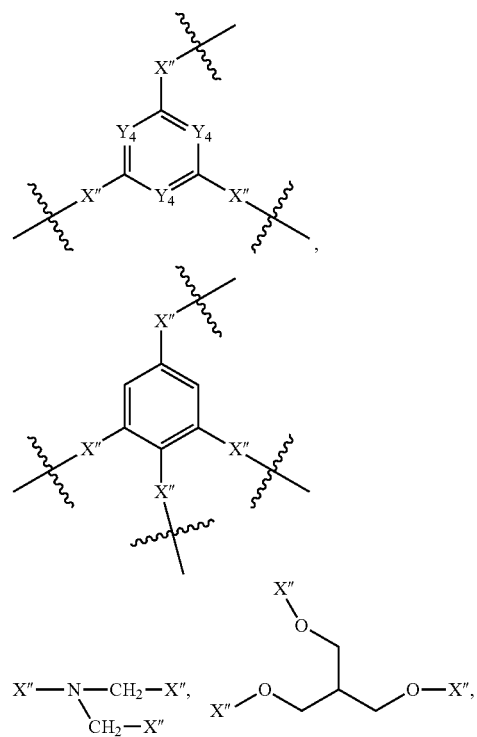

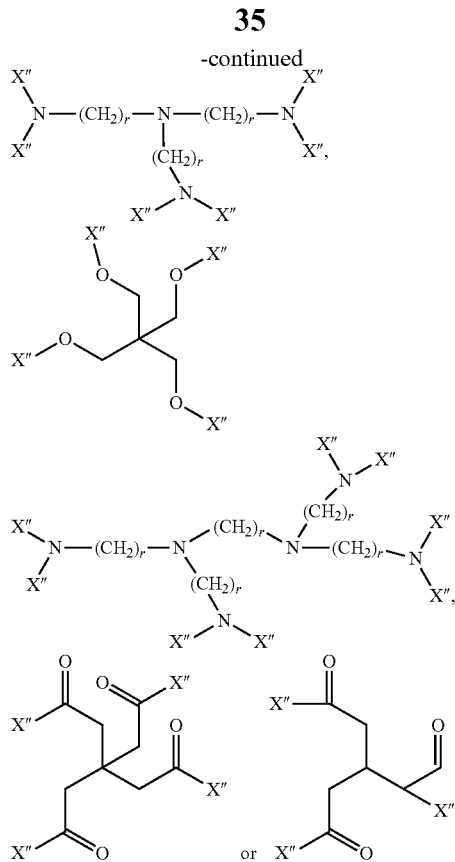

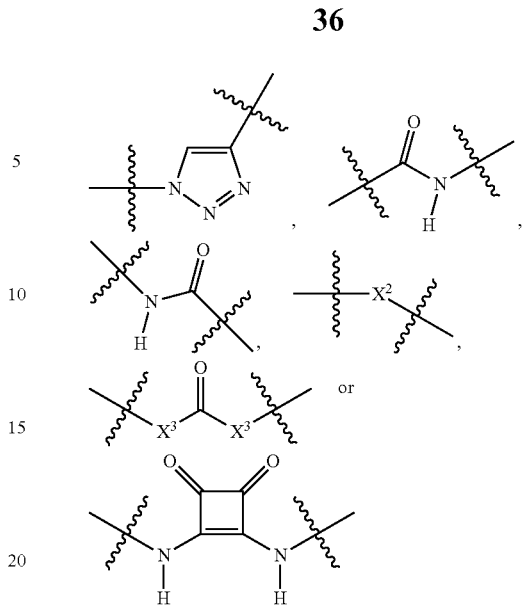

where $Y_4$ is C—H or N; and

Each X" is independently derived from an electrophilic or nucleophilic group, preferably $(CH_2)_{n"}O$, $(CH_2)_{n"}N^{RCON}$, $(CH_2)_{n"}S$, $(CH_2)_{n"}$ or $(CH_2)_{n"}C=O$;

the substituent RCON is H or a $C_1$-$C_3$ alkyl, preferably H or $CH_3$, n" is 0, 1, 2 or 3 and r is an integer from 1-12, often 1, 2, 3, 4, 5 or 6.

The term "difunctional connector group" or [CON] is used to describe a difunctional group which connects two (or more) portions of a linker group to extend the length of the linker group. In certain embodiments, a linker group is reacted with or forms a [CON] group with another linker group as defined herein to form an extended linker group. The reaction product of these groups results in an identifiable connector group [CON] which is distinguishable from the linker group as otherwise described herein. It is further noted that there may be some overlap between the description of the difunctional connector group and the linker group, especially with respect to more common connector groups such as amide groups, oxygen (ether), sulfur (thioether) or amine linkages, urea or carbonate —OC(O)O— groups as otherwise described herein. It is noted that a difunctional connector molecule [CON] used hereunder is preferably connected to two parts of a linker group which binds [ABT], [CBT] and/or [TLR] to the multifunctional connector molecule [MULTICON].

Common difunctional connector groups [CON] which are used in the present invention, principally to link one end of a linker to another end of a linker to provide a longer linker include the following chemical groups:

Where $X^2$ is O, S, $NR^4$, S(O), $S(O)_2$, —$S(O)_2O$, —$OS(O)_2$, or $OS(O)_2O$;

$X^3$ is O, S, $NR^4$; and $R^4$ is H, a $C_1$-$C_3$ alkyl or alkanol group, or a —$C(O)(C_1$-$C_3)$ group.

As discussed hereinabove, it is noted that each of the [ABT], [CBT] and [TLR] functional groups may be further linked to a chemical moiety which bonds two or more of the above connector groups into a multifunctional connector, thus providing complex multifunctional compounds comprising more than one [ABT], [CBT] and/or [TLR] groups within the multifunctional compound.

The term "pharmaceutically acceptable salt" or "salt" is used throughout the specification to describe a salt form of one or more of the compositions herein which are presented to increase the solubility of the compound in saline for parenteral delivery or in the gastric juices of the patient's gastrointestinal tract in order to promote dissolution and the bioavailability of the compounds. Pharmaceutically acceptable salts include those derived from pharmaceutically acceptable inorganic or organic bases and acids. Suitable salts include those derived from alkali metals such as potassium and sodium, alkaline earth metals such as calcium, magnesium and ammonium salts, among numerous other acids well known in the pharmaceutical art. Sodium and potassium salts may be preferred as neutralization salts of carboxylic acids and free acid phosphate containing compositions according to the present invention. The term "salt" shall mean any salt consistent with the use of the compounds according to the present invention. In the case where the compounds are used in pharmaceutical indications, including the treatment of prostate cancer, including metastatic prostate cancer, the term "salt" shall mean a pharmaceutically acceptable salt, consistent with the use of the compounds as pharmaceutical agents.

The term "coadministration" shall mean that at least two compounds or compositions are administered to the patient at the same time, such that effective amounts or concentrations of each of the two or more compounds may be found in the patient at a given point in time. Although compounds according to the present invention may be co-administered to a patient at the same time, the term embraces both administration of two or more agents at the same time or at different times, provided that effective concentrations of all coadministered compounds or compositions are found in the subject at a given time. Chimeric antibody-recruiting compounds according to the present invention may be administered with one or more additional anti-cancer agents or other agents which are used to treat or ameliorate the symptoms of cancer, especially prostate cancer, including metastatic prostate cancer. Exemplary anticancer agents which may be coadministered in combination with one or more chimeric compounds according to the present invention include, for example, antimetabolites, inhibitors of topoisomerase I and II, alkylating agents and microtubule inhibitors (e.g., taxol). Specific anticancer compounds for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

In addition to anticancer agents, a number of other agents may be coadministered with chimeric compounds according to the present invention in the treatment of cancer, especially prostate cancer, including metastatic prostate cancer. These include active agents, minerals, vitamins and nutritional supplements which have shown some efficacy in inhibiting prostate cancer tissue or its growth or are otherwise useful in the treatment of prostate cancer. For example, one or more of dietary selenium, vitamin E, lycopene, soy foods, vitamin D, green tea, omega-3 fatty acids and phytoestrogens, including beta-sitosterol, may be utilized in combination with the present compounds to treat prostate cancer.

In addition, active agents, other than traditional anticancer agents have shown some utility in treating prostate cancer. The selective estrogen receptor modulator drug toremifene may be used in combination with the present compounds to treat cancer, especially prostate cancer, including metastatic prostate cancer. In addition, two medications which block the conversion of testosterone to dihydrotestosterone, finasteride and dutasteride, are also useful in the treatment of prostate cancer when coadministered with compounds according to the present invention. The phytochemicals indole-3-carbinol and diindolylmethane, may also be coadministered with the present compounds for their effects in treating prostate cancer. Additional agents which may be combined with compounds according to the present invention include antiandrogens, for example, flutamide, bicalutamide, nilutamide, and cyproterone acetate as well as agents which reduce the production of adrenal androgens (e.g. DHEA), such as ketoconazole and aminoglutethimide. Other active agents which may be combined with compounds according to the present invention include, for example, GnRH modulators, including agonists and antagonists. GnRH antagonists suppress the production of LH directly, while GnRH agonists suppress LH through the process of downregulation after an initial stimulation effect. Abarelix is an example of a GnRH antagonist, while the GnRH agonists include leuprolide, goserelin, triptorelin, and buserelin, among others. These agents may be combined with compounds according to the present invention in effective amounts. In addition, abiraterone acetate may also be combined with one or more compounds according to the present invention in the treatment of prostate cancer, especially including metastatic prostate cancer.

Other agents which may be combined with one or more compounds according to the present invention, include the bisphosphonates such as zoledronic acid, which have been shown to delay skeletal complications such as fractures which occur with patients having metastatic prostate cancer. Alpharadin, another agent, may be combined with compounds according to the present invention to target bone metastasis. In addition, bone pain due to metastatic prostate cancer may be treated with opioid pain relievers such as morphine and oxycodone, among others, which may be combined with compounds according to the present invention.

The present invention preferably relates to compounds according to the general chemical structure:

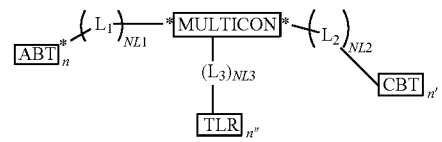

wherein each n, n' and n" in a molecule is independently an integer from 1 to 15, 1 to 10, 1 to 5, 1 to 3, 2 to 3, 2 to 5, (often 1 or 2, preferably 1);

each of NL1, NL2 and NL3 is an integer from 1 to 10, often 1 to 5, often 1 or 2, most often 1, with the proviso that n≥NL1, n' is ≥NL2 and n" is ≥NL3;

[ABT] is an antibody binding moiety according to the chemical formula:

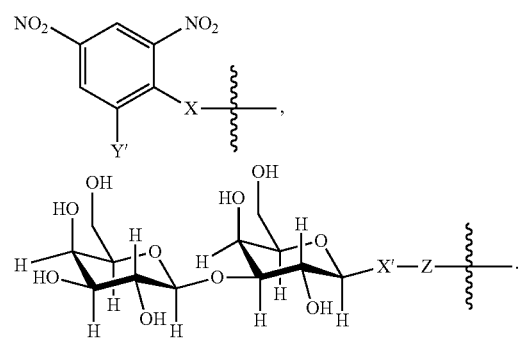

-continued

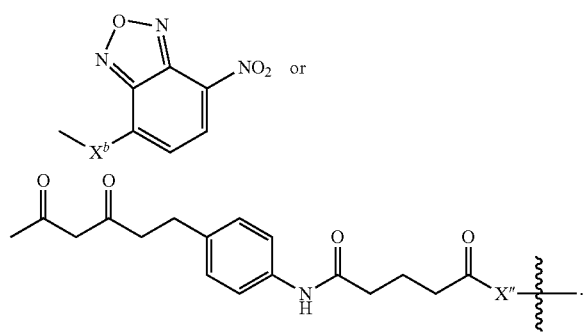

Where Y' is H or $NO_2$;

X is O, $CH_2$, $NR^1$, S(O), $S(O)_2$, $-S(O)_2O$, $-OS(O)_2$, or $OS(O)_2O$;

$R^1$ is H, a $C_1$-$C_3$ alkyl group, or a $-C(O)(C_1$-$C_3)$ group;

X' is $CH_2$, O, N—R", or S, preferably O;

$R^{1'}$ is H or $C_1$-$C_3$ alkyl;

Z is a bond, a monosaccharide, disaccharide, oligosaccharide, glycoprotein or glycolipid;

$X^b$ is a bond, O, $CH_2$, $NR^1$ or S;

X" is O, $CH_2$, $NR^1$;

$R^1$ is H, a $C_1$-$C_3$ alkyl group or a $-C(O)(C_1$-$C_3)$ group;

[CBT] is a cell binding moiety according to the chemical formula:

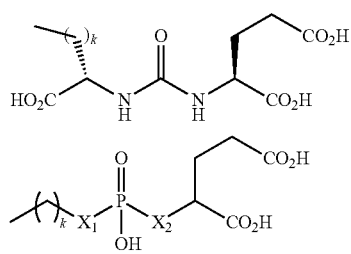

Where $X_1$ and $X_2$ are each independently $CH_2$, O, NH or S;

$X_3$ is O, $CH_2$, $NR^1$, S(O), $S(O)_2$, $-S(O)_2O$, $-OS(O)_2$, or $OS(O)_2O$;

$R^1$ is H, a $C_1$-$C_3$ alkyl group, or a $-C(O)(C_1$-$C_3)$ group;

k is an integer from 0 to 20, 8 to 12, 1 to 15, 1 to 10, 1 to 8, 1 to 6, 1, 2, 3, 4, 5 or 6; [TLR] is a group

[TLR] is a moiety derived from a toll-like receptor agonist according to the chemical structure:

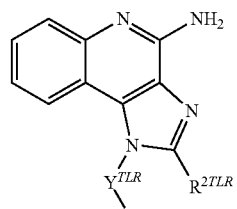

Where $R^{2TLR}$ is moiety which is 3-4 atoms in length wherein said atoms are carbon, oxygen sulfur or nitrogen (nitrogen being substitutable by H and or a $C_1$-$C_3$ alkyl group and $R^{2TLR}$ is often n-butyl, ethoxymethyl, methoxyethyl, or n-propylamine, more often n-butyl);

$Y^{TLR}$ is

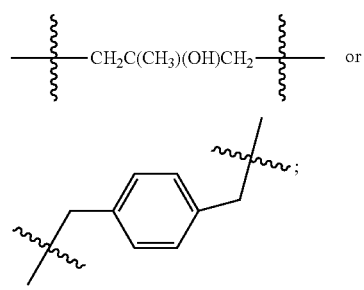

and $X^{TLR}$ is O, S or N—$R^{NTLR}$ where $R^{NTLR}$ is H or a $C_1$-$C_3$ alkyl group, often H; or

[TLR] is a group PPX, PDX and PTX which comprises a preferred TLR moiety

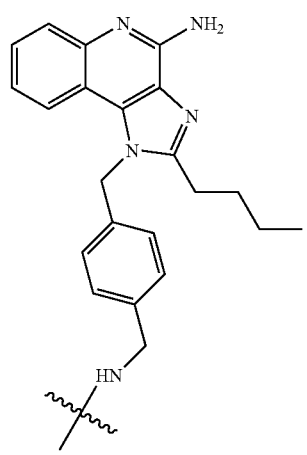 [SMILES: *NCc1ccc(Cn2c(CCCC)nc3c(N)nc4ccccc4c32)cc1]

which is linked with a linker group (non-labile linker or labile linker) and is often end-capped with an acetylenic group for forming a difunctional 1,2,3-triazole connector group [CON] with an azide:

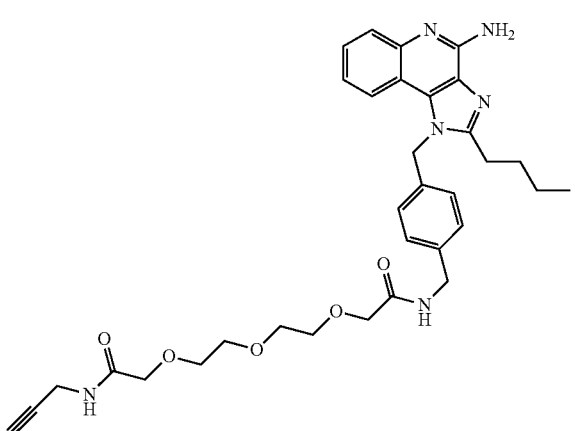
PPX
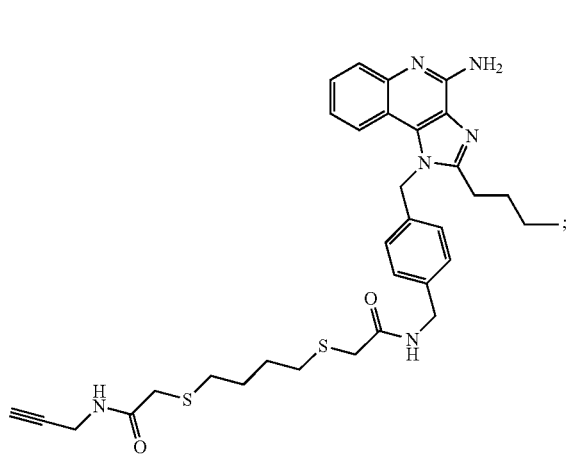
PDX
or
[TLR] is a group according to the chemical structure:
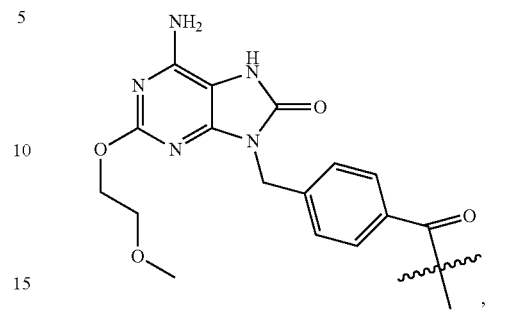
UC-1V150
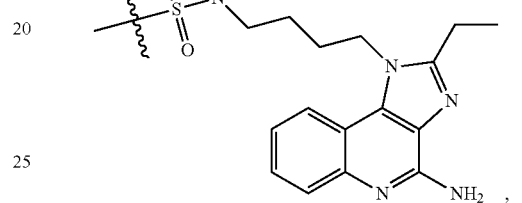
3M-001
N-[4-(4-amino-2-ethyl-1H-imidazo[4,5-c]
quinolin-1-yl)butyl]methanesulfonamide
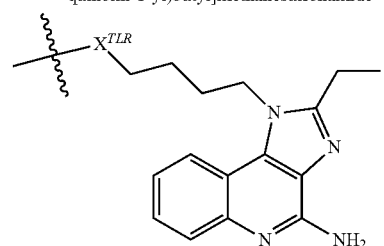
N-[4-(4-amino-2-ethyl-1H-imidazo[4,5-c]
quinolin-1-yl)butyl]methane
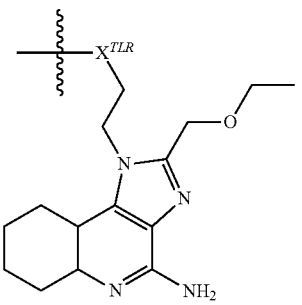
3M-003
4-amino-2-(ethoxymethyl)-alpha, alpha- dimethyl-6,7,8,9-
tetrahydro-1H-imidazo[4,5-c]quinoline-1-ethanol
or
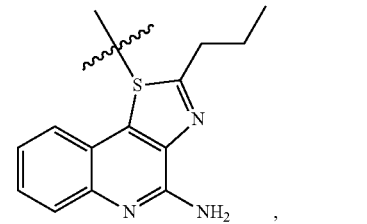
3M-002
2-propylthiazolo[4,5-c]quinolin-4-amine
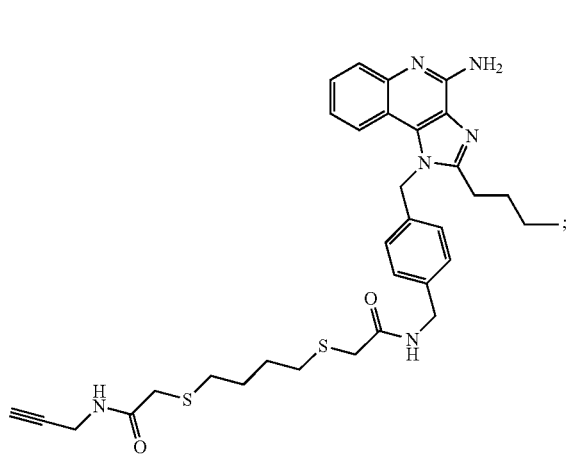
PTX where $X^{TLR}$ is O, S or N—$R^{NTLR}$ where $R^{NTLR}$ is H or a $C_1$-$C_3$ alkyl group, often H, or a salt form thereof;
$L_1$, $L_2$ and $L_3$ are each independently a linker according to the chemical formula:

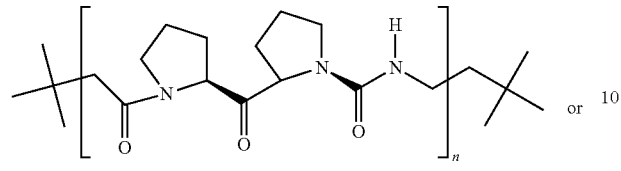
polyproline linker

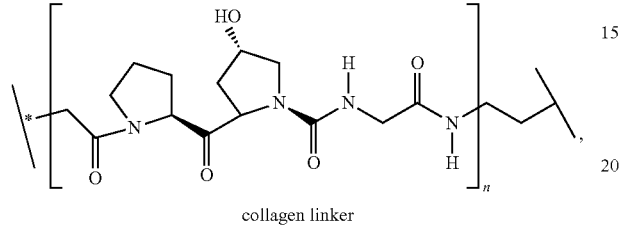
collagen linker a group

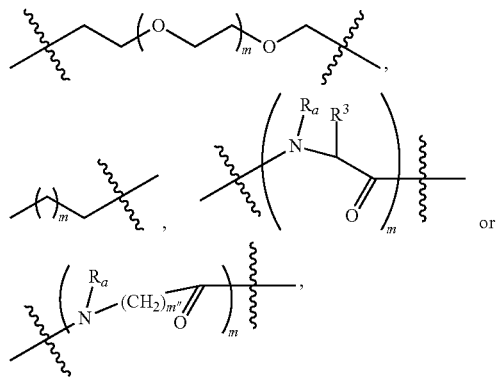

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 12, 1 to 10, 1 to 8, 1 to 6, 1, 2, 3, 4, 5, 6, 7, 8, 9, 10 11 or 12, 2 to 50, 3 to 45); Where $R_a$ is H, $C_1$-$C_3$ alkyl or alkanol or forms a cyclic ring with $R^3$ (proline) and $R^3$ is a side chain derived of an amino acid preferably selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), serine (methanol), threonine (ethanol, 1-hydroxyethane), tryptophan (methyleneindole), tyrosine (methylene phenol) or valine (isopropyl);
m" is an integer between 0 to 25, preferably 1 to 10, 1 to 8, 1, 2, 3, 4, 5, or 6;
m is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; and n is an integer from 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5; or
L is a linker according to the chemical formula:

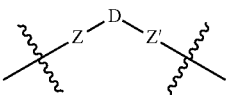

Where Z and Z' are each independently a bond, —$(CH_2)_i$—O, —$(CH_2)_i$—S, —$(CH_2)_i$—N—R,

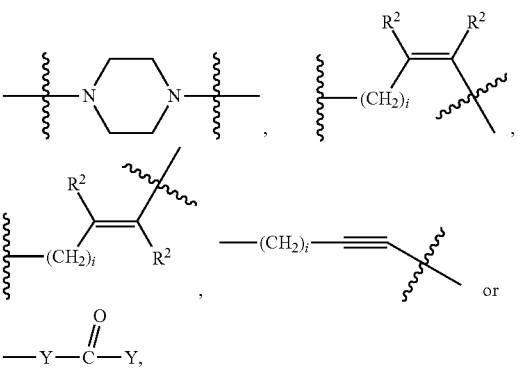

wherein said —$(CH_2)_i$ group, if present in Z or Z', is bonded to [MULTICON], [ABT], [CBT], or [TLR] or an optional difunctional connector group [CON], if present;
Each R is independently H, or a $C_1$-$C_3$ alkyl or alkanol group;
Each $R^2$ is independently H or a $C_1$-$C_3$ alkyl group;
Each Y is independently a bond, O, S or N—R;
Each i is independently 0 to 100, 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 5;
D is

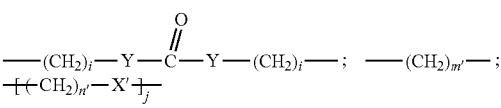

or a bond, or D may be

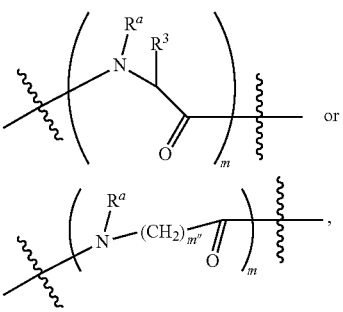

or a polypropylene glycol or polypropylene-co-polyethylene glycol linker having between 1 and 100 glycol units (1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4 or 52 and 50, 3 and 45); with the proviso that Z, Z' and D are not each simultaneously bonds;

j is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4, 5, 6, 7, 8, 9, 10, 11 or 12;

m' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4, 5, 6, 7, 8, 9, 10, 11 or 12;

n' is 1 to 100, 1 to 75, 1 to 60, 1 to 55, 1 to 50, 1 to 45, 1 to 40, 2 to 35, 3 to 30, 1 to 15, 1 to 10, 1 to 8, 1 to 6, 1, 2, 3, 4, 5, 6, 7, 8, 9, 10, 11 or 12;

$X^1$ is O, S or N—R, R is as described above;

$R_a$, $R_3$, m and m" are the same as (for the same moieties) above;

[MULTICON] is preferably a multifunctional connector group or molecule according to the chemical structure:

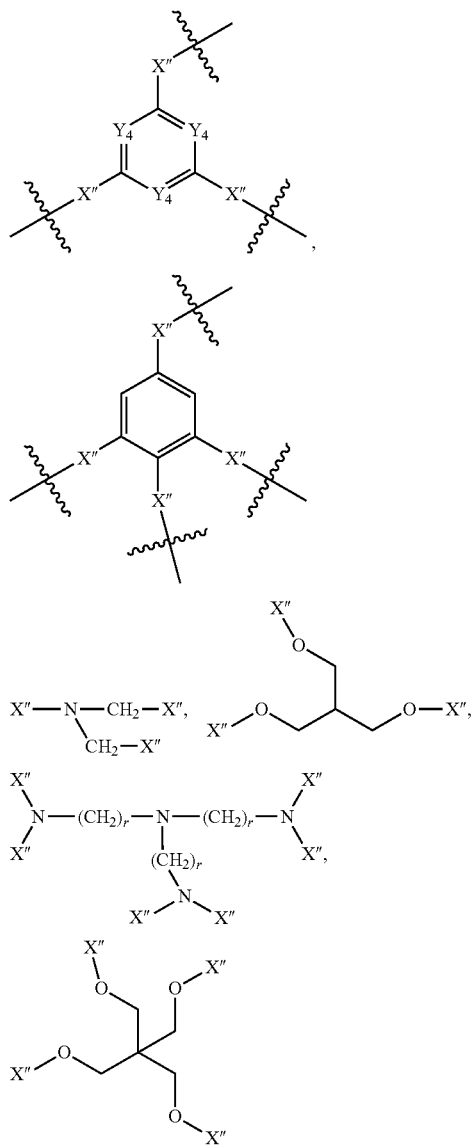

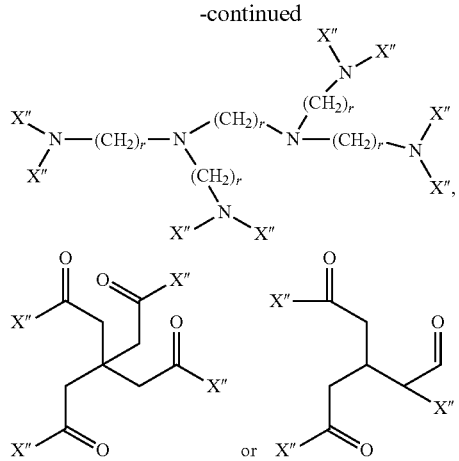

where $Y_4$ is C—H or N; and

Each X" is independently derived from an electrophilic or nucleophilic group, preferably $(CH_2)_{n''}O$, $(CH_2)_{n''}N^{RCON}$, $(CH_2)_{n''}S$, $(CH_2)_{n''}$ or $(CH_2)_{n''}C=O$;

the substituent RCON is H or a $C_1$-$C_3$ alkyl, preferably H or $CH_3$ and n" is 0, 1, 2 or 3 and r is an integer from 1 to 12, often 1, 2, 3, 4, 5 or 6.

The optional difunctional connector group or molecule [CON], if present, is a moiety according to the chemical structure:

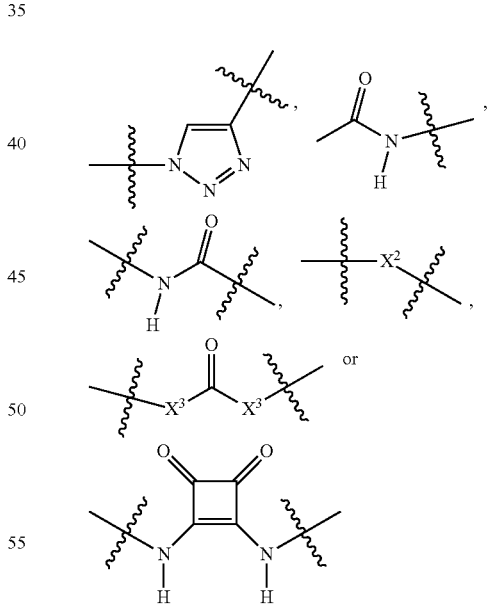

Where $X^2$ is O, S, $NR^4$, S(O), $S(O)_2$, —$S(O)_2O$, —$OS(O)_2$, or $OS(O)_2O$;

$X^3$ is $NR^4$, O or S; and $R^4$ is H, a $C_1$-$C_3$ alkyl or alkanol group, or a —C(O)($C_1$-$C_3$) group; or a pharmaceutically acceptable salt, solvate or polymorph thereof.

In preferred aspects of the invention, the antibody binding terminus (ABT) is

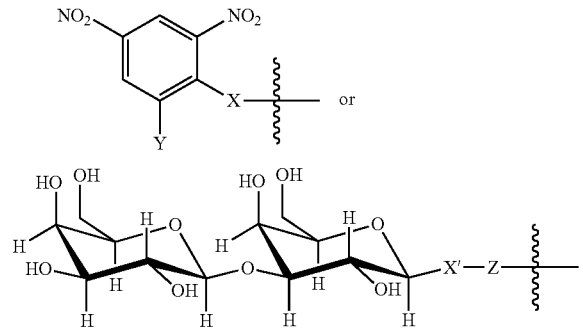

Y' is NO₂;
X' is O;
Z is a bond, a monosaccharide or a disaccharide.

In preferred aspects of the invention, [CBT] is

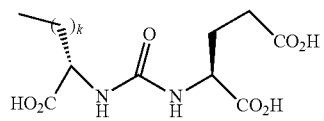

Where k is an integer from 0 to 20, 1 to 20, 1 to 8, 2 to 6, 3 to 5, 3 to 4, 1, 2, 3, 4, 5 or 6.

In certain preferred aspects, the multifunctional connector moiety [MULTICON] is a 1,3,5-triazinyl group according to the structure:

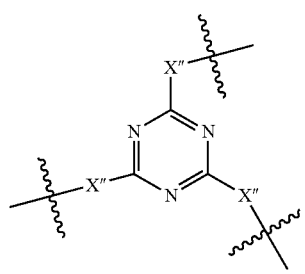

wherein each X" is independently O, S or NR$^{CON}$,
and R$^{CON}$ is H or CH₃, preferably H.

In certain preferred aspects, the compound contains a difunctional connector moiety [CON} according to the structure:

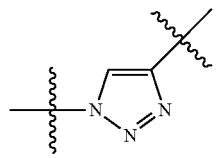 [SMILES: *c1cn(*)nn1]

group which can be covalently bonded at

with a ABT group, a CBT group or a TLR group or alternatively, is preferably bonded to two ends of linker group to provide compounds as otherwise described herein.

In still other preferred aspects the linker group is an oligo or polyethyleneglycol moiety of the structure:

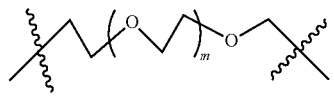

Where m is from 1 to 100 or as otherwise described herein, preferably from 1 to 12, 2 to 10, 4 to 8, 2 to 6, 8 to 12, 2, 3, 4, 5, 6, 7, 8, 9, 10 11 or 12. Noted here is that polypropylene glycol or polyethylene glycol-co-polypropylenene glycol linkers may be substituted for PEG groups in the present compounds.

Figure 1:
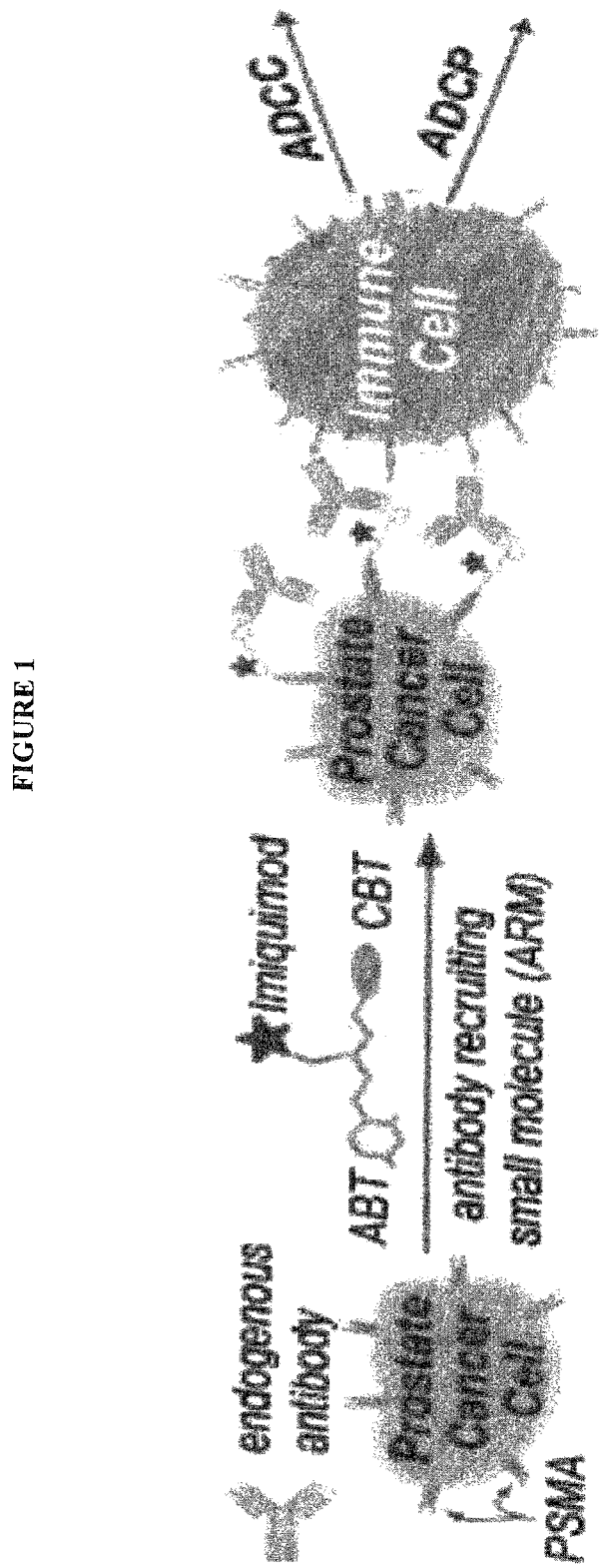
FIG. 1 shows a proposed mechanism for antibody recruiting molecules (ARMs) conjugated to TLR agonists, an antibody binding terminus (ABT) and a cell binding terminus (CBT) resulting in antibody dependent cytotoxicity (ADCC) and antibody dependent phagocytosis (ADCP).
Figure 2:
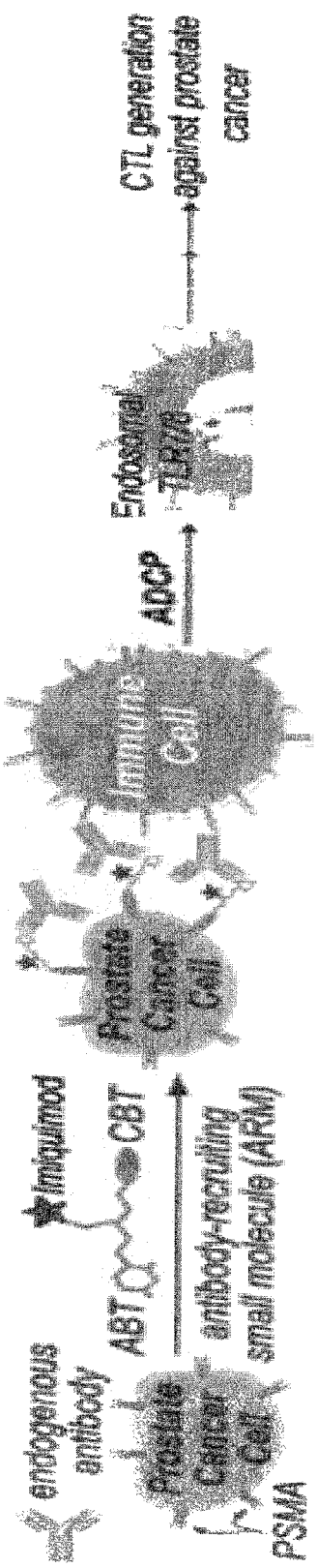
FIG. 2 shows that the rationale for ARM-conjugates includes improved pharmacodynamics—that it is important to TARGET immunostimulation and minimize toxicities, while maximizing therapeutic effect. Because TLR are located in endosomes, TLR agonists such as imiquimod should not be able to interact with the receptors until phagocytosis of an ARM-opsonized target has occurred.
Figure 3:
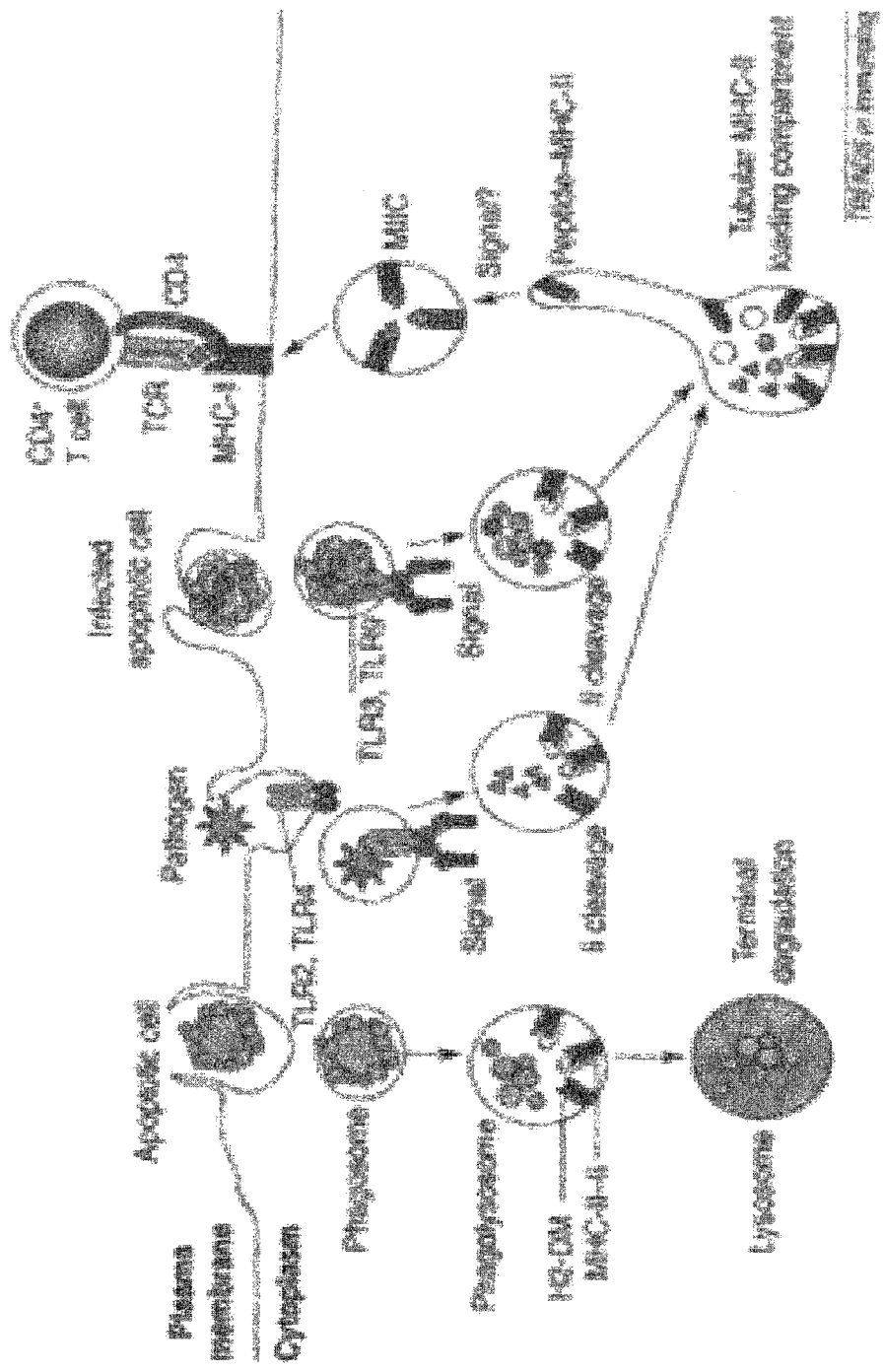
FIG. 3 shows that another rationale for ARM-conjugates includes enhanced immunostimulation. It is important to TARGET immunostimulation by conjugation of TLR agonists to proteins which leads to the generation of protein-specific CD4+ and CD8+ T-cells which are upregulated. In addition, individual phagosomes as opposed to whole cells may be the information-processing units of DCs.
Figure 4:
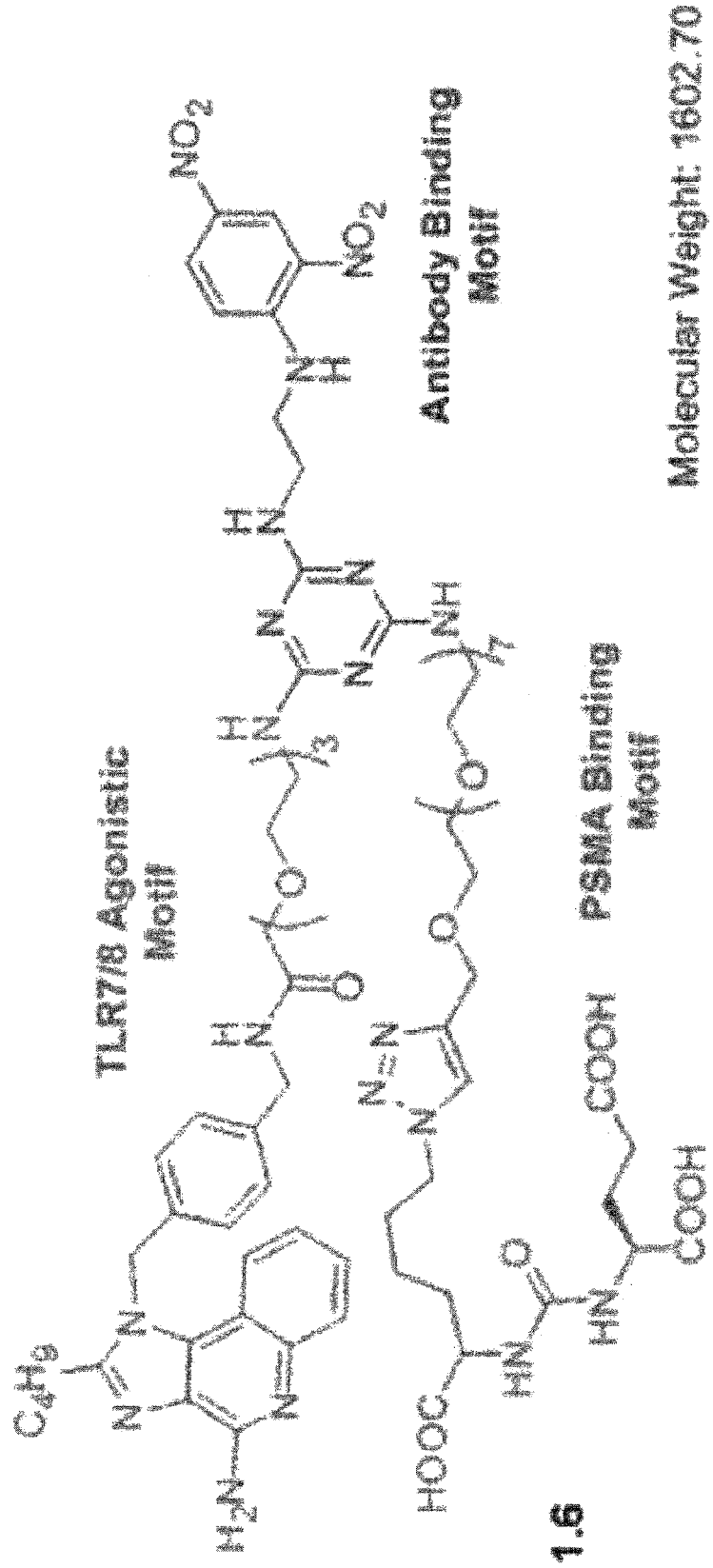
FIG. 4 shows a preferred embodiment (ARM-P8-IMQ) according to the present invention which utilizes a TLR moiety derived from Imiquimod conjugated to PSMA binding moiety (Cell Binding Terminus or CBT) and the antibody binding terminus (ABT) through a linker and a multifunctional connector moiety (MULTICON).

A preferred compound according to the present invention is set forth in attached FIG. 4 or FIG. 5. The compound in FIG. 4 or 5 may be modified to incorporate an alkylene linker L₁ between the antibody binding motif and the triazine [MULTICON] of between 2 and 12 (i.e., 2, 3, 4, 5, 6, 7, 8, 9, 10, 11 or 12) methylene units in length, an oligo/polyethylene glycol linker L₂ between the diazole [CON] moiety and the [MULTICON] moiety of the PSMA binding motif or an oligo/polyethylene glycol linker L₃ between the amide and the [MULTICON] moiety of the TLR 7/8 Agonistic Motif of between 2 and 12 (i.e., 2, 3, 4, 5, 6, 7, 8, 9, 10, 11 or 12) ethylene glycol units.

Pharmaceutical compositions comprising combinations of an effective amount of at least one trifunctional chimeric compound TLR-ARM compound according to the present invention, and one or more of the compounds as otherwise described herein, all in effective amounts, in combination with a pharmaceutically effective amount of a carrier, additive or excipient, represents a further aspect of the present invention.

The compositions of the present invention may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compositions of this invention may also be administered topically, especially to treat skin cancers, psoriasis or other diseases which occur in or on the skin. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water.

Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compound in a pharmaceutical composition of the instant invention that may be combined with the carrier materials to produce a single dosage form will vary depending upon the host and disease treated, the particular mode of administration.

Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one additional non-antibody attracting compound which may be used to treat cancer, prostate cancer or metastatic prostate cancer or a secondary effect or condition thereof.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject (e.g. a male human) suffering from cancer can be treated by administering to the patient (subject) an effective amount of a chimeric antibody recruiting compound according to the present invention including pharmaceutically acceptable salts, solvates or polymorphs, thereof optionally in a pharmaceutically acceptable carrier or diluent, either alone, or in combination with other known anticancer or pharmaceutical agents, preferably agents which can assist in treating prostate cancer, including metastatic prostate cancer or ameliorate the secondary effects and conditions associated with prostate cancer. This treatment can also be administered in conjunction with other conventional cancer therapies, such as radiation treatment or surgery.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-3% wt/wt in a suitable carrier.

The compound is conveniently administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30

This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds. In certain preferred aspects of the invention, one or more chimeric antibody-recruiting compound according to the present invention is coadministered with another anticancer agent and/or another bioactive agent, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

General Chemical Synthesis

The trifunctional chimeric antibody-recruiting compounds according to the present invention may be synthesized readily using standard multifunctional connector groups or molecules to bind linker groups which link the cell binding terminus [CBT], the antibody binding terminus [ABT] and the Toll-like Receptor terminus [TLR] along with appropriate protecting groups when necessary. The approach uses standard functional group chemistry in order to link a cell binding moiety [CBT], an antibody binding moiety [ABT] and a Toll-like Receptor moiety [TLR] to a multifunctional connector group or molecule [MULTICON] through linker groups as otherwise disclosed herein. It is noted that linker groups may contain optional difunctional connector groups [CON] linking portions of the linker group together. Noted here is the fact that the difunctional connector group is not required and the linker, as otherwise described herein, may be covalently bonded directly to [MULTICON] and correspondingly to [CBT], [ABT] and [TLR] without the formation of a specific difunctional connector moiety [CON]. In the present invention, the difunctional connector moiety [CON], which is preferably included in chimeric antibody-recruiting compounds according to the present invention, reflects its formation reflective of favorable synthetic chemistries to provide chimeric compounds as otherwise disclosed herein.

The synthetic chemistry which may be utilized to produce compounds according to the present invention is depicted in FIGS. 5-8 and is representative of the synthetic steps which are utilized to obtain compounds according to the present invention. These synthetic steps are similar to chemical synthetic steps which are described in international application PCT/US2009/002957, published as WO2009/139863 Nov. 19, 2009, which is incorporated by reference herein, and modified consistent with the disclosure of the present invention.

FIG. 5 shows a rather facile 3-step chemical synthesis of compound 1.6 (FIG. 4) pursuant to the present invention. In this method, a multifunctional connector molecule precursor, in this case 2,4,6-trichloro-1,3,5-triazine is reacted in a step-wise fashion with CBT precursor compound 1.2 (FIG. 7 hereof), TLR precursor compound 1.4 (FIG. 8) and ABT precursor compound 1.3 (FIG. 7, insert) to afford compound 1.6. Alternative precursor compounds may be readily synthesized which can provide a variety of CBT, ABT and TLR precursor compounds to afford numerous compounds according to the present invention. Substitution of a multifunctional connecting molecule precursor is also rather straight forward and can be adapted from the synthetic chemical steps which are otherwise disclosed herein and adapted from WO2009/139863, which is incorporated by reference herein.

CBT precursor compound 1.2 (FIG. 7) is prepared facially starting from a diester protected glutamic acid, which is first converted to the isocyanate, reacted with protected lysine which provides the urea connected glutamic acid lysine compound, which is deprotected and reacted with an azide compound to provide protected azide derivative, which is then reacted with acetylenic amine intermediate compound 1.1 (FIG. 6) which forms a difunctional connector molecule [CON] to provide precursor compound 1.2.

ABT precursor compound 1.3 (FIG. 7, inset) is obtained by reacting 1-chloro-2,4-dinitrophenol with ethylene diamine to provide free amine ABT precursor compound 1.3.

TLR7/8 precursor compound 1.4 (FIG. 8) is prepared from dihydroxy-quinoline, which first has a nitro group introduced in the pyridine ring, followed by forming the nitro-containing dichloro quinoline compound, which is reacted with p-phenyldimethylamine wherein one of the two amine groups is protected to provide an amine protected phenylamine-substituted chloro, nitro quinoline, which is reacted with n-butylacyl chloride in triethyl amine and solvent to provide the n-butyl substituted quinoline analog which is further reacted with n-butyl acyl chloride in triethylamine, followed by calcium oxide to afford the N-protected fused tricyclic compound containing a chlorine group. The chlorine group of the N-protected fused tricyclic compound is displaced with $NH_2OBn$ followed by DPEA in ethanol to afford the fused tricyclic quinoline compound containing two free amine groups to which an ethylene glycol linker group (with three ethylene glycol groups) endcapped with a free amine group is provided as compound 1.4.

Alternative compounds with different ABT, CBT and/or TLR moieties may be synthesized, reacted with linker groups to form amine-terminated precursor compounds and then reacted with the trichlorotriazine compounds pursuant to the reaction scheme which is set forth in FIG. 8 hereof to provide the present compounds.

Alternative approaches to the chemical syntheses which are presented above may be used as well, which rely on alternative functional group chemistries. These traditional functional group chemistries may be used in various aspects according to the present invention to create covalent bonds to conjugate the various functional groups to form compounds according to the present invention. For example, as depicted in the scheme set forth in the figure below, a carboxylic acid, such as L-A, could be coupled to either an amine or an alcohol, such as C-A, to generate esters or amides through standard carbodiimide conditions (DCC, EDC, DIC) along with base and catalytic amine (DMAP, imidazole), by conversion to the acid chloride through oxalyl chloride or thionyl chloride etc. followed by addition of amine/alcohol. These provide CBT precursor compounds and ABT precursor compounds similar to compounds 1.2 and 1.3 (FIG. 7). TLR moieties may be modified accordingly to provide TLR linker precursor compounds which may be condensed onto multifunctional connecting groups similar to the approach used in FIG. 5 hereon. Alternative multifunctional connect groups may be substituted for the triazine compound used in the synthetic approach presented in FIG. 5.

Additionally, for example, other functional group chemistry, relying on, for example, an amine or an alcohol, such as A-A, can be coupled to an isocyanate or an isothiocyanate, such as C-E, to generate ureas, thioureas, or the corresponding carbonates or thiocarbonates to provide ABT, CBT and TLR moieties linked to linker groups containing functional groups which can be reacted with a multifunctional connector group precursor compounds to provide compounds of the present invention.

In yet another approach, a difunctional triazole connecting group moiety within a linker group may be synthesized through a cycloaddition reaction between an azide, such as C-B, and an alkyne, such as L-C. This reaction can be catalyzed by copper, such as copper sulfate along with ascorbic acid, to facilitate a clean reaction.

Still, in a further approach, for example, a heterolinker can be made through treating a nucleophile, such as A-A, with the appropriate leaving group, such as L-E. Some leaving groups could be halogens, such as bromine, or sulfonates, such as triflates or tosylates.

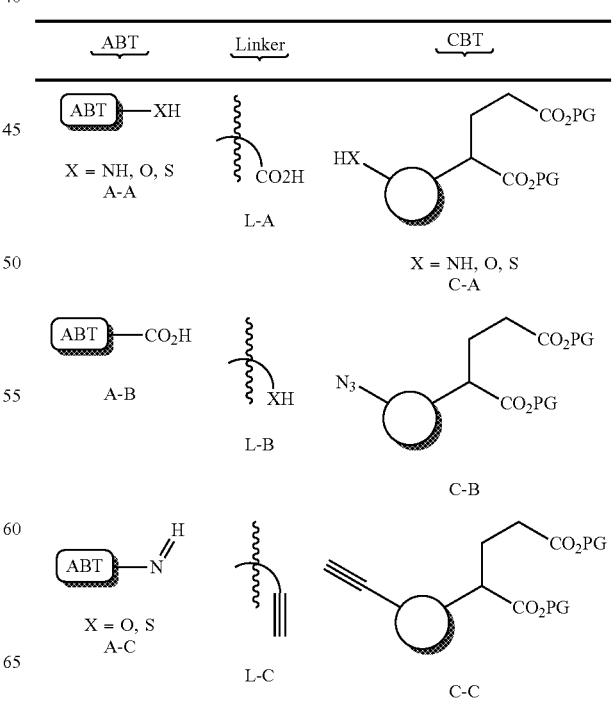

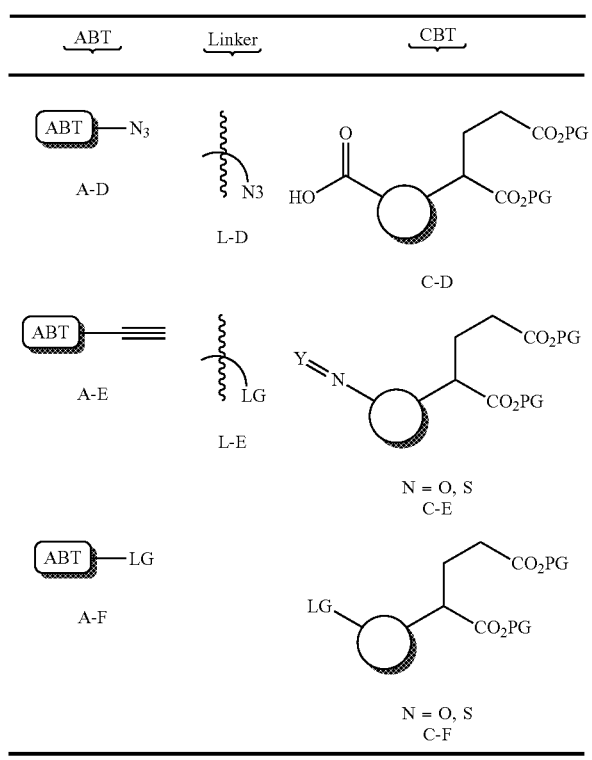

LG = leaving group, such as Cl, Br, OTs, ect.
PG = protecting group, such as t-Bu, Bn, etc.

Synthesis of functional ARMs conjugated to TLR 7/8 agonists with maximal potency at TLR7/8.

Rationale and Preliminary Data

Since imiquimod was first described in 1985, numerous studies have reported on the structure-activity relationships of the compound and its derivatives.[24, 33, 34] The N-1 position on the imidazole ring has successfully been functionalized with linkers to fluorophores and to large proteins with retention of potency.[35-37] We thus attached a short polyethylene glycol (PEG) linker to an imiquimod derivative and coupled all three functional motifs (PSMA binding motif, antibody recruiting motif, and TLR activating motif) to a central triazine core to generate a prototype antibody recruiting molecule conjugated to a TLR7/8 agonist (termed ARM-P8-IMQ; compound 1.6, see FIG. 5). The inventors previously investigated and optimized the linker length joining the PSMA and antibody binding motifs in the unconjugated ARM using extensive biochemical and X-ray crystallographic studies.[38] The PEG-3 linker for the TLR7/8 agonistic motif was selected as a starting point based on the short linker lengths used in previous TLR7/8 agonist protein conjugates.[28, 36,39]

Hypothesis and Research Design

The inventors hypothesized that by systematically altering the length and composition of the linker that joins the [TLR] moiety (in a preferred embodiment, imiquimod) to the ARM core the result will be ARM conjugates exhibiting maximal immunostimulatory properties. These properties include recruitment of antibodies with the same potency as unconjugated ARMs, agonism at TLR7/8, and induction of proinflammatory cytokine release.

Synthesis of ARM-P8-IMQ derivatives: The inventors substitute the PEG-3 linker used in the ARM-P8-IMQ prototype with longer linkers of 6, 8 and 10 subunits. The longer linkers are believed to be needed in order to simultaneously engage TLR7/8, anti-DNP antibody, and PSMA by ARM-P8-IMQ within the endosome. The inventors also synthesize a derivative that contains an acid labile hydrazone linker to cleave the imiquimod motif within the acidic phagolysosome. The interaction of liberated imiquimod with its receptor might occur with greater frequency than the three component co-engagement postulated to occur in ARM-P8-IMQ with a non-labile linker.

Characterization of Receptor Binding by ARM-P8-IMQ and Derivatives:

The inventors have previously developed cellular assays for assessment of ARM binding. Assessment of binding to PSMA is performed by incubating ARM-P8-IMQ with murine prostate cells transfected with human PSMA (RM1.PGLS cells, received from Dr. Michael Sadelain of MSKCC).[40-42] Ternary complex formation (of prostate cancer cell+ARM-P8-IMQ+anti-DNP antibody) is measured by flow cytometry using Alexa488 labeled anti-DNP antibodies. Given that downstream NF-κB transcriptional activity is the typical readout of TLR7/8 agonism, the inventors use a RAW macrophage cell line transfected with a luciferase construct under the control of an NF-κB responsive promoter. Luminescence is monitored following RAW cell phagocytosis of ARM-P8-IMQ-opsonized target cells, with comparison to ARM-P8 in the presence or absence of soluble imiquimod; FIG. 9 depicts the results of this NF-κB assay performed with unconjugated ARM-P8 and Imiquinod. Measurement of soluble proinflammatory cytokines (TNF-α, IFN-α, and IL-12) is also by ELISA. To confirm that activation proceeds through TLR signaling, the inventors also perform these assays using Myd88 and TRIF inhibitory peptides (Invitrogen).

The inventors anticipate that by identifying optimal linker length and composition, the three functional moieties of ARM-P8-IMQ should bind to their targets (anti-DNP antibodies, PSMA, and TLR7/8) with minimal loss of potency compared to the three unconjugated small molecules.

Alternate Strategies

In addition to the use of imiquimod as TLR7/8 agonist, other TLR7/8 agonists are also used in the conjugation strategy (see above). Although imiquimod derivatives are most attractive to the strategy because of the extensive human clinical data available, numerous other agonists for these receptors have been reported with sufficiently defined structure-activity relationships for successful functionalization.[28, 39, 43] Thus, the use of Rintatolimod, SMP-105, IPH-3102, CBLB502, MGN-1706, IMO-2055, ANA773, OM-174, ISS1018, Agatolimod, 852A and Cadi-05 in addition to imiquimod as TLR 7/8 agonists represent alternative approaches to providing trifunctional compounds according to the present invention.

Exploration of the Mechanism by which TLR 7/8 Agonist-Conjugated ARMs Mediate Innate and Adaptive Anti-Tumor Immune Responses In Vitro.

Rationale and Preliminary Data

The inventors have previously evaluated unconjugated ARMs in antibody-dependent cellular cytotoxicity (ADCC) and phagocytosis (ADCP) assays. ADCC is measured by a calcein-release assay using human PBMCs (purchased from Astarte Biologics) to lyse human prostate cancer LNCaP cells (FIG. 10A). The inventors and their colleagues have also developed a two-color flow cytometry-based protocol for ADCP wherein they differentially label target and effector cells using membrane dyes, then quantitate phagocytosis by measurement of the population showing dual-color fluorescence (FIG. 10B). The inventors have optimized this protocol with various target and effector cell lines, and have PSMA negative cell lines as control targets. They have also shown that ARMs can induce superoxide production in a targeted manner when interferon-gamma (IFN-γ) primed U937 cells are incubated with PSMA-expressing cells (FIG. 10C).

Hypothesis and Research Design

The inventors have hypothesized that the conjugation of imiquimod to ARMs enhances the ARM's (conjugated [ABT] and [CBT]) ability to mediate tumor lysis by innate immune cells while further stimulating APC activation and the generation of anti-tumor T-cells.

In Vitro Characterization of ARM-P8-IMQ's Innate Immune Functionality:

The inventors compare the ability of ARM-P8-IMQ and ARMs with or without soluble imiquimod to stimulate innate effector function in the ADCC, ADCP, and superoxide burst assays described above. Since imiquimod acts mainly through induction of a transcriptional program, the assays are modified to include a second pulse of target cells 12 to 24 hours after the first to allow time for AMR-P8-IMQ to activate innate immune cells. The approach uses bone-marrow derived macrophages from C57BL/6 mice as effector cells and will measure their surface expression of activating vs inhibitory FcγR[44] by flow cytometry both before and after treatment with ARM-opsonized targets.

In Vitro Characterization of ARM-P8-IMQ's Adaptive Immune Functionality:

The inventors isolate spleen-derived CD8+CD11b- and CD8-CD11b+ DC subsets with first CD11c+Miltenyi magnetic beads (to enrich for DCs) followed by flow cytometric sorting staining with antibodies against CD8 and CD11b for use in adaptive immunity assays.[45, 46] The maturation of these DCs following ARM-induced phagocytosis of tumor cells will be assessed probing with antibodies against CD80, CD86, MHC I, MHC II, and FcγR subtypes. The murine prostate cancer line RM1.PGLS is then transiently transfected to express ovalbumin (OVA); T-cell stimulation can then be measured by co-incubating CFSE-labeled OVA-specific T-cells (OT-I CD8+ cells and OT-II CD4+ cells harvested from mice from Jackson Labs) with syngeneic DCs that have phagocytosed the OVA expressing targets. Finally, polarization of these T-cells and APCs will be assessed by ELISPOT assays to cytokines such as IFNγ.

These in vitro experiments demonstrate a synergistic mechanism of action for ARM-P8-IMQ mediated by both activating FcγR and TLR7/8. The antibody and PSMA binding motifs of the unconjugated ARMs are expected to mediate PSMA-targeted cytolysis and phagocytosis, with the latter contributing to MHC I and II presentation. The TLR7/8 agonistic motif on the conjugated ARMs should further activate innate immune cells, increase T-cell stimulation and division, and polarize the cytokine profile towards a Th1 microenvironment. This may prove especially relevant in vivo, where lack of DC activation following phagocytosis of mAb-opsonized tumors could potentially lead to T-cell anergy against tumor epitopes or even induction of Tregs.

Potential Pitfalls and Alternate Strategies—

Results of the adaptive immunity assays may be strongly influenced by the DC isolation protocol.[46] While our selected protocol has been widely used in similar experiments investigating tumor antigen cross-presentation, we also have the ability to culture murine bone-marrow derived DCs in the presence of GM-CSF and IL-4 to generate immature APCs, with further maturation induced by a cocktail of TNFα, IL-1β, IL-6, and PGE$_2$.[14, 15, 46] Both immature and mature DCs can thus be assessed in the T-cell stimulation and polarization assays. Also, after in vivo experiments are conducted (see Aim 3 and Timeline of Experiments), immunohistochemical staining of tumor sections and flow cytometry of tumor infiltrates may reveal innate effector and DC subsets that are more relevant to evaluate in these in vitro assays.

Aim 3: Assess the Extent to which Imiquimod Conjugation Improves the Efficacy of ARMs in an Immunocompetent Murine Model of Prostate Adenocarcinoma.

Rationale and Preliminary Data—

We have demonstrated the biological relevance of ARMs in two murine models of prostate cancer. First, athymic NCr-nu/nu mice were subcutaneously implanted with human LNCaP prostate cancer xenografts. Treatment with ARM-P8 following DNP immunization significantly increased mouse survival and decreased tumor growth with comparable efficacy to the standard antimitotic chemotherapy agent docetaxel (FIG. 11). In a complementary model, NOD/SCID mice were transplanted with human peripheral blood lymphocytes (huPBLs) and then implanted with LNCaP xenografts; treatment with an ARM-P8 derivative in the presence of DNP immunization gave similar results as the previous study.[11]

While these models represent important initial studies, accurate assessment of the immunologic effect of ARMs and ARM conjugates requires an immunocompetent model. Athymic NCr/nu mice lack T-cells and hence cannot mount adaptive immune responses against tumors. The hu-PBL transplant model is an artificial system in which human lymphocytes do not receive the full range of growth and survival signals from the murine host, leading to various subtle immunodeficiencies. Moreover, the huPBLs were not HLA-matched to the LNCaP xenografts, so true CTL responses against the tumor could not be completely disentangled from allograft rejection. Thus, evaluation of improved ARM derivatives must be performed in an immunocompetent host.

Hypothesis and Research Design—

We hypothesize that, as compared to unconjugated ARMs, imiquimod-functionalized ARMs will enhance elimination of malignancies upon tumor exposure as well as promote immunologic memory to reject subsequent tumor inoculations. We propose to study the in vivo immunomodulation of ARMs and ARM conjugates in immunocompetent C57BL/6 mice implanted with syngeneic murine prostate tumors which stably express human PSMA (RM1.PGLS cells).[47] Negative control animals will be injected with non-PSMA expressing RM1 cells. The murine homolog of human PSMA is only expressed at low levels on RM1 cells; expression of mPSMA does not follow hPSMA patterns and does not increase in prostate neoplasms.[48] Previous in vivo studies with the parent ARM showed no off-target toxicities in mouse tissues expressing high levels of mPSMA, such as the kidney.

Preliminary pharmacokinetic studies will be performed to determine serum half-life of ARM-P8-IMQ, followed by a two-week toxicity study to evaluate gross hematologic and constitutional endpoints. Mice will be immunized with DNP-Ficoll and anti-DNP antibody titers will be measured after 14 days. Next, the ability of ARM-P8-IMQ to extend survival and reduce tumor volume in mice with subcutaneous flank tumors will be compared to results in mice treated with saline or unconjugated ARM-P8+/− soluble imiquimod. Additionally, relative levels of proinflammatory vs. anti-inflammatory cytokines in the tumors will compared by ELISA to serum levels of cytokines to assess local vs.

systemic immune activation. We will also perform immunohistochemical and flow cytometric studies of tumors to identify specific recruited leukocyte populations. Finally, mice that survive the initial tumor implantation will be re-challenged with syngeneic tumors in the absence of ARM treatment to assess the formation of anti-tumor memory responses.

These in vivo studies provide a proof-of-concept of a small molecule immunomodulator capable of mediating targeted innate and adaptive anti-tumor responses. The use of an immunocompetent mouse model permits correlation of in vivo leukocyte and lymphocyte populations in the tumor with in vitro mechanistic studies.

Alternate Strategies

The pharmacokinetic profile of compounds according to the present invention is compared to the parent compound ARM-P8. Performance of more detailed pharmacokinetic studies and identification of breakdown products of the molecule in serum by LC-MS provides insight into chemical modifications to be performed to increase the stability in vivo. These modification are made based on metabolite structure.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. Any inconsistency between the material incorporated by reference and the material set for in the specification as originally filed shall be resolved in favor of the specification as originally filed. The foregoing detailed description and examples have been given for clarity of understanding only. No unnecessary limitations are to be understood therefrom. The invention is not limited to the exact details shown and described, for variations obvious to one skilled in the art will be included within the invention defined by the following claims.

All headings are for the convenience of the reader and should not be used to limit the meaning of the text that follows the heading, unless so specified.

EXAMPLES

Research Design and Methods

Since imiquimod was first described in 1985, numerous studies have reported on the structure-activity relationships of the compound and its derivatives.[24, 33, 34] The N-1 position on the imidazole ring has successfully been functionalized with linkers to fluorophores and to large proteins with retention of potency.[35-37] Accordingly, the inventors thus attached a short polyethylene glycol (PEG) linker to an imiquimod derivative and coupled all three functional motifs (PSMA binding motif, antibody recruiting motif, and TLR activating motif) to a central triazine core to generate a prototype antibody recruiting molecule conjugated to a TLR7/8 agonist (termed ARM-P8-IMQ; see Scheme, FIG. 5). The inventors previously had investigated and optimized the linker length joining the PSMA and antibody binding motifs in the unconjugated ARM using extensive biochemical and X-ray crystallographic studies.[38] The PEG-3 linker for the TLR7/8 agonistic motif was selected as a starting point based on the short linker lengths used in previous TLR7/8 agonist protein conjugates.[28, 36, 39]

Research Design—

By systematically altering the length and composition of the linker that joins the imiquimod derivative to the ARM core (linkedCBT and ABT) the inventors design ARM conjugates with maximal immunostimulatory properties. These properties include recruitment of antibodies with the same potency as unconjugated ARMs, agonism at TLR7/8, and induction of proinflammatory cytokine release.

Synthesis of ARM-P8-IMQ derivatives: The inventors substitute the PEG-3 linker used in the ARM-P8-IMQ prototype with longer linkers of 6, 8 and 10 subunits. The longer linkers may be needed in order to simultaneously engage TLR7/8, anti-DNP antibody, and PSMA by ARM-P8-IMQ within the endosome. The inventors also synthesize a derivative that contains an acid labile hydrazone linker to cleave the imiquimod motif within the acidic phagolysosome. The interaction of liberated imiquimod with its receptor might occur with greater frequency than the three component co-engagement postulated to occur in ARM-P8-IMQ with a non-labile linker.

Characterization of receptor binding by ARM-P8-IMQ and derivatives: We have previously developed cellular assays for assessment of ARM binding. The inventors assess binding to PSMA by incubating ARM-P8-IMQ.

The invention claimed is:
1. A compound according to the chemical structure:

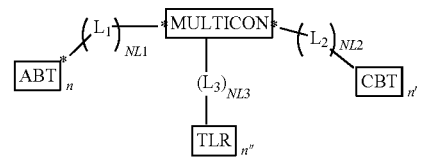

Wherein [ABT] is an antibody binding moiety comprising a hapten which is capable of binding to an antibody in a patient according to the chemical formula:

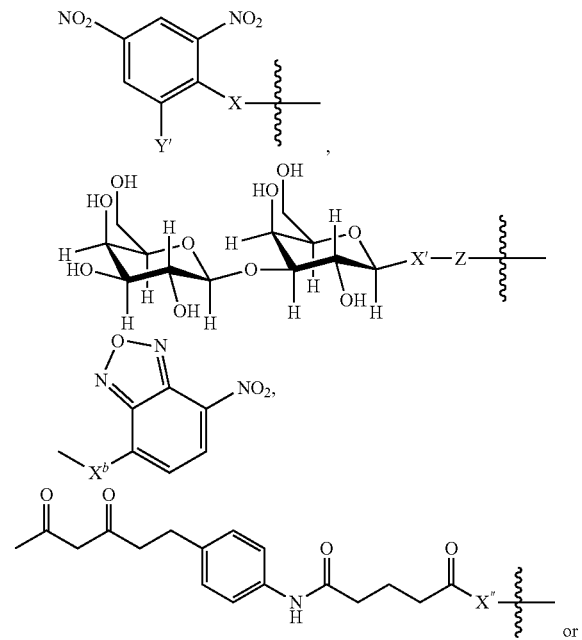

-continued

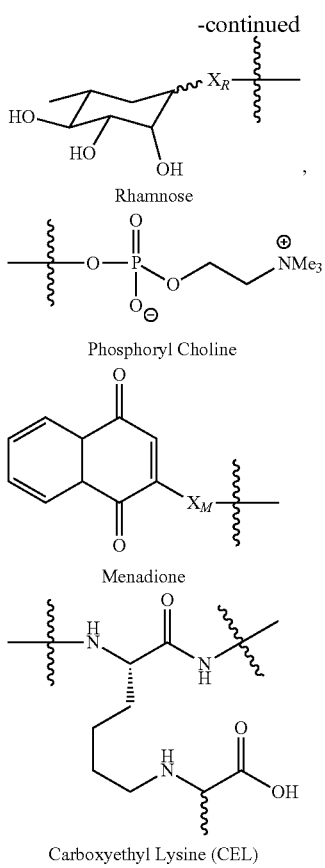

Rhamnose

Phosphoryl Choline

Menadione

Carboxyethyl Lysine (CEL)

Where Y' is H or $NO_2$;
X is O, $CH_2$, $NR^1$, S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;
X' is $CH_2$, O, N—R" or S;
$R^{1'}$ is H or $C_1$-$C_3$ alkyl;
Z is a bond, a monosaccharide, disaccharide, oligosaccharide, glycoprotein or glycolipid;
$X^b$ is a bond, O, $CH_2$, $NR^1$ or S;
X" is O, $CH_2$, $NR^1$;
$X_R$ is O or S;
$X_M$ is O or S;
$R^1$ is H, a $C_1$-$C_3$ alkyl group or a $-C(O)(C_1$-$C_3)$ group, or a group according to the chemical structure:

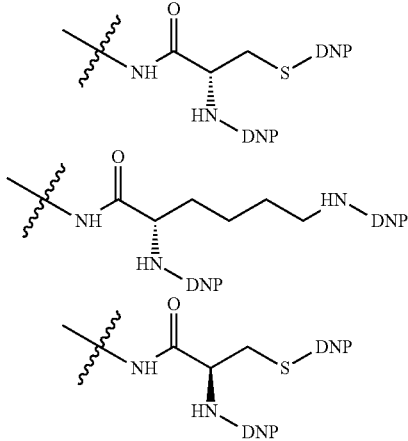

-continued

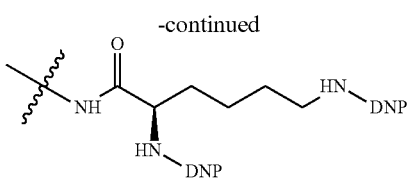

wherein each of said DNP groups is a dinitrophenyl group linked through an amino group or a thio group as indicated to the amino acid moiety;

[CBT] is a cell binding moiety capable of binding to prostate specific membrane antigen (PSMA) on the cell surface of a cancer cell in said patient according to the chemical formula:

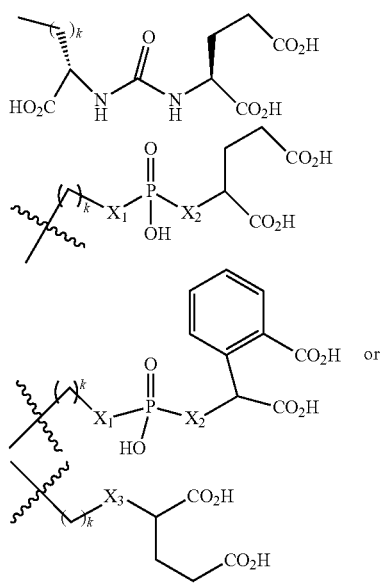

Where $X_1$ and $X_2$ are each independently $CH_2$, O, NH or S;
$X_3$ is O, $CH_2$, $NR^1$, S(O), $S(O)_2$, $-S(O)_2O$, $-OS(O)_2$, or $OS(O)_2O$;
$R^1$ is H, a $C_1$-$C_3$ alkyl group, or a $-C(O)(C_1$-$C_3)$ group;
k is an integer from 0 to 20;
[TLR] is a Toll-like Receptor (TLR) agonist moiety according to the chemical structure;

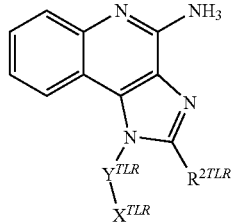

Where $R^{2TLR}$ is moiety which is 3-4 atoms in length wherein said atoms are carbon, oxygen sulfur or nitrogen, said nitrogen being substitutable by H and or a $C_1$-$C_3$ alkyl group;

Y$^{TLR}$ is 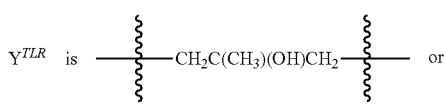 or

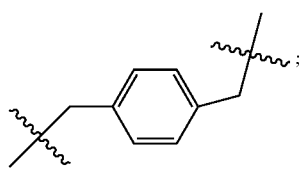

and

X$^{TLR}$ is O, S or N—R$^{NTLR}$ where R$^{NTLR}$ is H or a C$_1$-C$_3$ alkyl group; or

[TLR] is a group according to the chemical structure:

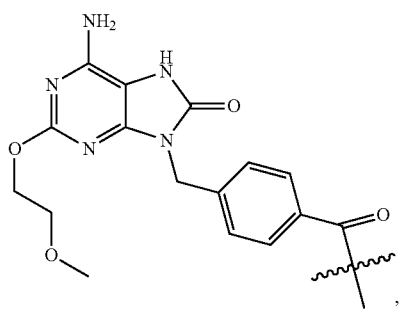

UC-1V150

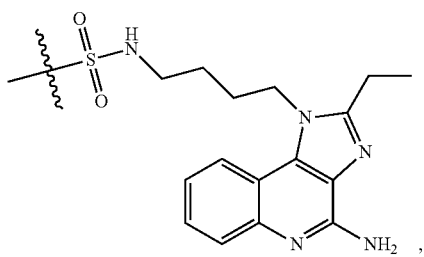

3M-001
N-[4-(4-amino-2-ethyl-1H-imidazo[4,5-c]quinolin-1-yl)butyl]methanesulfonamide

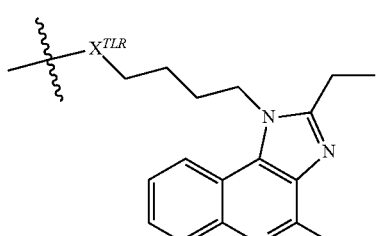

N-[4-(4-amino-2-ethyl-1H-imidazo[4,5-c]quinolin-1-yl)butyl]methane

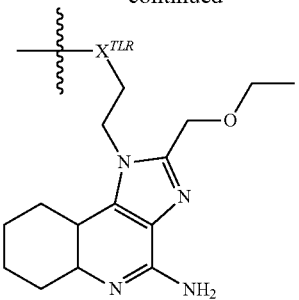

3M-003
4-amino-2-(ethoxymethyl)-alpha, alpha- dimethyl-6,7,8,9-tetrahydro-1H-imidazo[4,5-c]quinoline-1-ethanol or

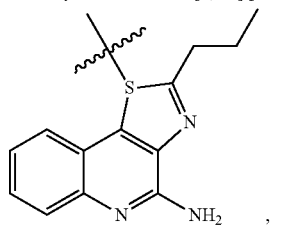

3M-002
2-propylthiazolo[4,5-c]quinolin-4-amine where X$^{TLR}$ is the same as above,
or a salt form thereof;

L$_1$ is at least one linker group which links [MULTICON] to [ABT] in aid compound;

L$_2$ is at least one linker group which links [MULTICON] to [CBT] in said compound;

L$_3$ is at least one linker group which binds [MULTICON] to [TLR] in said compound;

Wherein any one or more of L$_1$, L$_2$ and L$_3$ optionally is or comprises a labile linker;

[MULTICON] is a multifunctional connector molecule which binds to said L$_1$, L$_2$ and L$_3$ linker groups, said multifunctional connector molecule having the chemical structure:

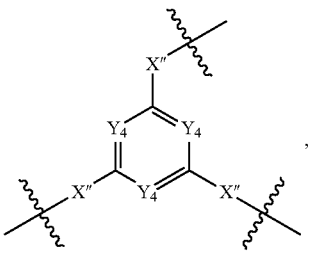

Wherein each Y$_4$ is N; and
Each X″ is N—H;
Each n, n′ and n″ in a molecule is independently an integer from 1 to 15, and Each of NL1, NL2 and NL3 is independently an integer from 1 to 10 wherein n≥NL1, n′≥NL2 and n″≥NL3,
or a pharmaceutically acceptable salt, stereoisomer, diastereomer, enantiomer, solvate or polymorph thereof.

2. The compound according to claim 1 wherein
n, n′, n″, NL1, NL2 and NL3 are each 1;
[ABT] is an antibody binding moiety according to the chemical formula:

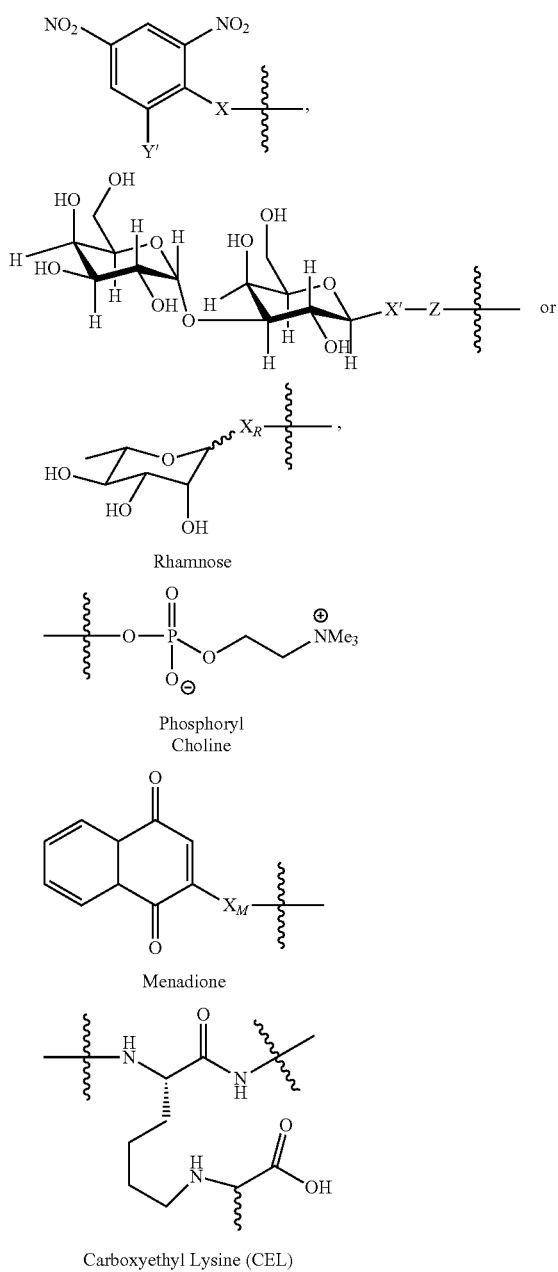

Rhamnose

Phosphoryl Choline

Menadione

Carboxyethyl Lysine (CEL)

Where Y' is H;

X is O, $CH_2$, $NR^1$, S(O), $S(O)_2$, —$S(O)_2$O, —$OS(O)_2$, or $OS(O)_2$O;

$R^1$ is H, a $C_1$-$C_3$ alkyl group, or a —C(O)($C_1$-$C_3$) group;

X' is $CH_2$, O, N—$R^{1'}$ or S;

$R^{1'}$ is H or $C_1$-$C_3$ alkyl;

Z is a bond, a monosaccharide, disaccharide, oligosaccharide, glycoprotein or glycolipid;

$X_R$ is O or S;

$X_M$ is O or S;

$R^1$ is H, a $C_1$-$C_3$ alkyl group or a —C(O)($C_1$-$C_3$) group;

[CBT] is a cell binding moiety according to the chemical formula:

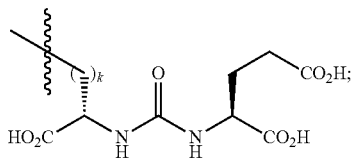

k is 1, 2, 3, 4, 5 or 6;

[TLR] is the same as in claim 1, $L_1$, $L_2$ and $L_3$ are each independently a non-labile linker [NLL] or a labile linker [LL} or a combination of one or more non-labile linkers and labile linkers wherein said non-labile linker [NLL] is a (poly)ethylene glycol or polyethylene-co-polypropylene linker ranging in length from 2 to about 100 ethylene glycol units;

a group according to the chemical structure:

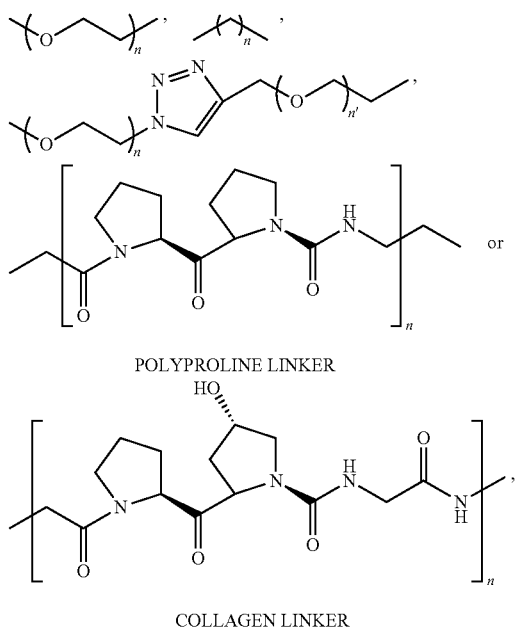

POLYPROLINE LINKER

COLLAGEN LINKER where n and n' are each independently from 1 to 100;

a group according to the structure:

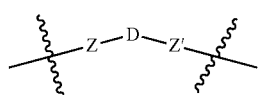

Where Z and Z' are each independently a bond, —$(CH_2)_i$—O, —$(CH_2)_i$—S, —$(CH_2)_i$—N—R,

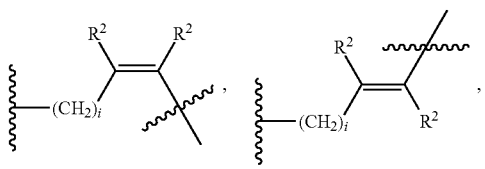

-continued

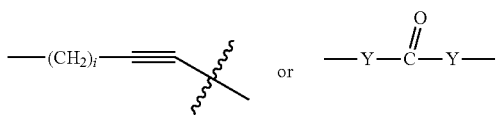

wherein said —(CH$_2$)$_i$ group, if present in Z or Z', is bonded to a multifunctional connector [MULTICON], an optional difunctional connector [CON], [ABT], [CBT] or [TLR];

zole), isoleucine (1-methylpropane), leucine (2-methylpropane), lysine (butyleneamine), methionine (ethylmethylthioether), phenylalanine (benzyl), proline (R$^3$ forms a cyclic ring with R$_a$ and the adjacent nitrogen group to form a pyrrolidine group), hydroxyproline, serine (methanol), threonine (ethanol, 1-hydroxyethane), tryptophan (methyleneindole), tyrosine (methylene phenol) or valine (isopropyl);

m" is an integer from 1 to 25;
m is an integer from about 1 to 100; and
n is an integer from about 1 to 100, or
a group according to the chemical structure:

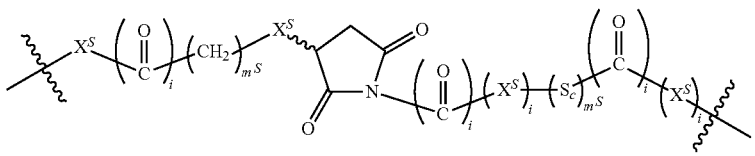

Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 1 to 100;
D is

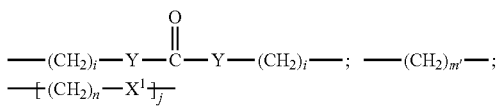

or
a bond, or D is

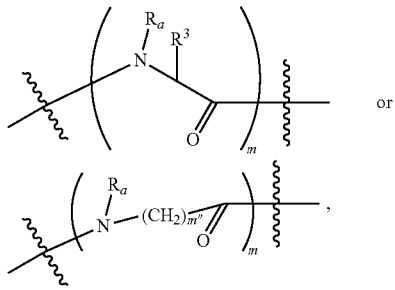

or a polypropylene glycol or polypropylene-co-polyethylene glycol linker having between 1 and 100 glycol units;
with the proviso that Z, Z' and D are not each simultaneously bonds;
j is 1 to 100;
m' is 1 to 100;
n is 1 to 100;
X$^1$ is O, S or N—R;
R is as described above;
R$_a$ is H, C$_1$-C$_3$ alkyl or alkanol or forms a cyclic ring with R$^3$ (proline) or R$^3$ is a side chain derived from an amino acid selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidawhere each X$^S$ is independently S, O or N—R$^S$, preferably S;
R$^S$ is H or C$_{1-3}$ alkyl, preferably H;
S$_c$ is CH$_2$; CH$_2$O; or CH$_2$CH$_2$O;
i is 0 or 1; and
m$^S$ is 0, 1, 2, 3, 4, 5, or 6,
and said labile linker [LL] is a group according to the chemical structure:

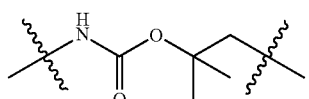

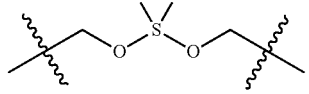

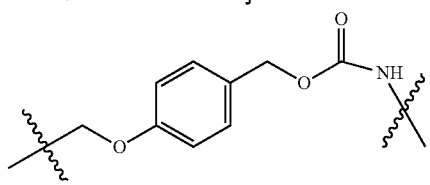

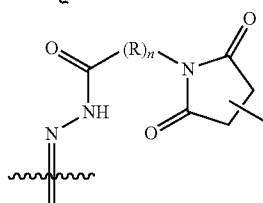

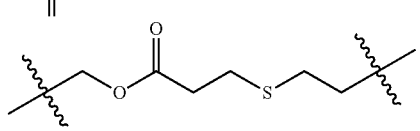

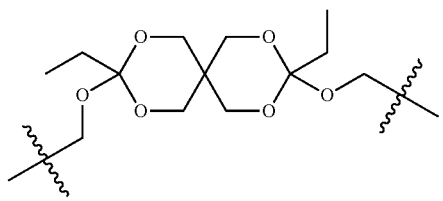

-continued

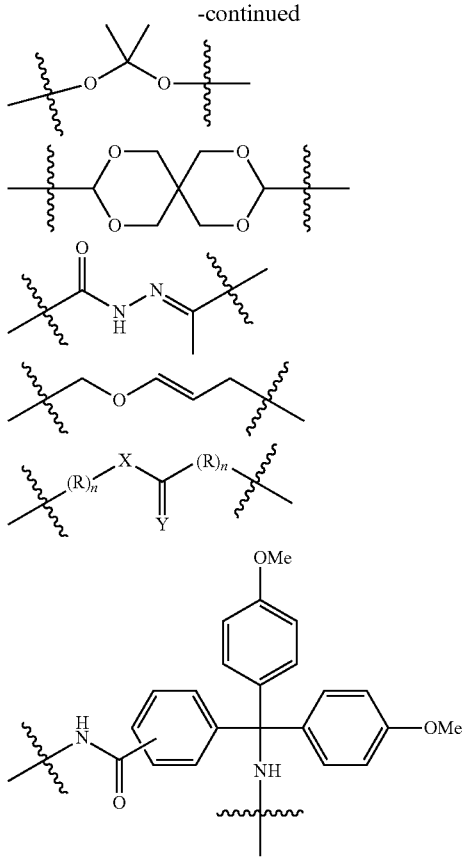

where R is an ethylene glycol group or a methylene group;
n is from 0 to 10;
X is O, N—$R^{AL}$ or S;
$R^{AL}$ is H or a $C_1$-$C_3$ alkyl group;
Y is O or S and
Z=Me, Et, iPr, tBu, Ph, each of which may be optionally substituted with one or more halogen groups and wherein said Ph group may be further optionally substituted with a $C_1$-$C_3$ alkyl group which may be optionally substituted with up to three halogens or OMe; or
[LL] is a group according to the chemical formula:

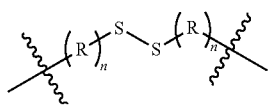

and
R is an ethylene glycol group, or a methylene group; and
n is from 0 to 10; or
[LL] is an enzymatically cleaved labile linker according to the chemical structure:

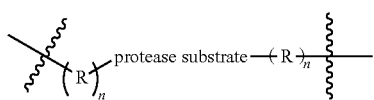

Where the protease (cathepsin) substrate is a peptide substrate of protease containing from 2 to 50 amino acid units;

where R is an ethylene glycol group, or a methylene group; and
n is from 0 to 10; or
[LL] is a group according to the chemical structure:

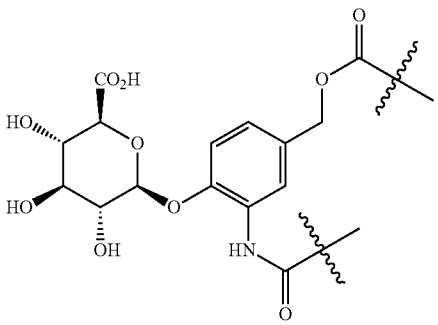 [SMILES: *C(=O)Nc1cc(COC(*)=O)ccc1O[C@@H]1O[C@H](C(=O)O)[C@@H](O)[C@H](O)[C@H]1O]

Where the points of attachment in each of the labile linkers as indicated above are covalently attached to other portions of the labile linker, a multifunctional connector moiety [MULTICON], an optional connector moiety (CON), a non-labile linker (NLL), an [ABT] group, a [CBT] group or a [TLR] group;

And [MULTICON] is the same as in claim 1.

3. The compound according to claim 2 wherein said protease substrate in said labile linker [LL] is -Gly-Phe-Leu-Gly-;

-Ala-Leu-Ala-Leu;

-Phe-Arg-;

-Phe-Lys-;

-Val-Cit-;

-Val-Lys- or

-Val-Ala-.

4. The compound according to claim 1 wherein [ABT] is

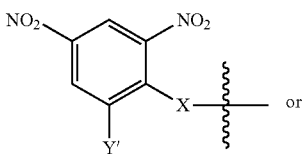

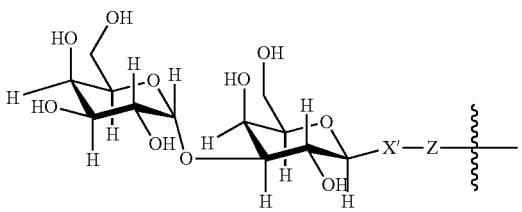

Where X is O or NH;
Y' is H;
X' is O; and

Z is a bond, a monosaccharide or a disaccharide, or [ABT] is

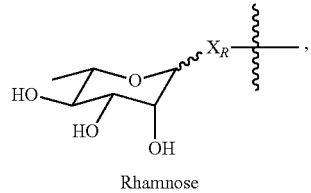

Rhamnose

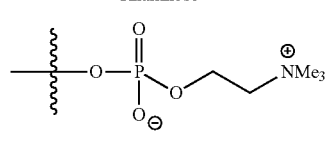

Phosphoryl Choline

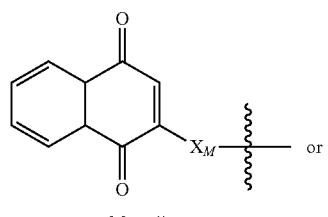

Menadione

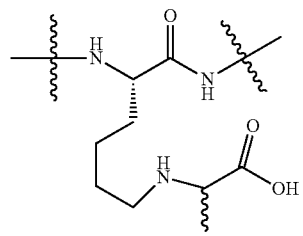

Carboxyethyl Lysine (CEL)

Where $X_R$ is O or S; and
$X_M$ is O or S.

5. The compound according to claim 1 wherein [ABT] is

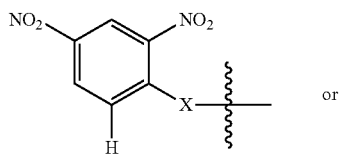

or

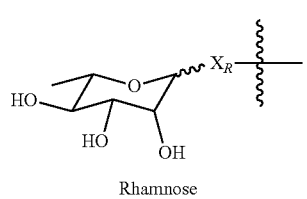

Rhamnose

Where X is O or NH;
and $X_R$ is O or S.

6. The compound according to claim 1 wherein [ABT] is

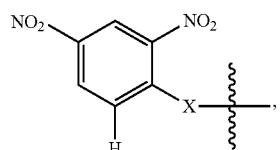

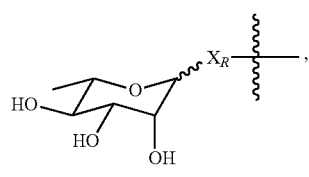

Rhamnose

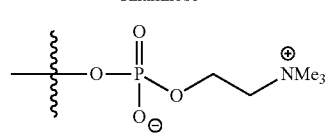

Phosphoryl Choline

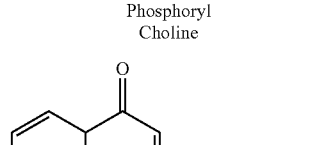

Menadione

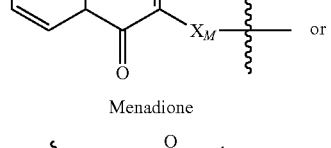

Carboxyethyl Lysine (CEL)

Where X is O or NH;
$X_R$ is O or S; and
$X_M$ is O or S.

7. The compound according to claim 1 wherein [ABT] is

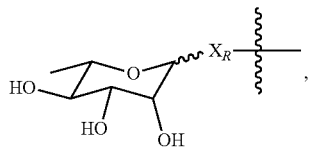

Rhamnose

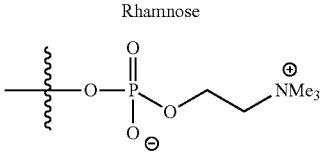

Phosphoryl Choline

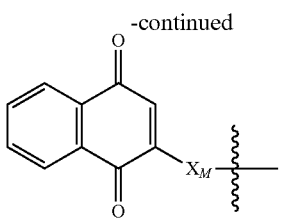

or

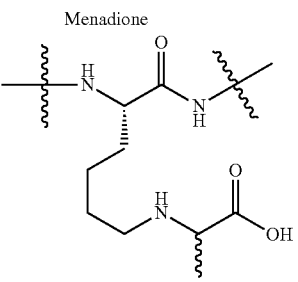

Carboxyethyl Lysine (CEL)

Where $X_R$ is O or S; and
$X_M$ is O or S.

8. The compound according to claim 4 wherein Z is a monosaccharide selected from the group consisting of aldoses, ketoses and aminosugars.

9. The compound according to claim 1 wherein said non-labile linker is a (poly)ethylene glycol or polyethylene-co-polypropylene linker ranging in length from 1 to about 100 ethylene glycol units.

10. The compound according to claim 9 wherein said non-labile linker is a (poly)ethylene glycol linker ranging in length from about 2 to about 10 ethylene glycol units.

11. The compound according to claim 1 wherein said non-labile linker is a linker according to the chemical structure

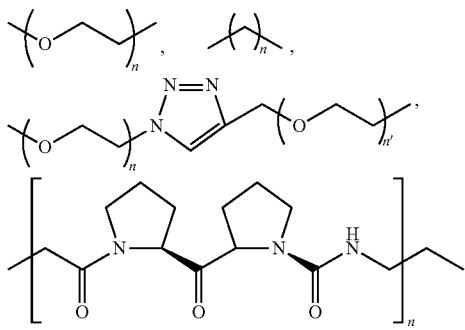

POLYPROLINE LINKER

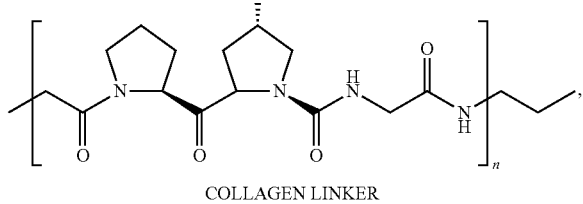

COLLAGEN LINKER where n and n' are each independently from 1 to 100.

12. The compound according to claim 11 wherein n and n' in the linkers of claim 11 are each independently 2 to 10.

13. The compound according to claim 1 wherein said non-labile linker is a group according to the structure:

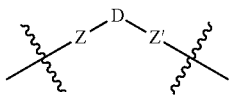

Where Z and Z' are each independently a bond, —(CH$_2$)$_i$—O, —(CH$_2$)$_i$—S, —(CH$_2$)$_i$—N—R,

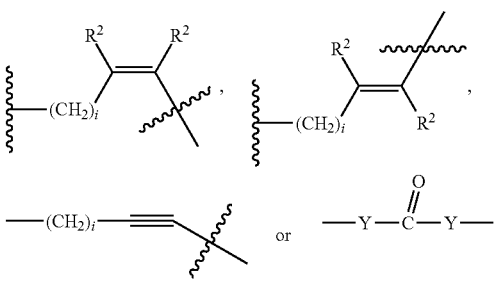

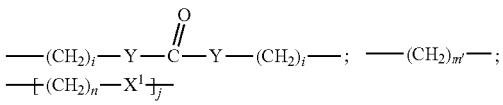

wherein said —(CH$_2$)$_i$ group, if present in Z or Z', is bonded to said multifunctional connector group [MULTICON], an optional difunctional connector group [CON], said [ABT] group, said [CBT] group or said [TLR] group;

Each R is H, or a C$_1$-C$_3$ alkyl or alkanol group;
Each R$^2$ is independently H or a C$_1$-C$_3$ alkyl group;
Each Y is independently a bond, O, S or N—R;
Each i is independently 1 to 100;
D is —(CH$_2$)$_i$—Y—$\overset{\overset{\displaystyle O}{\|}}{C}$—Y—(CH$_2$)$_i$—; —(CH$_2$)$_{m'}$—;
—[(CH$_2$)$_n$—X$^1$]$_j$— or
a bond, or D is

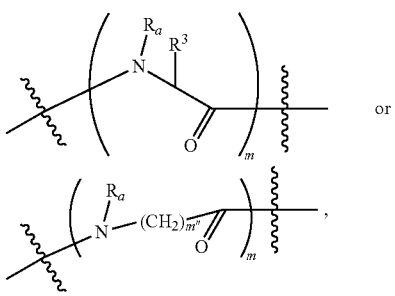

or a polypropylene glycol or polypropylene-co-polyethylene glycol linker having between 1 and 100 glycol units;
with the proviso that Z, Z' and D are not each simultaneously bonds;
j is 1 to 100;
m' is 1 to 100;
n is 1 to 100;
X$^1$ is O, S or N—R;
R is as described above;
R$_a$ is H, C$_1$-C$_3$ alkyl or alkanol or forms a cyclic ring with R$^3$ (proline) and R$^3$ is a side chain derived from an amino acid selected from the group consisting of alanine (methyl), arginine (propyleneguanidine), asparagine (methylenecarboxyamide), aspartic acid (ethanoic acid), cysteine (thiol, reduced or oxidized di-thiol), glutamine (ethylcarboxyamide), glutamic acid (propanoic acid), glycine (H), histidine (methyleneimidazole), isoleucine (1-methylpropane), leucine (2-methylpropane), lysine (butyleneamine), methionine (ethylmethylthioether), phenylalanine (benzyl), proline ($R^3$ forms a cyclic ring with $R_a$ and the adjacent nitrogen group to form a pyrrolidine group), hydroxyproline, serine (methanol), threonine (ethanol, 1-hydroxyethane), tryptophan (methyleneindole), tyrosine (methylene phenol) and valine (isopropyl);

m" is an integer between 0 to 25;

m is an integer from 1 to 100, or a group according to the chemical structure:

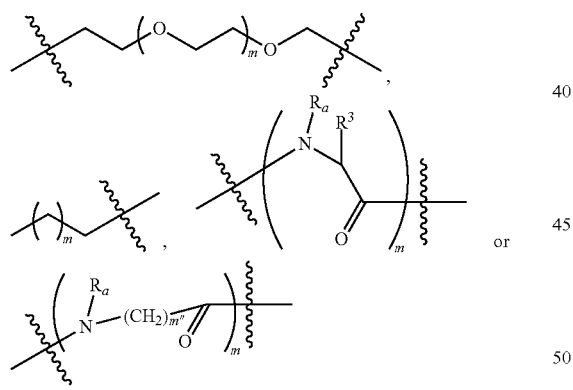

where each $X^S$ is independently S, O or N—$R^S$;
$R^S$ is H or $C_{1-3}$ alkyl;
$S_c$ is $CH_2$; $CH_2O$; or $CH_2CH_2O$;
i is 0 or 1; and
$m^S$ 0, 1, 2, 3, 4, 5, or 6.

14. The compound according to claim 1 wherein said non-labile linker [NLL] is a group according to the structure:

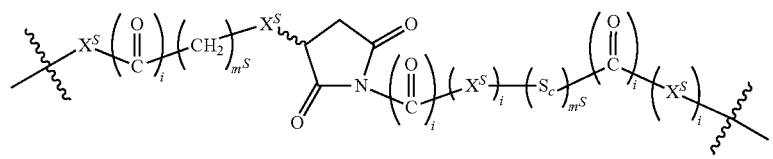

where $R_a$ is H, $C_1$-$C_3$ alkyl or alkanol or forms a cyclic ring with $R^3$ (proline) and $R^3$ is a side chain derived from an amino acid selected from the group consisting of alanine, arginine, asparagine, aspartic acid, cysteine, glutamine, glutamic acid, glycine, histidine, isoleucine, leucine, lysine, methionine, phenylalanine, proline ($R^3$ forms a cyclic ring with $R_a$ and the adjacent nitrogen group to form a pyrrolidine group), hydroxyproline, serine, threonine, tryptophan, tyrosine and valine;

m" is an integer from 1 to 10; and m is an integer from 1 to 100.

15. The compound according to claim 1 wherein said labile linker [LL] is a group according to the chemical structure:

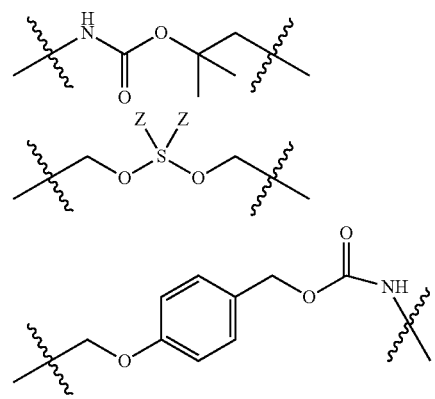

-continued

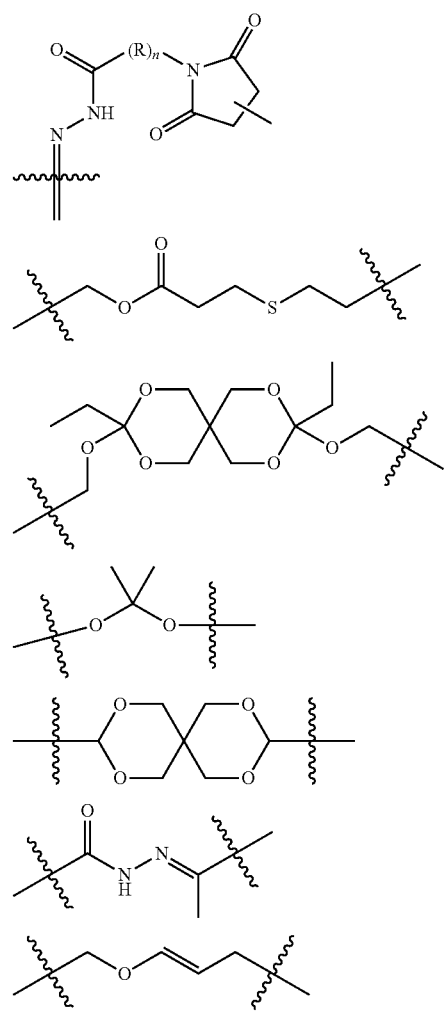

-continued

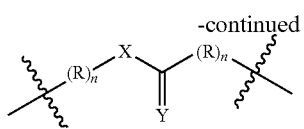

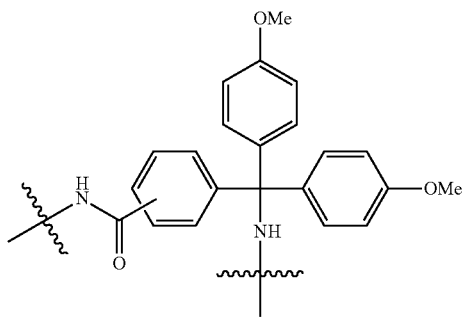

where R is an ethylene glycol group or a methylene group;
n is from 1 to 10;
X is O, N—$R^{AL}$ or S;
$R^{AL}$ is H or a $C_1$-$C_3$ alkyl group;
Y is O or S and
Z=Me, Et, iPr, tBu, Ph, each of which may be optionally substituted with one or more halogen groups and wherein said Ph group may be further optionally substituted with a $C_1$-$C_3$ alkyl group which itself may be optionally substituted with up to three halogens or OMe; or

[LL] is a group according to the chemical formula:

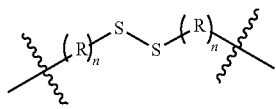

and

Where R is an ethylene glycol group, or a methylene group; and
n is from 1 to 10; or

[LL] is an enzymatically cleavable labile linkers according to the chemical structure:

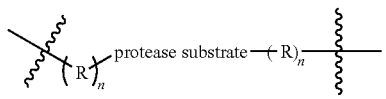

Where the protease (cathepsin) substrate is a peptide substrate of protease containing from 2 to 50 amino acid units;
where R is an ethylene glycol group, or a methylene group; and
n is from 0 to 10; or

[LL] is a group according to the chemical structure:

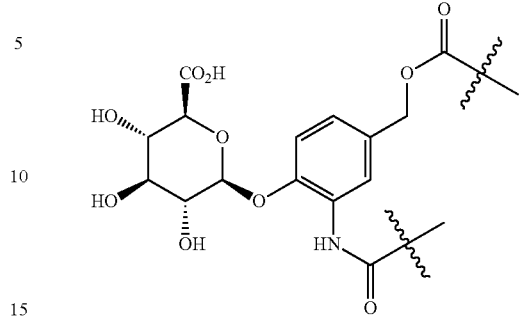

Where the points of attachment in each of the labile linkers as indicated above are covalently attached to other portions of the labile linker, said multifunctional connector [MULTICON], an optional difunctional connector moiety (CON), a non-labile linker (NLL), said [ABT] group, said [CBT] group or said [TLR] group.

16. The compound according to claim 15 wherein said protease substrate is
-Gly-Phe-Leu-Gly-;
-Ala-Leu-Ala-Leu;
-Phe-Arg-;
-Phe-Lys-;
-Val-Cit-;
-Val-Lys- or
-Val-Ala-.

17. The compound according to claim 1 wherein said linker is group according to the chemical formula:

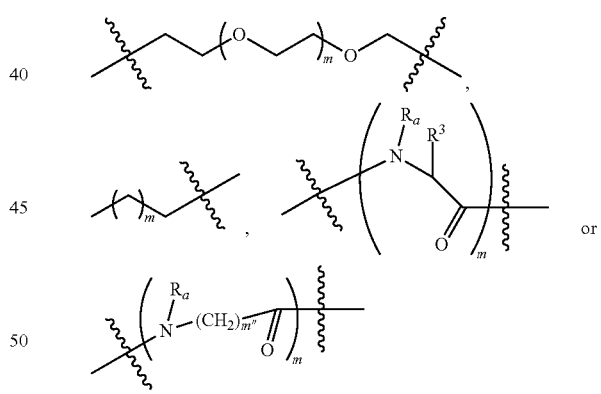

Where $R_a$ is H or forms a cyclic ring with $R^3$ and $R^3$ is a side chain derived from an amino acid selected from the group consisting of alanine, arginine, asparagine, aspartic acid, cysteine, glutamine, glutamic acid, glycine, histidine, isoleucine, leucine, lysine, methionine, phenylalanine, proline ($R^3$ forms a cyclic ring with $R_a$ and the adjacent nitrogen group to form a pyrrolidine group), hydroxyproline, serine, threonine, tryptophan, tyrosine and valine;
m is an integer from 1 to 45; and
m" is an integer from 1 to 10.

18. The compound according to claim 2 wherein said optional difunctional connector group [CON] is a

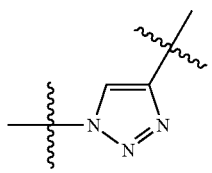 [SMILES: *c1cn(*)nn1]

group.

19. The compound according to claim 1 wherein said linker is a group according to the formula:

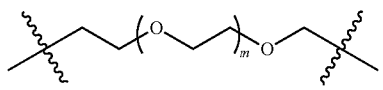

Wherein m is an integer from 1 to 15.

20. A compound according to claim 1 wherein ABT is

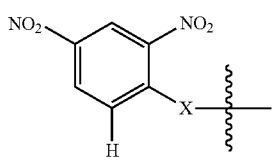

Where X is O or NH;
[CBT] is

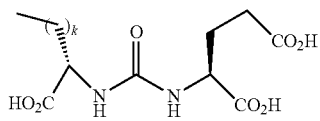

Where k is 4; and
[TLR] is

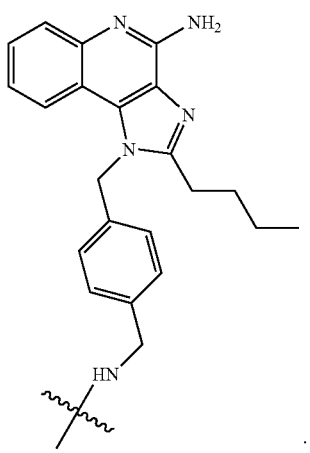 [SMILES: *NCc1ccc(Cn2c(CCCC)nc3c(N)nc4ccccc4c32)cc1]

21. A compound according to claim 20 wherein X is NH, $L_1$ is an alkylene group of between 2 and 12 methylene units in length, $L_2$ is a

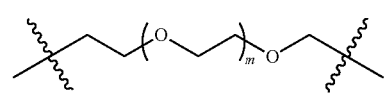

group where m in $L_2$ is 4, 5, 6, 7, 8, 9, 12, 11 or 12; and $L_3$ is a

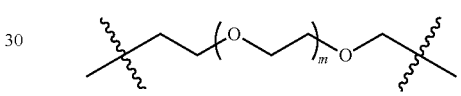

group which is linked to said [TLR] group through a keto group and m in $L_3$ is 2, 3, 4, 5, 6, 7, 8, 9, 10, 11 or 12.

22. The compound according to claim 21 wherein $L_2$ is a

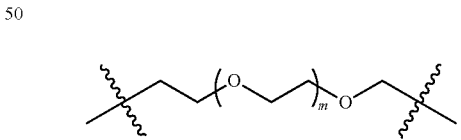

group;

m is 3, 4 5, 6, 7, 8, 9 or 10; and $L_2$ is attached to CBT either directly or through [CON] and wherein [CON] is a triazole.

23. The compound as set forth in attached FIG. 4 according to the chemical structure:

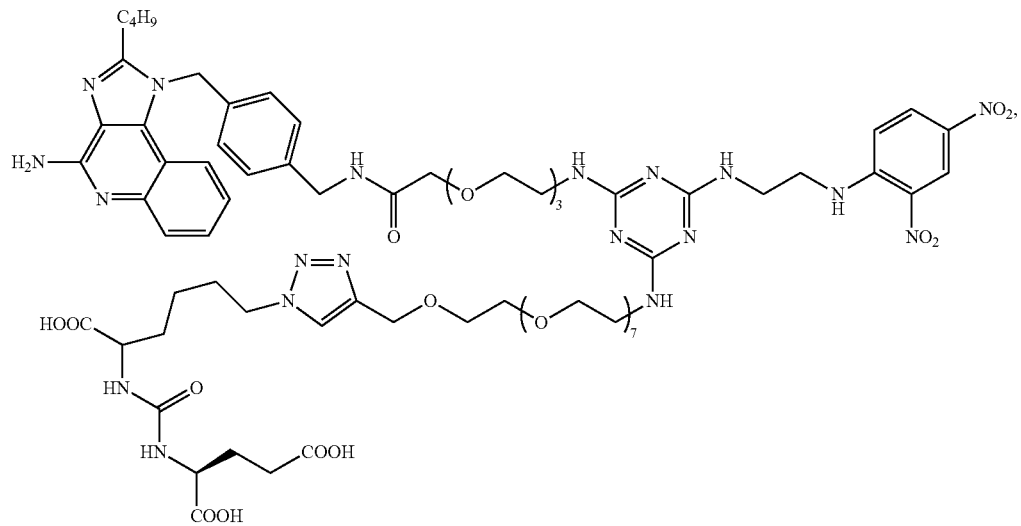

or a pharmaceutically acceptable salt thereof.

24. The compound according to claim 1 wherein $L_3$ is a labile linker.

25. The compound according to claim 20 wherein $L_3$ is a labile linker.

26. A pharmaceutical composition comprising an effective amount of a chimeric compound according to claim 1 in combination with a pharmaceutically acceptable carrier, additive or excipient.

27. The composition according to claim 26 wherein said composition further comprises an effective amount of an additional anticancer agent.

28. The composition according to claim 27 wherein said additional anticancer agent is an antimetabolite, an inhibitor of topoisomerase I and II, an alkylating agent, a microtubule inhibitor or mixtures thereof.

29. The composition according to claim 27 wherein said agent is aldesleukin; aemtuzumab; alitretinoin; allopurinol; altretamine; amifostine; anastrozole; arsenic trioxide; aparaginase; BCG Live; bexarotene capsules; bexarotene gel; bleomycin; busulfan intravenous; busulfan oral; calusterone; capecitabine; carboplatin; carmustine; carmustine with poifeprosan 20 iplant; celecoxib; chlorambucil; cisplatin; cladribine; cyclophosphamide; cytarabine; cytarabine liposomal; dacarbazine; dactinomycin; actinomycin D; dabepoetin alfa; daunorubicin liposomal; daunorubicin, daunomycin; dnileukin diftitox, dexrazoxane; docetaxel; doxorubicin; doxorubicin liposomal; domostanolone propionate; eliott's B soution; epirubicin; eoetin alfa estramustine; etoposide phosphate; etoposide (VP-16); exemestane; flgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); meclorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; nfetumomab; LOddC; orelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof.

30. The composition according to claim 26 further comprising at least one antiandrogen compound.

31. The composition according to claim 26 further comprising at least one GNRh modulator.

32. The composition according to claim 26 further comprising at least one agent selected from the group consisting of flutamide, bicalutamide, nilutamide, cyproterone acetate, ketoconazole, aminoglutethimide, abarelix, leuprolide, goserelin, triptorelin, buserelin, abiraterone acetate, sorafenib and mixtures thereof.

33. The composition according to claim 26 further comprising at least one agent selected from the group consisting of an enlarged prostate agent, eulexin, flutamide, goserelin, leuprolide, lupron, nilandron, nilutamide, zoladex and mixtures thereof.

34. The composition according to claim 26 in oral dosage form.

35. The composition according to claim 26 in parenteral dosage form.

36. The composition according to claim 35 wherein said parenteral dosage form is an intravenous dosage form.

37. The composition according to claim 26 in topical dosage form.

38. A method of treating prostate cancer in a patient in need thereof comprising administering to said patient an effective amount of a compound according to claim 1.

39. The method according to claim 38 wherein wherein said prostate cancer is metastatic prostate cancer.

40. A method of treating prostate cancer in a patient in need thereof comprising administering to said patient an effective amount of a composition according to claim 27.

41. A method of inhibiting metastasis of prostate cancer in a patient in need thereof comprising administering to said patient an effective amount of a compound according to claim 1 to said patient.

42. A method of treating cancer in a patient in need thereof comprising administering to said patient a composition according to claim 26.

43. The method according to claim 42 wherein said cancer is stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

44. A method of treating prostate cancer in a patient wherein said patient also has another form of cancer, said method comprising administering to said patient an effective amount of a composition according to claim 27.

45. The method according to claim 44 wherein said other form of cancer is stomach, colon, rectal, liver, pancreatic, lung, breast, cervix uteri, corpus uteri, ovary, testis, bladder, renal, brain/CNS, head and neck, throat, Hodgkin's disease, non-Hodgkin's lymphoma, multiple myeloma, leukemia, melanoma, non-melanoma skin cancer, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer or lymphoma.

46. The method according to claim 44 wherein said other form of cancer is a carcinoma, a malignant melanoma, a myeloproliferative disease, a sarcoma, a tumor of the central nervous system, a germ-line tumor, a mixed type of neoplasia or a tumor of mixed origin.

* * * * *